United States Patent
Cecere et al.

(10) Patent No.: US 9,957,261 B2
(45) Date of Patent: May 1, 2018

(54) 6-AMINO-5,6,7,8-TETRAHYDRO-NAPHTHALEN-2-YL OR 3-AMINOCHROMAN-7-YL DERIVATIVES

(71) Applicant: Hoffmann-La Roche Inc., Little Falls, NJ (US)

(72) Inventors: Giuseppe Cecere, Basel (CH); Guido Galley, Rheinfelden (DE); Annick Goergler, Colmar (FR); Roger Norcross, Olsberg (CH); Philippe Pflieger, Schwoben (FR); Alina Tirla, Glasgow (GB); Philipp Schmid, Birsfelden (CH)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days. days.

(21) Appl. No.: 15/416,472

(22) Filed: Jan. 26, 2017

(65) Prior Publication Data

US 2017/0137416 A1 May 18, 2017

Related U.S. Application Data

(63) Continuation of application No. PCT/EP2015/067106, filed on Jul. 27, 2015.

(30) Foreign Application Priority Data

Jul. 30, 2014 (EP) ..................... 14179042

(51) Int. Cl.

| | | |
|---|---|---|
| C07D 417/12 | (2006.01) | |
| C07D 231/14 | (2006.01) | |
| C07D 239/28 | (2006.01) | |
| C07D 405/12 | (2006.01) | |
| C07C 233/80 | (2006.01) | |
| C07C 231/12 | (2006.01) | |
| C07C 275/40 | (2006.01) | |
| C07C 273/18 | (2006.01) | |
| C07D 239/42 | (2006.01) | |
| C07D 213/40 | (2006.01) | |
| C07C 209/78 | (2006.01) | |
| C07C 311/21 | (2006.01) | |
| C07D 409/14 | (2006.01) | |
| C07D 213/81 | (2006.01) | |
| C07D 213/73 | (2006.01) | |
| C07D 213/82 | (2006.01) | |
| C07D 311/58 | (2006.01) | |
| C07D 231/20 | (2006.01) | |
| C07D 405/04 | (2006.01) | |
| C07D 241/20 | (2006.01) | |
| C07D 261/18 | (2006.01) | |
| C07D 213/61 | (2006.01) | |
| C07C 255/58 | (2006.01) | |
| C07C 211/60 | (2006.01) | |

(Continued)

(52) U.S. Cl.
CPC .......... C07D 417/12 (2013.01); C07C 209/78 (2013.01); C07C 211/60 (2013.01); C07C 217/92 (2013.01); C07C 231/12 (2013.01); C07C 233/80 (2013.01); C07C 237/48 (2013.01); C07C 255/42 (2013.01); C07C 255/58 (2013.01); C07C 255/60 (2013.01); C07C 273/1854 (2013.01); C07C 275/40 (2013.01); C07C 275/42 (2013.01); C07C 303/40 (2013.01); C07C 311/21 (2013.01); C07D 213/40 (2013.01); C07D 213/61 (2013.01); C07D 213/73 (2013.01); C07D 213/74 (2013.01); C07D 213/75 (2013.01); C07D 213/81 (2013.01); C07D 213/82 (2013.01); C07D 231/14 (2013.01); C07D 231/20 (2013.01); C07D 239/28 (2013.01); C07D 239/42 (2013.01); C07D 241/20 (2013.01); C07D 261/18 (2013.01); C07D 311/58 (2013.01); C07D 405/04 (2013.01); C07D 405/12 (2013.01); C07D 409/14 (2013.01); C07C 2601/02 (2017.05); C07C 2602/10 (2017.05)

(58) Field of Classification Search
None
See application file for complete search history.

(56) References Cited

U.S. PATENT DOCUMENTS 8,969,552 B2 * 3/2015 Drescher ............... C07C 311/21
544/160

FOREIGN PATENT DOCUMENTS

WO 2006/040178 A1 4/2006
WO 2014/041007 A1 3/2014

OTHER PUBLICATIONS

ISR for PCT/EP2015/067106.

* cited by examiner

Primary Examiner — Kamal Saeed
(74) Attorney, Agent, or Firm — Brian L. Buckwalter

(57) ABSTRACT

The present invention relates to compounds TAAR receptor antagonists of formula I wherein X, R, L, Ar and $R^1$ are as described herein, compositions containing compounds of formula I, methods of manufacture of compounds of formula I and methods of treating psychiatric disorders with compounds of formula I.

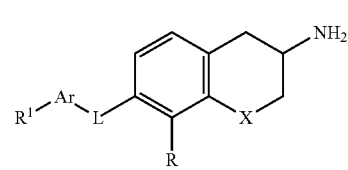

I

10 Claims, No Drawings

(51) Int. Cl.
*C07C 255/60* (2006.01)
*C07C 275/42* (2006.01)
*C07C 217/92* (2006.01)
*C07C 237/48* (2006.01)
*C07C 255/42* (2006.01)
*C07C 303/40* (2006.01)
*C07D 213/74* (2006.01)
*C07D 213/75* (2006.01)

6-AMINO-5,6,7,8-TETRAHYDRO-NAPHTHALEN-2-YL OR 3-AMINOCHROMAN-7-YL DERIVATIVES

CROSS REFERENCE TO RELATED APPLICATIONS

This application is a continuation of International Application No. PCT/EP2015/067106 having an international filing date of Jul. 27, 2015 and which claims benefit under 35 U.S.C. § 119 to European Patent Application No. 14179042.8 filed Jul. 30, 2014. The entire contents of both are incorporated herein by reference.

FIELD OF THE INVENTION

The present invention relates to novel compounds of formula I, as described herein, having pharmaceutical activity, their manufacture, pharmaceutical compositions containing them and their potential use as medicaments.

BACKGROUND OF THE INVENTION

Aberrant activity of Trace Amine Associated Receptors (TAARs), especially for TAAR1 is associated with psychiatric conditions such as depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors. Objects of the present invention show selectivity for TAAR1 receptor over adrenergic receptors, in particular good selectivity vs the human and rat alpha1 and alpha2 adrenergic receptors.

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well-known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gcs. Dysregulation of TAs was shown to contribute to the etiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

REFERENCES USED

1 Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press;

2 Wong, M. L. and Licinio, J. (2001) Research and treatment approaches to depression. *Nat. Rev. Neurosci.* 2, 343-351;

3 Carlsson, A. et al. (2001) Interactions between monoamines, glutamate, and GABA in schizophrenia: new evidence. *Annu. Rev. Pharmacol. Toxicol.* 41, 237-260;

4 Tuite, P. and Riss, J. (2003) Recent developments in the pharmacological treatment of Parkinson's disease. *Expert Opin. Investig. Drugs* 12, 1335-1352, Castellanos, F. X. and Tannock, R. (2002) Neuroscience of attention-deficit/hyperactivity disorder: the search for endophenotypes. *Nat. Rev. Neurosci.* 3, 617-628;

6 Usdin, Earl; Sandler, Merton; Editors. *Psychopharmacology Series, Vol. 1: Trace Amines and the Brain.* [*Proceedings of a Study Group at the 14th Annual Meeting of the American College of Neuropsychoparmacology*, San Juan, Puerto Rico] (1976);

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S.A.* 98, 9474-9475;

Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;
12 Dyck, L. E. (1989) Release of some endogenous trace amines from rat striatal slices in the presence and absence of a monoamine oxidase inhibitor. *Life Sci.* 44, 1149-1156;
13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;
14 Lindemann, L. et al. (2005) Trace amine associated receptors form structurally and functionally distinct subfamilies of novel G protein-coupled receptors. *Genomics* 85, 372-385.

BRIEF SUMMARY OF THE INVENTION

The invention relates to compounds of formula I

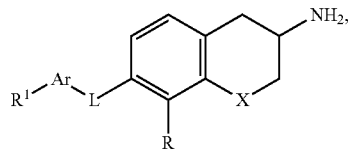

wherein
L is —C(O)NH—, —NHC(O)—, —S(O)$_2$NH—, —NH— or —NHC(O)NH—;
Ar is phenyl, benzyl, naphthyl or heteroaryl, selected from the group consisting of pyridinyl, pyrazolyl, pyrimidinyl, isoxazolyl or pyrazinyl, wherein Ar may be optionally substituted by one, two or three R$^1$;
R$^1$ is hydrogen, lower alkyl, lower alkoxy, halogen, cyano, cycloalkyl, NHC(O)-lower alkyl, lower alkoxy substituted by halogen, lower alkyl substituted by halogen, or is phenyl optionally substituted by one or two halogen atoms, CF$_3$O or lower alkyl, or is furanyl, thiazolyl or thiophenyl, optionally substituted by halogen or lower alkyl;
X is CH or O;
R is hydrogen or halogen;
or to a pharmaceutically acceptable acid addition salt thereof, an enantiomer, a racemic mixture, a mixture of enantiomers or an optical isomer thereof.

In another embodiment, the present invention provides for pharmaceutical compositions comprising compounds of Formula I.

In another embodiment, the present invention provides a method for treating diseases associated with trace amine associated receptors.

DETAILED DESCRIPTION OF THE INVENTION

Objects of the present invention are new compounds of formula I and their pharmaceutically acceptable salts, their use for the manufacture of medicaments for the treatment of diseases related to the biological function of the trace amine associated receptors, their manufacture and medicaments based on a compound in accordance with the invention in the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders. It has now been found that the compounds of formulas I have a good affinity to the trace amine associated receptors (TAARs), especially for TAAR1.

The preferred indications using the compounds of the present invention are depression, psychosis, Parkinson's disease, anxiety, attention deficit hyperactivity disorder (ADHD) and diabetes.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group wherein the alkyl residue is as defined above and which is attached via an oxygen atom.

The term "halogen" denotes chlorine, iodine, fluorine and bromine. The preferred halogen group is fluorine.

As used herein, the term "lower alkyl substituted by halogen" denotes a saturated straight- or branched-chain group containing from 1 to 7 carbon atoms as defined for the term "lower alkyl", wherein at least one hydrogen atom is replaced by a halogen atom. A preferred halogen atom is fluoro. Examples of such groups are CF$_3$, CHF$_2$, CH$_2$F, CH$_2$CF$_3$ or CH$_2$CHF$_2$.

As used herein, the term "lower alkoxy substituted by halogen" denotes a lower alkoxy group as defined above, wherein at least one hydrogen atom is replaced by a halogen atom. Examples of such groups are OCF$_3$, OCHF$_2$, OCH$_2$F, OCH$_2$CF$_3$ or OCH$_2$CHF$_2$.

The term "cycloalkyl" denotes a saturated carbon ring, containing from 3 to 6 carbon atoms, for example cyclopropyl, cyclobutyl, cyclopentyl or cyclohexyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention are compounds of formula I, wherein X is CH$_2$.

One embodiment of the invention are compounds of formula I, wherein X is O.

One embodiment of the invention are compounds of formula I, wherein R is hydrogen.

One embodiment of the invention are compounds of formula I, wherein L is —C(O)NH—, —NHC(O)—, —NH— or —NHC(O)NH—.

One embodiment of the invention are compounds of formula I-b, wherein L is

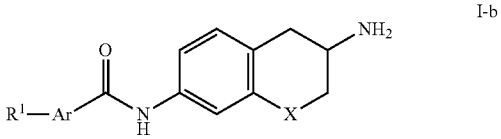

—C(O)NH—.

Other embodiments of the invention are a compound selected from:
N-(6-amino-5,6,7,8-tetrahydronaphthalen-2-yl)-2-(trifluoromethyl)isonicotinamide;
N-(6-amino-5,6,7,8-tetrahydronaphthalen-2-yl)-4-bromo-5-cyclopropyl-1H-pyrazole-3-carboxamide;
N-(6-amino-5,6,7,8-tetrahydronaphthalen-2-yl)-1-(2,2-difluoroethyl)-5-propyl-1H-pyrazole-3-carboxamide;
(R)—N-(6-amino-5,6,7,8-tetrahydronaphthalen-2-yl)-1-(2,2-difluoroethyl)-5-propyl-1H-pyrazole-3-carboxamide;
(S)—N-(6-amino-5,6,7,8-tetrahydronaphthalen-2-yl)-1-(2,2-difluoroethyl)-5-propyl-1H-pyrazole-3-carboxamide;
(R)—N-(6-amino-5,6,7,8-tetrahydronaphthalen-2-yl)-6-methyl-2-(trifluoromethyl)-pyrimidine-4-carboxamide;
(S)—N-(6-amino-5,6,7,8-tetrahydronaphthalen-2-yl)-6-methyl-2-(trifluoromethyl)-pyrimidine-4-carboxamide;
N-(3-aminochroman-7-yl)-1-(2,2-difluoroethyl)-5-propyl-1H-pyrazole-3-carboxamide;
N-(3-aminochroman-7-yl)-6-methyl-2-(trifluoromethyl)pyrimidine-4-carboxamide;
(R)—N-(3-aminochroman-7-yl)-1-(2,2-difluoroethyl)-5-propyl-1H-pyrazole-3-carboxamide;
(S)—N-(3-aminochroman-7-yl)-1-(2,2-difluoroethyl)-5-propyl-1H-pyrazole-3-carboxamide;
(R)—N-(3-aminochroman-7-yl)-6-methyl-2-(trifluoromethyl)pyrimidine-4-carboxamide;
(S)—N-(3-aminochroman-7-yl)-6-methyl-2-(trifluoromethyl)pyrimidine-4-carboxamide;
(R)—N-(6-amino-5,6,7,8-tetrahydronaphthalen-2-yl)-4-chlorobenzamide;
(R)—N-(6-amino-5,6,7,8-tetrahydronaphthalen-2-yl)-2-chlorobenzamide;
(S)—N-(6-amino-5,6,7,8-tetrahydronaphthalen-2-yl)-2-methylisonicotinamide;
(S)-2-acetamido-N-(6-amino-5,6,7,8-tetrahydronaphthalen-2-yl)isonicotinamide;
(S)—N-(6-amino-5,6,7,8-tetrahydronaphthalen-2-yl)-2-ethoxyisonicotinamide;
(S)—N-(6-amino-5,6,7,8-tetrahydronaphthalen-2-yl)-6-(trifluoromethyl)nicotinamide;
(S)—N-(6-amino-5,6,7,8-tetrahydronaphthalen-2-yl)-6-methoxynicotinamide;
(S)—N-(6-amino-5,6,7,8-tetrahydronaphthalen-2-yl)-6-(2,2,2-trifluoroethoxy)nicotinamide;
(S)—N-(6-amino-5,6,7,8-tetrahydronaphthalen-2-yl)-4-chloro-3-(5-chlorofuran-2-yl)-1H-pyrazole-5-carboxamide;
(S)—N-(6-amino-5,6,7,8-tetrahydronaphthalen-2-yl)-4-chloro-5-methylisoxazole-3-carboxamide;
(S)—N-(6-amino-5,6,7,8-tetrahydronaphthalen-2-yl)-1-p-tolyl-1H-pyrazole-4-carboxamide;
(S)—N-(6-amino-5,6,7,8-tetrahydronaphthalen-2-yl)-1-(3,4-dichlorophenyl)-1H-pyrazole-4-carboxamide;
(S)—N-(6-amino-5,6,7,8-tetrahydronaphthalen-2-yl)-1-(4-(trifluoromethoxy)phenyl)-1H-pyrazole-4-carboxamide;
(S)—N-(6-amino-5,6,7,8-tetrahydronaphthalen-2-yl)-2-fluoronicotinamide;
(S)—N-(6-amino-5,6,7,8-tetrahydronaphthalen-2-yl)-6-chloronicotinamide;
(S)—N-(6-amino-5,6,7,8-tetrahydronaphthalen-2-yl)-5,6-dichloronicotinamide;
(S)—N-(6-amino-5,6,7,8-tetrahydronaphthalen-2-yl)-3,4-difluorobenzamide;
(S)—N-(6-amino-5,6,7,8-tetrahydronaphthalen-2-yl)-2-naphthamide;
(S)—N-(6-amino-5,6,7,8-tetrahydronaphthalen-2-yl)-2-(trifluoromethyl)isonicotinamide;
(S)—N-(6-amino-5,6,7,8-tetrahydronaphthalen-2-yl)-2,6-dichloroisonicotinamide;
(S)—N-(6-amino-5,6,7,8-tetrahydronaphthalen-2-yl)-5-chloronicotinamide;
(S)—N-(6-amino-5,6,7,8-tetrahydronaphthalen-2-yl)-2-chloro-6-methylisonicotinamide;
(S)—N-(6-amino-5,6,7,8-tetrahydronaphthalen-2-yl)-3-ethyl-4-methyl-1H-pyrazole-5-carboxamide;
(S)—N-(6-amino-5,6,7,8-tetrahydronaphthalen-2-yl)-4-bromo-5-(2,2-difluoroethoxy)-1-ethyl-1H-pyrazole-3-carboxamide;
(S)—N-(6-amino-1-chloro-5,6,7,8-tetrahydronaphthalen-2-yl)-6-chloronicotinamide;
(R)—N-(3-aminochroman-7-yl)-5-ethoxy-4-methyl-1H-pyrazole-3-carboxamide;
(R)—N-(3-aminochroman-7-yl)-4-chloropyrimidine-2-carboxamide;
(R)—N-(3-aminochroman-7-yl)-4-(2-methylthiazol-4-yl)benzamide;
(R)—N-(3-aminochroman-7-yl)-5-(trifluoromethyl)pyrimidine-2-carboxamide;
(R)—N-(3-aminochroman-7-yl)-1-methyl-5-(thiophen-2-yl)-1H-pyrazole-3-carboxamide;
(R)—N-(3-aminochroman-7-yl)-4-cyano-3-fluorobenzamide;
(R)—N-(3-aminochroman-7-yl)-3,4-difluorobenzamide;
(R)—N-(3-aminochroman-7-yl)-3-ethyl-4-methyl-1H-pyrazole-5-carboxamide;
(R)—N-(3-aminochroman-7-yl)-2-chloro-6-methylisonicotinamide;
(R)—N-(3-aminochroman-7-yl)-2-(trifluoromethyl)isonicotinamide;
(R)—N-(3-aminochroman-7-yl)-2,6-dichloroisonicotinamide; or.
(R)—N-(3-aminochroman-7-yl)-4-bromo-5-(2,2-difluoroethoxy)-1-ethyl-1H-pyrazole-3-carboxamide.

Another embodiment of the invention are compounds of formula I-d, wherein L is —NHC(O)—.

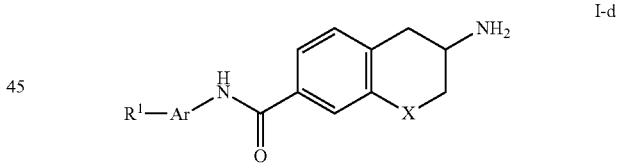

Other embodiments of the invention are a compound selected from:
6-amino-N-(6-ethoxypyridin-3-yl)-5,6,7,8-tetrahydronaphthalene-2-carboxamide;
6-amino-N-(2-cyclopropylpyrimidin-5-yl)-5,6,7,8-tetrahydronaphthalene-2-carboxamide;
6-amino-N-(5-(trifluoromethyl)pyrazin-2-yl)-5,6,7,8-tetrahydronaphthalene-2-carboxamide;
6-amino-N-(4-(trifluoromethyl)phenyl)-5,6,7,8-tetrahydronaphthalene-2-carboxamide;
6-amino-N-(4-(trifluoromethyl)benzyl)-5,6,7,8-tetrahydronaphthalene-2-carboxamide;
6-amino-N-((6-chloropyridin-3-yl)methyl)-5,6,7,8-tetrahydronaphthalene-2-carboxamide;
6-amino-N-(6-chloropyridin-3-yl)-5,6,7,8-tetrahydronaphthalene-2-carboxamide;
6-amino-N-(3-methoxyphenyl)-5,6,7,8-tetrahydronaphthalene-2-carboxamide 6-amino-N-(3-(trifluoromethoxy)phenyl)-5,6,7,8-tetrahydronaphthalene-2-carboxamide;
6-amino-N-(4-ethylphenyl)-5,6,7,8-tetrahydronaphthalene-2-carboxamide;
6-amino-N-(4-chlorophenyl)-5,6,7,8-tetrahydronaphthalene-2-carboxamide;
6-amino-N-(4-fluorophenyl)-5,6,7,8-tetrahydronaphthalene-2-carboxamide;
6-amino-N-(3-chlorophenyl)-5,6,7,8-tetrahydronaphthalene-2-carboxamide;
6-amino-N-(4-cyclopropylphenyl)-5,6,7,8-tetrahydronaphthalene-2-carboxamide;
6-amino-N-(4-cyanophenyl)-5,6,7,8-tetrahydronaphthalene-2-carboxamide;
(R)-6-amino-N-(3-(trifluoromethoxy)phenyl)-5,6,7,8-tetrahydronaphthalene-2-carboxamide; or,
(S)-6-amino-N-(3-(trifluoromethoxy)phenyl)-5,6,7,8-tetrahydronaphthalene-2-carboxamide.

One embodiment of the invention are compounds of formula I, wherein L is —S(O)₂NH—,

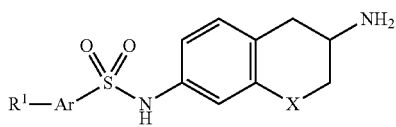

for example, (S)—N-(6-Amino-5,6,7,8-tetrahydronaphthalen-2-yl)-4-chlorobenzenesulfonamide.

One embodiment of the invention are further compounds of formula I, wherein L is NH—,

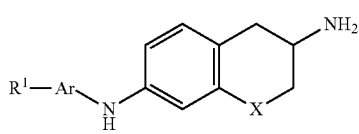

Other embodiments of the invention are a compound selected from:
(S)—N6-(5-(trifluoromethyl)pyrimidin-2-yl)-1,2,3,4-tetrahydronaphthalene-2,6-diamine;
(S)—N6-(5-chloropyrimidin-2-yl)-1,2,3,4-tetrahydronaphthalene-2,6-diamine;
(S)—N6-(5-(trifluoromethyl)pyridin-2-yl)-1,2,3,4-tetrahydronaphthalene-2,6-diamine;
(S)—N6-(4-(trifluoromethyl)phenyl)-1,2,3,4-tetrahydronaphthalene-2,6-diamine;
(S)-4-(6-amino-5,6,7,8-tetrahydronaphthalen-2-ylamino)benzonitrile;
(S)—N6-(4-chlorophenyl)-1,2,3,4-tetrahydronaphthalene-2,6-diamine;
(S)—N6-(4-ethylphenyl)-1,2,3,4-tetrahydronaphthalene-2,6-diamine;
(S)—N6-(3-(trifluoromethoxy)phenyl)-1,2,3,4-tetrahydronaphthalene-2,6-diamine;
(S)—N6-(4-fluorophenyl)-1,2,3,4-tetrahydronaphthalene-2,6-diamine;
(S)—N6-(3-chlorophenyl)-1,2,3,4-tetrahydronaphthalene-2,6-diamine;
(S)—N6-(4-cyclopropylphenyl)-1,2,3,4-tetrahydronaphthalene-2,6-diamine;
(S)—N6-(4-chlorobenzyl)-1,2,3,4-tetrahydronaphthalene-2,6-diamine;
(R)—N7-(5-(trifluoromethyl)pyrimidin-2-yl)chroman-3,7-diamine;
(R)—N7-(5-chloropyrimidin-2-yl)chroman-3,7-diamine; or,
(S)—N6-(3-methoxyphenyl)-1,2,3,4-tetrahydronaphthalene-2,6-diamine.

Another embodiment of the invention are further compounds of formula I, wherein L is —NHC(O)NH—.

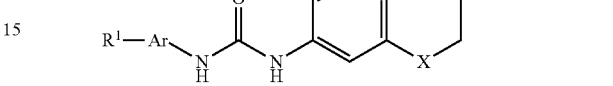

Other embodiments of the invention are a compound selected from:
(S)-1-(6-amino-5,6,7,8-tetrahydronaphthalen-2-yl)-3-(6-(trifluoromethyl)pyridin-3-yl)urea;
(S)-1-(6-amino-5,6,7,8-tetrahydronaphthalen-2-yl)-3-(4-(trifluoromethyl)phenyl)urea;
(S)-1-(6-amino-5,6,7,8-tetrahydronaphthalen-2-yl)-3-((5-chloropyridin-2-yl)methyl)urea;
(S)-1-(6-amino-5,6,7,8-tetrahydronaphthalen-2-yl)-3-(3-(trifluoromethoxy)benzyl)urea;
(S)-1-(6-amino-5,6,7,8-tetrahydronaphthalen-2-yl)-3-(4-ethylphenyl)urea;
(S)-1-(6-amino-5,6,7,8-tetrahydronaphthalen-2-yl)-3-(4-(trifluoromethoxy)phenyl)urea;
(S)-1-(6-amino-5,6,7,8-tetrahydronaphthalen-2-yl)-3-(3-methoxyphenyl)urea;
(S)-1-(6-amino-5,6,7,8-tetrahydronaphthalen-2-yl)-3-(4-chlorobenzyl)urea;
(S)-1-(6-amino-5,6,7,8-tetrahydronaphthalen-2-yl)-3-(4-cyanophenyl)urea;
(S)-1-(6-amino-5,6,7,8-tetrahydronaphthalen-2-yl)-3-(4-cyclopropylphenyl)urea; or,
(S)-1-(6-amino-5,6,7,8-tetrahydronaphthalen-2-yl)-3-(4-chlorophenyl)urea.

The preparation of compounds of formula I of the present invention may be carried out in sequential or convergent synthetic routes. Syntheses of the compounds of the invention are shown in the following schemes 1 to 5 and in the description of 94 specific examples. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1 to 5, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods known in the art, for example, by processes described below, which process comprises a) cleaving off the N-protecting group (PG) from compounds of formula

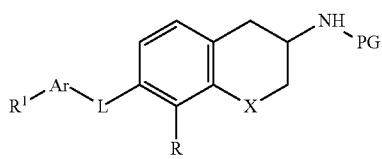

to a compound of formula

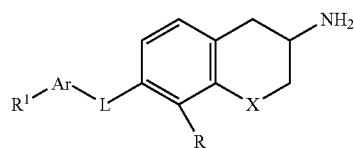

wherein PG is a N-protecting group selected from —C(O)O-tert-butyl (BOC) and the other definitions are as described above, and, if desired, converting the compounds obtained into pharmaceutically acceptable acid addition salts.

General Procedure

For R being hydrogen:

Step A:

Amination of compound II (Y=Br, I, trifluoromethanesulfonate) to form compound III can be accomplished by treatment of II with benzophenone imine in the presence of a palladium or copper catalyst, a ligand and a base in solvents such as dioxane, DME, THF, toluene, DMF and DMSO at elevated temperatures, for instance using a palladium-catalysed Buchwald-Hartwig reaction. Removal of the diphenylmethyl group to release the NH$_2$ group can be effected by hydrogenation with hydrogen under normal or elevated pressure or by transfer hydrogenation using ammonium formate or cyclohexadiene as hydrogen source with a catalyst such as PtO$_2$, Pd—C or Raney nickel in solvents such as MeOH, EtOH, H$_2$O, dioxane, THF, HOAc, EtOAc, CH$_2$Cl$_2$, CHCl$_3$, DMF or mixtures thereof. Another method for the removal of the diphenylmethyl group is the treatment with hydroxylamine or a salt thereof in a polar solvent such as ethanol or methanol without or in presence of a buffer such as sodium acetate or sodium formate.

Preferred conditions are the treatment of the bromide with benzophenone imine in presence of sodium tert.-butoxide, catalytic tris(dibenzylideneacetone)dipalladium and catalytic bis(diphenylphosphino)-1,1-binaphthalene in toluene for 3 hours at 90° C. followed by removal of the diphenylmethyl group by treatment with hydroxylamine hydrochloride and sodium acetate in MeOH at 50° C. overnight.

Step B:

Reaction of compound III with arylhalogenide IV (X=Cl, Br or I) can be accomplished in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium chloroform complex, catalytic 9,9-dimethyl-4,5-bis(diphenylphosphino)xanthene (Xantphos) and caesium carbonate in dioxane in a sealed tube heated at 100° C. for 2 hours.

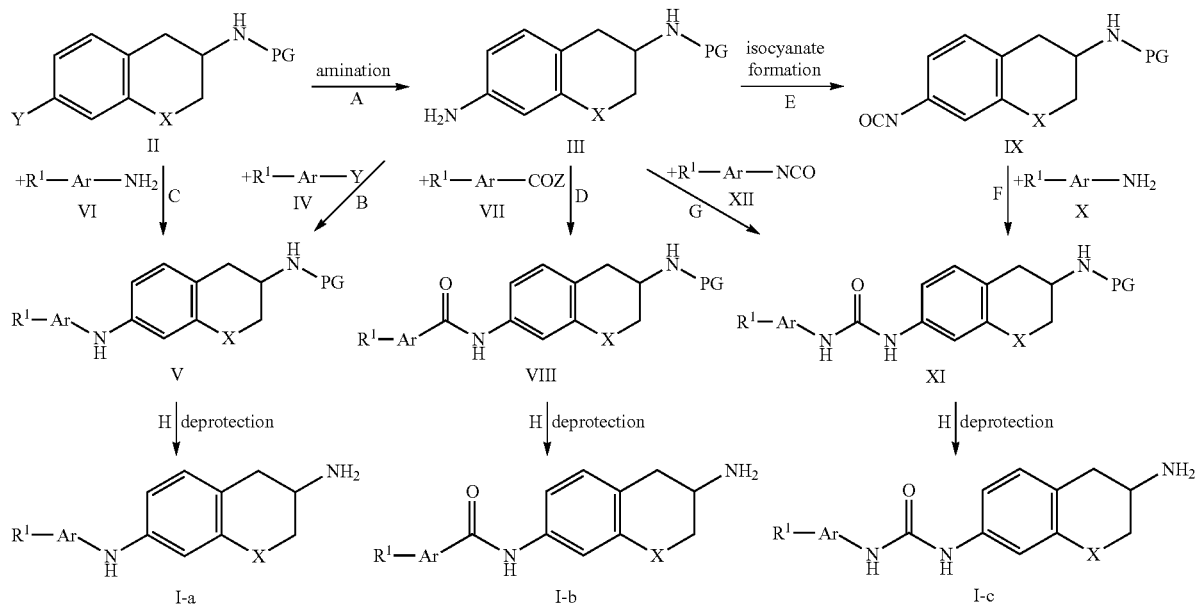

Scheme 1

In case the arylhalogenide IV is activated for nucleophilic substitution, such as a pyrimidine derivative further substituted by electron withdrawing groups, compound III may also be reacted with arylhalogenide IV in a solvent such as dimethylformamide, dimethylacetamide, ethanol or isopropanol in the presence of a base such as triethylamine or N,N-diisopropylethylamine at elevated temperatures. Preferred conditions in such a case is the treatment with are N,N-diisopropylethylamine in isopropanol at 90° C. for 5 hours.

To synthesise other derivatives V where Ar=benzyl, compound III can be reacted with the corresponding benzaldehyde and a reducing agent such as sodium cyanoborohydride, sodium triacetoxyborohydride or sodium borohydride in a solvent such as ethanol, methanol, propanol or isopropanol. Preferred conditions in this case are reacting III with a benzaldehyde in presence of sodium cyanoborohydride in methanol at 40° C. overnight.

Step C:

Compounds V can further be prepared by amination of compound II (X=Br, I, trifluoromethanesulfonate) with an arylamine VI in the presence of a palladium or copper catalyst, a ligand and a base in solvents such as dioxane, DME, THF, toluene, DMF and DMSO at elevated temperatures, for instance using a palladium-catalysed Buchwald-Hartwig reaction. Preferred conditions are catalytic tris (dibenzylidineacetone)dipalladium chloroform complex, catalytic 9,9-dimethyl-4,5-bis(diphenylphosphino)xanthene (Xantphos) and caesium carbonate in dioxane in a sealed tube heated at 100° C. for 2 hours.

Step D:

Amide formation to form compound VIII can be accomplished by a coupling reaction between the amine III and an activated acid derivative such as an acid chloride VII (Z=Cl) in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine. Preferred conditions are N,N-diisopropylethylamine in THF at room temperature for 18 hours.

If desired, the acid chloride VII (Z=Cl) may be prepared in situ from the corresponding carboxylic acid VII (Z=OH) by treatment with oxalyl chloride or 1-chloro-N,N,2-trimethypropenylamine in halogenated solvents such as dichloromethane or 1,2-dichloroethane or ethereal solvents such as diethyl ether, dioxane, THF, DME or TBME in the presence of a catalyst such as DMF. Preferred conditions are dichloromethane at room temperature for 1 hour. Alternatively, amide formation can be accomplished by a coupling reaction between the amine III and carboxylic acids VII (Z=OH) in the presence of a coupling reagent such as 1-ethyl-3-(3-dimethylaminopropyl)carbodiimide (EDC), dicyclohexylcarbodiimde (DCC), O-(benzotriazol-1-yl)-N,N,N',N'-tetramethyluroniumtetrafluoroborate (TBTU), O-(benzotriazol-1-yl)-N,N,N',N'-tetramethyluronium-hexafluorophosphate (HBTU), 1-[bis(dimethylamino)methylene]-1H-1,2,3-triazolo[4,5-b]pyridinium-3-oxid hexafluorophosphate (HATU) or 4-(4,6-dimethoxy-1,3,5-triazin-2-yl)-4-methylmorpholinium chloride (DMTMM) in the presence of an organic base such as triethylamine, N,N-diisopropylethylamine or N-methylmorpholine in halogenated solvents such as DMF, dichloromethane or 1,2-dichloroethane or ethereal solvents such as diethyl ether, dioxane, THF, DME or TBME.

Preferred conditions are TBTU or HBTU with N-methylmorpholine in DMF at 60° C. for 18 hours.

Step E:

Isocyanate formation can be accomplished by treatment of amine III with triphosgene, diphosgene or phosgene in halogenated solvents such as dichloromethane or 1,2-dichloroethane in the presence of an organic base such as triethylamine or N,N-diisopropylethylamine or an inorganic base such as sodium carbonate or potassium carbonate.

Preferred conditions for formation of isocyanate IX are triphosgene and triethylamine in 1,2-dichloroethane at room temperature for 1 hour.

Step F:

Urea formation can be achieved by reacting the isocyanate IX with the amine X in an organic solvent such as dichloromethane or 1,2-dichloroethane. Preferred conditions for formation of urea XI are stirring the crude isocyanate in 1,2-dichloroethane with the amine at room temperature overnight.

Step G:

Formation of urea XI can be accomplished as well by reaction of amine III with an isocyanate XII in a halogenated solvent such as dichloromethane or 1,2-dichloroethane or an ethereal solvent such as diethyl ether, dioxane, THF, DME or TBME at room temperature or elevated temperature.

Preferred conditions are 1,2-dichloroethane as solvent and heating to 50° C. for several hours.

Step H:

Cleavage of the amino protecting group from derivatives V, VIII or XI can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred protecting group is the tert-butoxycarbonyl group. Preferred conditions are the use of HCl in dioxane for 2 to 17 hrs at 60° C. or the use of $CF_3COOH$ in dichloromethane at room temperature overnight.

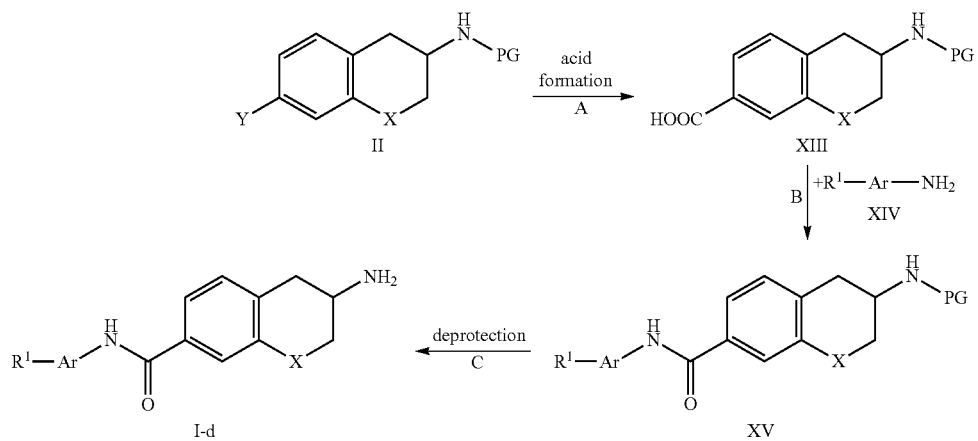

Scheme 2

For R being hydrogen:

Step A:

Formation of the acid XIII from compound II (Y=Br, I, trifluoromethanesulfonate) can be accomplished by several methods such as carbonylation using carbonmonoxide, a base such as triethylamine or N,N-diisopropylethylamine and a suitable transition metal catalyst in an alcoholic solvent mixture followed by saponification of the formed carboxylic ester by a base such as lithium hydroxide, potassium hydroxide or sodium hydroxide in water or a mixture of water and an organic solvent such as tetrahydrofuran or methanol. Alternatively, reaction of compound II with an organometallic base in an ethereal solvent such as diethylether or tetrahydrofuran and treatment of the formed anion with dimethylformamide, followed by oxidation of the formed aldehyde to the acid by various oxidising agents can be used. Preferred conditions for formation of acid XIII are treatment with excess carbon monoxide in a mixture of ethyl acetate and methanol in the presence of triethylamine and 1,1'-bis(diphenylphosphino)ferrocene-palladium(II) dichloride at 50 bar and 110° C. overnight, followed by saponification of the formed ester with lithium hydroxide in a mixture of tetrahydrofuran and water at room temperature overnight.

Step B:

Amide formation can be accomplished by activating the acid XIII by treatment with oxalyl chloride or 1-chloro-N,N,2-trimethypropenylamine in halogenated solvents such as dichloromethane or 1,2-dichloroethane or ethereal solvents such as diethyl ether, dioxane, THF, DME or TBME in the presence of a catalyst such as DMF and subsequent reaction of this acid chloride with amine XIV in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine.

Alternatively, amide formation can be accomplished by a coupling reaction between the amine XIV and carboxylic acids XIII in the presence of a coupling reagent such as DCC, EDC, TBTU, HBTU, HATU or DMTMM in the presence of an organic base such as triethylamine, N,N-diisopropylethylamine or N-methylmorpholine in halogenated solvents such as DMF, dichloromethane or 1,2-dichloroethane or ethereal solvents such as diethyl ether, dioxane, THF, DME or TBME.

Preferred conditions is the activation of acid XIII by 1-chloro-N,N,2-trimethypropenylamine in dichloromethane and reacting the in situ formed acid chloride with the amine XIV in the same solvent at room temperature overnight.

Step C:

Cleavage of the amino protecting group from derivatives XV can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred protecting group is the tert-butoxycarbonyl group. Preferred conditions are the use of HCl in dioxane for 2 to 17 hrs at 60° C. or the use of $CF_3COOH$ in dichloromethane at room temperature overnight.

Scheme 3

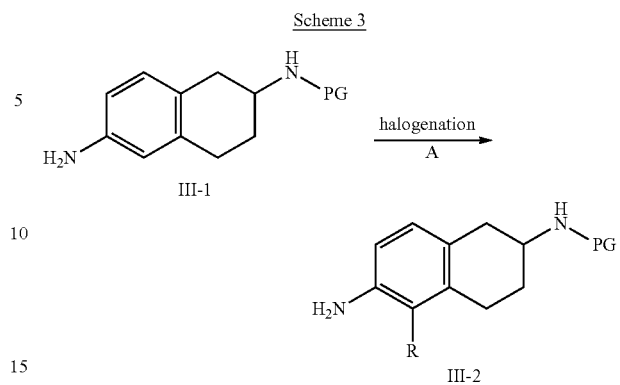

For R being halogen:
Step A:

Halogenation of the aniline III-1 can be accomplished by reaction with a suitable halogenation reagent such as N-chlorosuccinimide or N-bromosuccinimide in tetrachloromethane, chloroform or dimethylformamide at temperature from 0° C. to 75° C. for 15 min to 6 hrs.

Preferred conditions are the use of N-chlorosuccinimide in dimethylformamide at 60° C. for 1 h.

Scheme 4

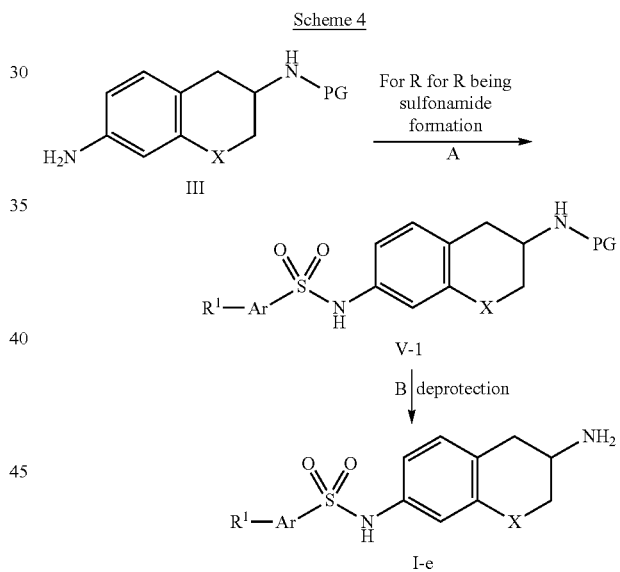

For R being hydrogen:
Step A:

Formation of sulfonamide V-1 can be accomplished by reaction of amine III with a sulfonylchloride in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine.

Preferred conditions are N,N-diisopropylethylamine, dioxane as solvent and heating to 60° C. for several hours.

Step B:

Cleavage of the amino protecting group from derivatives V-1 can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred protecting group is the tert-butoxycarbonyl group. Preferred conditions are the use of HCl in dioxane for 2 to 17 hrs at 60° C. or the use of CF₃COOH in dichloromethane at room temperature overnight.

The synthesis of the starting materials II (X=CH₂) is described in the scientific literature such as 1) Tschaen, David M.; Abramson, Lee; Cai, Dongwei; Desmond, Richard; Dolling, Ulf-H.; et al. *Journal of Organic Chemistry*, 1995, 60, 4324-4330 and others for the racemate or enantiomerically pure forms. Introduction of suitable protecting groups is described in various literature sources and is known to people skilled in the art. The tert-butyl carbamate (PG=Boc) group is a very useful group and can be introduced by treatment of the amine with di-tert-butyl dicarbonate with or without an additional base in an organic solvent or a mixture of an organic solvent and water.

The synthesis of the starting materials II (X=O) has been achieved for example according to the following scheme.

Step A:
Reaction of o-hydroxybenzaldehyde XVI with acrylonitrile and a suitable base such as 1,4-diaza-bicyclo[2.2.2]octane in an organic solvent or a mixture of water and an organic solvent.

Preferred conditions are the reaction with 1,4-diaza-bicyclo[2.2.2]octane in a mixture of chloroform and water at 90° C. for 36 hours.

Step B:
Reaction of nitrile XVII with a base such as lithium hydroxide, potassium hydroxide or sodium hydroxide in water or a mixture of water and an organic solvent such as tetrahydrofuran or methanol at room temperature or elevated temperatures.

Preferred conditions are the reaction with dilute sodium hydroxide solution in water at relux for 3 hours.

Step C:
Reduction of the unsaturated acid XVIII can be effected by hydrogenation with hydrogen under normal or elevated

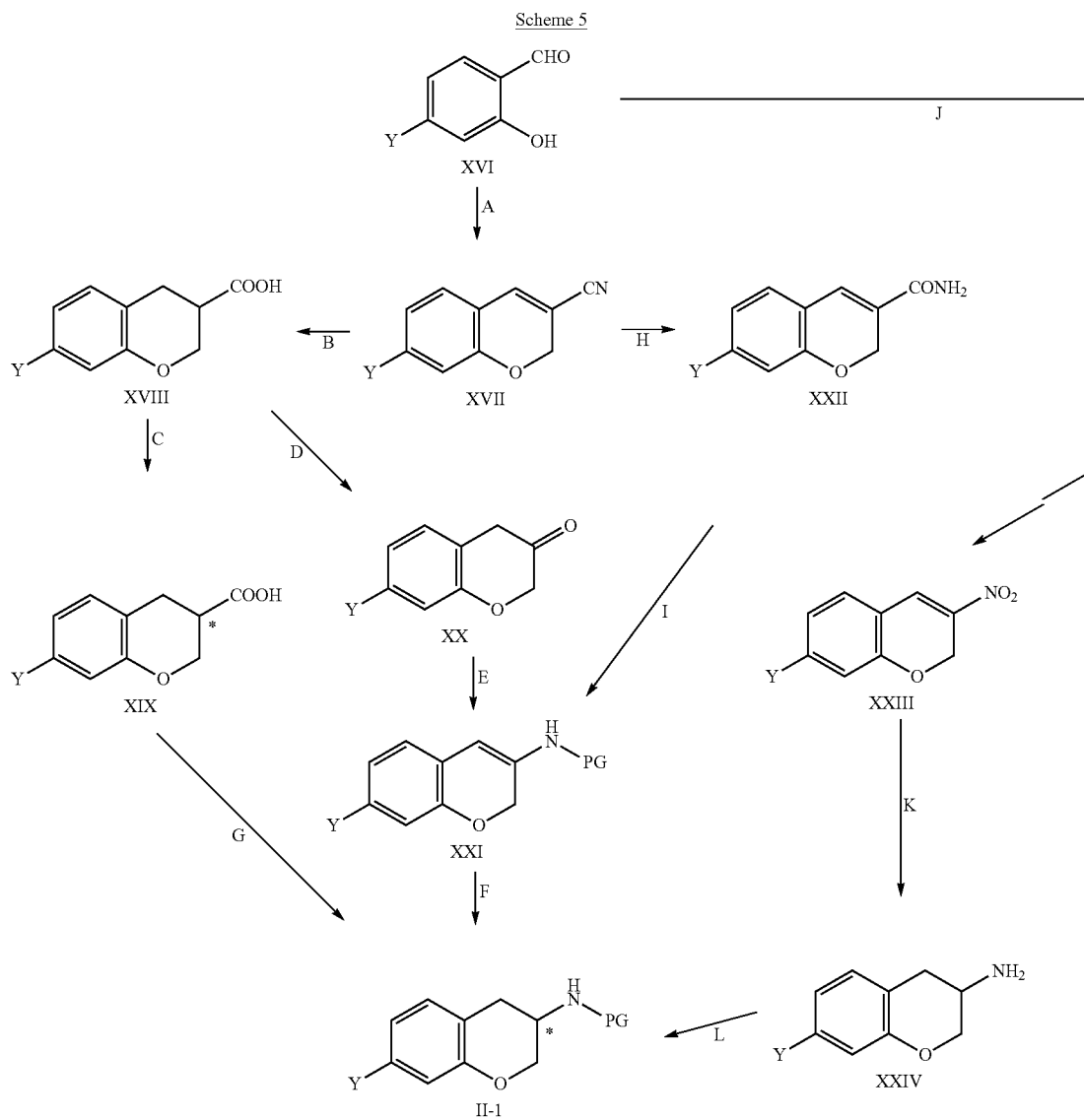

Scheme 5

(Y = Br, I)
*enantiomerically pure material may be obtained by the routes shown pressure with a catalyst such as PtO$_2$, Pd—C or Raney nickel in solvents such as MeOH, EtOH, H$_2$O, dioxane, THF, HOAc, EtOAc CH$_2$Cl$_2$, CHCl$_3$, DMF or mixtures thereof. Alternative catalysts can be soluble transition metal compounds such as ruthenium acetate or iridium cyclooctadiene complexes with and without a chiral ligand such as (R)- or (S)-(2,2'-bis(diphenylphosphino)-1,1'-binaphthyl) or derivatives thereof. Preferred conditions are the reaction with ruthenium acetate, (2,2'-bis(diphenylphosphino)-1,1'-binaphthyl) in methanol at 40° C. and 40 bar for 17 hours.

Step D:

Alternatively, the unsaturated acid XVIII can be transformed into the ketone XX by reaction with diphenylphosphoryl azide in presence of a base such as triethylamine or N,N-diisopropylethylamine in an organic solvent such as touene followed by acidic hydrolysis using hydrochloric acid, sulfuric acid, phosphoric acid or the like in water.

Preferred conditions are the reaction with diphenylphosphoryl azide and triethylamine in toluene at 85° C. for 12 h followed by treatment with 6 N hydrochlorid acid at 100° C. for 2 hours.

Step E:

Formation of compound XXI can be achieved by reacting ketone XX with a compound PG-NH$_2$ with PG=benzoyl, acetyl, propionyl or the like in an organic solvent such as toluene catalysed by a mineral acid or an acidic ion exchange resin.

Preferred conditions are the reaction with benzamide and ion exchange resin Amberlyst 15 in toluene at 110° C. for 24 hours.

Step F:

Reduction of compound XXI can be effected by hydrogenation with hydrogen under normal or elevated pressure with a catalyst such as PtO$_2$, Pd—C or Raney nickel in solvents such as MeOH, EtOH, H$_2$O, dioxane, THF, HOAc, EtOAc CH$_2$Cl$_2$, CHCl$_3$, DMF or mixtures thereof. Alternative catalysts can be soluble transition metal compounds such as ruthenium acetate or iridium cyclooctadiene complexes with and without a chiral ligand such as (R)- or (S)-(2,2'-bis(diphenylphosphino)-1,1'-binaphthyl) or derivatives thereof.

Preferred conditions are the reaction with ruthenium acetate, (2,2'-bis(dip-tolylphosphino)-1,1'-binaphthyl) in methanol at 25° C. and 20 bar for 4 hours.

Step G:

The acid XIX can be transformed into amino compound II-1 by reaction with diphenylphosphoryl azide in the presence of an alcohol such as methanol, ethanol or tert.-butanol. Preferred conditions are the reaction with diphenylphosphoryl azide in tert.-butanol at 80° C. for 6 hours.

Step H:

The nitrile XVII can be transformed into the amide XXII by reaction with an acid or a mixture of acids without water being present followed by an aqueous work-up.

Preferred conditions are the reaction with sulfuric acid and acetic acid at 100° C. for 1 hours followed by an aqueous work-up.

Step I:

The amide XXII can be transformed into the amide XXI by reaction with an oxidant such as aqueous sodium hypochlorite solution, sodium hypobromite solution or a mixture of a halogen and an aqueous base or a mixture of a halogen source such as N-bromosuccinimide or N-chlorosuccinimide and a base with or without an additional organic solvent such as methanol. Preferred conditions are the reaction with aqueous hypochlorite solution and methanol at 70° C. for 30 min.

Step J:

The hydroxyaldehyde XVI can be transformed into the nitro compound XXIII by reaction with 2-nitroethanol and a suitable base such as di-n-butylammonium chloride in an organic solvent such as butyl acetate, amyl acetate or isoamyl acetate.

Preferred conditions are the reaction with 2-nitroethanol and di-n-butylammonium chloride in isoamyl acetate 100° C. for 8 hours.

Step K:

Reduction of the nitro compound XXIII can be achieved by reaction with complex aluminum hydrides or boron hydride reagents such as lithium aluminium hydride or borane or mixtures of borane and borohydride reagents in ethereal solvents such as diethyl ether, dioxane, THF, DME or TBME.

Preferred condition are the reduction with a mixture of borane tetrahydrofuran complex and sodium borohydride in tetrahydrofuran at 65° C. for 18 hours.

Step L:

Transformation of amine XXIV to compound II-1 can be achieved by reaction with a variety of protecting group reagents known to people skilled in the art. Suitable protecting groups for the nitrogen atom are amides or carbamates. The tert-butyl carbamate (Boc) group is a very useful group and can be introduced by treatment of the amine with di-tert-butyl dicarbonate with or without an additional base in an organic solvent or a mixture of an organic solvent and water.

Preferred conditions are the reaction with di-tert-butyl dicarbonate and N,N-diisopropylethylamine in dichloromethane at room temperature for 18 hours.

Example 1

N-(6-Amino-5,6,7,8-tetrahydronaphthalen-2-yl)-2-(trifluoromethyl)isonicotinamide

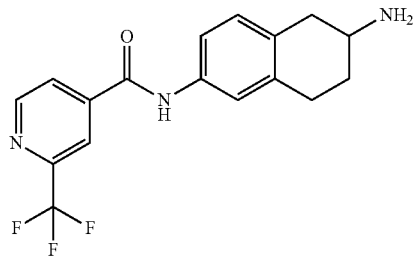 [SMILES: NC1CCc2cc(NC(=O)c3ccnc(C(F)(F)F)c3)ccc2C1]

a) 6-Bromo-1,2,3,4-tetrahydronaphthalen-2-amine

6-Bromo-3,4-dihydronaphthalen-2(1H)-one (5 g, 22.2 mmol) was combined with ammonium acetate (13.7 g, 178 mmol), sodium cyanoborohydride (1.68 g, 26.7 mmol) and methanol (250 ml) and stirred at room temperature. The reaction mixture was acidified with 2M aqueous hydrochloric acid, stirred for 10 min and the methanol was evaporated. The mixture was extracted with dichloromethane twice, the aqueous layer was basified with 1 N sodium hydroxide solution to pH 10, then extracted with dichloromethane twice. The organic extracts were dried over magnesium sulfate, filtered and concentrated in vacuo to yield a brown oil (3.05 g, 61%) which was used directly for the next step.

b) tert-Butyl 6-bromo-1,2,3,4-tetrahydronaphthalen-2-ylcarbamate

Di-tert-butyl dicarbonate (2.89 g, 13.2 mmol) was added to a solution of 6-bromo-1,2,3,4-tetrahydronaphthalen-2-amine (2.99 g, 13.2 mmol), diisopropylethylamine (2.56 g, 3.4 ml, 19.8 mmol) in dichloromethane (44 ml) at room temperature. The mixture was stirred overnight and the solvent was evaporated under reduced pressure. The residue was extracted with ethyl acetate and washed with 1 N aqueous hydrochloric acid, saturated sodium bicarbonate solution and brine, then dried with magnesium sulfate, filtered and concentrated under reduced pressure. The crude material was purified by flash chromatography (silica gel, 50 g, 10% to 30% ethyl acetate in heptane) to yield a dark brown solid (3.6 g, 83.5%), 1H NMR (300 MHz, CDCl3) δ ppm: 7.23 (m, 2H), 6.92 (d, 1H, J=8.3 Hz), 4.54 (b, 1H), 3.94 (m, 1H); 3.05 (dd, 1H; J=16.3/5.0 Hz), 2.85 (m, 2H), 2.55 (dd, 1H; J=16.3/8.4 Hz), 2.03 (m, 1H); 1.74 (m, 1H); 1.45 (m, 9H).

c) tert-Butyl 6-(diphenylmethyleneamino)-1,2,3,4-tetrahydronaphthalen-2-ylcarbamate tert-Butyl 6-bromo-1,2,3,4-tetrahydronaphthalen-2-ylcarbamate (3.58 g, 11.0 mmol) was combined with toluene (14.9 ml) to give a colourless solution. Diphenylmethanimine (2.19 g, 2.03 ml, 12.1 mmol) and sodium tert.-butoxide (1.69 g, 17.6 mmol) were added. The reaction mixture was degassed by bubbling argon into the mixture for several minutes. 2,2-Bis(diphenylphosphino)-1,1-binaphthalene (BINAP, 683 mg, 1.1 mmol) and tris(dibenzylideneacetone)dipalladium (Pd2(dba)3, 301 mg, 0.329 mmol) were added. The reaction mixture was stirred for 3 h at 90° C. The reaction mixture was filtered and concentrated in vacuo. The crude material was purified by flash chromatography (silica gel, 120 g, 10% to 30% ethyl acetate in heptane) to yield a yellow solid (3.27 g, 70%). MS (ISP): 427.4 ([M+H]$^+$).

d) tert-Butyl 6-amino-1,2,3,4-tetrahydronaphthalen-2-ylcarbamate tert-Butyl 6-(diphenylmethyleneamino)-1,2,3,4-tetrahydronaphthalen-2-ylcarbamate (3.27 g, 7.67 mmol) was combined with methanol (31.2 ml). Sodium acetate (1.89 g, 23.0 mmol) and hydroxylamine hydrochloride (1.17 g, 16.9 mmol) were added. The reaction mixture was stirred at 50° C. overnight. The reaction mixture was filtered through a sintered glass funnel. The filtrate was concentrated in vacuo. The crude material was purified by flash chromatography (silica gel, heptane/ethyl acetate, 3:2) to yield a white solid (1.81 g, 90%). MS (ISP): 207.1 ([M−tBu+H]$^+$).

e) tert-Butyl 6-(2-(trifluoromethyl)isonicotinamido)-1,2,3,4-tetrahydronaphthalen-2-ylcarbamate In a sealed tube, tert-butyl 6-amino-1,2,3,4-tetrahydronaphthalen-2-ylcarbamate (100 mg, 0.381 mmol) and 2-(trifluoromethyl)isonicotinic acid (80.1 mg, 0.419 mmol) were combined with tetrahydrofurane (2.1 ml). O-(Benzotriazol-1-yl)-N,N,N,N-tetramethyluronium tetrafluoroborate (TBTU, 245 mg, 0.762 mmol) and N-methylmorpholine (154 mg, 168 µl, 1.52 mmol) were added and the reaction mixture was shaken at 60° C. for 17 h. Ethyl acetate and water were added. The organic layer was dried over magnesium sulfate and evaporated. The crude material was purified by flash chromatography (silica gel, 10 g, 5% to 30% ethyl acetate in heptane) to yield a white solid (142 mg, 86%). MS (ISP): 380.2 ([M−tBu+H]$^+$).

f) N-(6-Amino-5,6,7,8-tetrahydronaphthalen-2-yl)-2-(trifluoromethyl)isonicotinamide hydrochloride tert-Butyl 6-(2-(trifluoromethyl)isonicotinamido)-1,2,3,4-tetrahydronaphthalen-2-ylcarbamate (139.2 mg, 0.32 mmol) was dissolved in dioxane (1.23 ml) and a 4 M solution of hydrogen chloride in dioxane (1.2 ml, 4.8 mmol) was added. The clear reaction mixture was shaken at 60° C. for 2 hours. The dioxane was removed under reduced pressure and diethyl ether was added. The solid was filtered and washed with more diethyl ether and then was dried under high vacuum. N-(6-Amino-5,6,7,8-tetrahydronaphthalen-2-yl)-2-(trifluoromethyl)isonicotinamide was obtained as hydrochloride salt, white solid (114 mg, 87%). MS (ISP): 336.2 ([M+H]$^+$).

Example 2

N-(6-Amino-5,6,7,8-tetrahydronaphthalen-2-yl)-4-bromo-5-cyclopropyl-1H-pyrazole-3-carboxamide

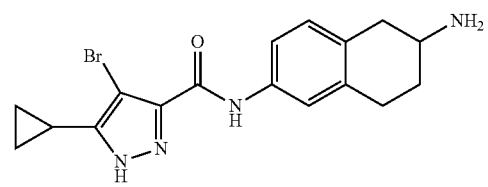 [SMILES: NC1CCc2cc(NC(=O)c3n[nH]c(C4CC4)c3Br)ccc2C1]

The title compound was obtained in analogy to Example 1 using 4-bromo-5-cyclopropyl-1H-pyrazole-3-carboxylic acid instead of 2-(trifluoromethyl)isonicotinic acid in step e). White solid, as hydrochloride salt. MS (ISP): 373.2 ({$^{79}$Br} [M+H]$^+$), 375.1 ({$^{81}$Br} [M+H]$^+$).

Example 3

N-(6-Amino-5,6,7,8-tetrahydronaphthalen-2-yl)-1-(2,2-difluoroethyl)-5-propyl-1H-pyrazole-3-carboxamide

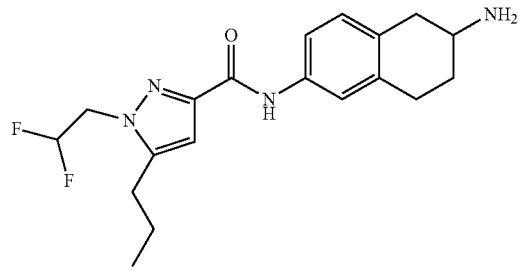 [SMILES: CCCc1cc(C(=O)Nc2ccc3c(c2)CCC(N)C3)nn1CC(F)F]

a) Ethyl 1-(2,2-difluoroethyl)-5-propyl-1H-pyrazole-3-carboxylate

Ethyl 3-propyl-1H-pyrazole-5-carboxylate (1 g, 5.49 mmol) and potassium tert-butoxide (660 mg, 5.76 mmol) were combined with tetrahydrofuran (23.1 ml). After 10 min, 2,2-difluoroethyl trifluoromethanesulfonate (1.56 g, 968 µl, 7.13 mmol) was added. The reaction mixture was stirred at rt overnight. Water and ethyl acetate were added.

The organic layer was dried over magnesium sulfate, filtered and evaporated. The crude material was purified by flash chromatography (silica gel, 20 g, 0% to 30% Ethyl acetate in heptane) to yield a colourless liquid (1.02 g, 76%). MS (ISP): 247.1 ([M+H]$^+$).

b) 1-(2,2-Difluoro-ethyl)-5-propyl-1H-pyrazole-3-carboxylic acid

Ethyl 1-(2,2-difluoroethyl)-5-propyl-1H-pyrazole-3-carboxylate (1 g, 4.06 mmol) was dissolved in tetrahydrofuran (8.5 ml) and 1 M aqueous lithium hydroxide (4.9 ml, 4.87 mmol) was added. The reaction mixture was shaken at 60° C. overnight. After cooling, diethyl ether was added. The aqueous layer was separated, acidified by addition of 2 M aqueous hydrochloric acid and extracted with a mixture diethyl ether/ethyl acetate. The organic layer was dried over MgSO$_4$, filtered and evaporated to yield the crude acid as a white solid (870 mg, 98%). MS (ISP): 219.1 ([M+H]$^+$).

c) tert-Butyl 6-(1-(2,2-difluoroethyl)-5-propyl-1H-pyrazole-3-carboxamido-1,2,3,4-tetrahydronaphthalen-2-ylcarbamate Tert-butyl 6-amino-1,2,3,4-tetrahydronaphthalen-2-ylcarbamate (100 mg, 0.381 mmol) and 1-(2,2-difluoro-ethyl)-5-propyl-1H-pyrazole-3-carboxylic acid (91.5 mg, 0.419 mmol) were combined with tetrahydrofuran (2.1 ml). O-(Benzotriazol-1-yl)-N,N,N,N-tetramethyluronium tetrafluoroborate (TBTU, 245 mg, 0.762 mmol) and N-methylmorpholine (154 mg, 168 µl, 1.52 mmol) were added and the reaction mixture was shaken at 60° C. for 17 h. Ethyl acetate and water were added. The organic layer was dried over magnesium sulfate and evaporated. The crude material was purified by flash chromatography (silica gel, 10 g, 5% to 30% ethyl acetate in heptane) to yield a white solid (152 mg, 86%). MS (ISP): 407.3 ([M–tBu+H]$^+$).

d) N-(6-Amino-5,6,7,8-tetrahydronaphthalen-2-yl)-1-(2,2-difluoroethyl)-5-propyl-1H-pyrazole-3-carboxamide hydrochloride Tert-butyl 6-(1-(2,2-difluoroethyl)-5-propyl-1H-pyrazole-3-carboxamido)-1,2,3,4-tetrahydronaphthalen-2-ylcarbamate (141.6 mg, 306 µmol) was dissolved in dioxane (1.2 ml) and a 4 M solution of hydrogen chloride in dioxane (1.15 ml, 4.59 mmol) was added. The clear reaction mixture was shaken at 60° C. for 2 hours. The dioxane was removed under reduced pressure and diethyl ether was added. The solid was filtered and washed with more diethyl ether and then was dried under high vacuum. The title compound was obtained as hydrochloride salt, white solid (121 mg, 99%). MS (ISP): 363.2 ([M+H]$^+$).

Example 4

(R)—N-(6-Amino-5,6,7,8-tetrahydronaphthalen-2-yl)-1-(2,2-difluoroethyl)-5-propyl-1H-pyrazole-3-carboxamide a) (S)-tert-Butyl 6-amino-1,2,3,4-tetrahydronaphthalen-2-ylcarbamate and (R)-tert-Butyl 6-amino-1,2,3,4-tetrahydronaphthalen-2-ylcarbamate Racemic tert-butyl 6-amino-1,2,3,4-tetrahydronaphthalen-2-ylcarbamate (600 mg, preparation see Example 1) was separated on a chiral column (Lux Cellulose-2) into its enantiomers using a heptane/isopropanol gradient. The solvents were evaporated to yield the enantiomeric compounds. (S)-tert-Butyl 6-amino-1,2,3,4-tetrahydronaphthalen-2-ylcarbamate: retention time 6.8 min, 213 mg, off-white solid. (R)-tert-Butyl 6-amino-1,2,3,4-tetrahydronaphthalen-2-ylcarbamate: retention time 14.1 min, 223 mg, off-white solid.

b) (R)-tert-Butyl 6-(1-(2,2-difluoroethyl)-5-propyl-1H-pyrazole-3-carboxamido)-1,2,3,4-tetrahydronaphthalen-2-ylcarbamate In a sealed tube, (R)-tert-butyl 6-amino-1,2,3,4-tetrahydronaphthalen-2-ylcarbamate (65 mg, 0.248 mmol) and 1-(2,2-difluoroethyl)-5-propyl-1H-pyrazole-3-carboxylic acid (59.5 mg, 0.273 mmol) were combined with tetrahydrofuran (1.38 ml). O-(Benzotriazol-1-yl)-N,N,N,N-tetramethyluronium tetrafluoroborate (TBTU, 159 mg, 0.5 mmol) and N-methylmorpholine (100 mg, 109 µl, 0.991 mmol) were added. The reaction mixture was shaken at 60° C. for 17 h. Ethyl acetate and water were added. The organic layer was dried over magnesium sulfate and evaporated. The crude material was purified by flash chromatography (silica gel, 10 g, 10% to 30% ethyl acetate in heptane) to yield a white solid (92 mg, 80%). MS (ISP): 407.2 ([M–tBu+H]$^+$).

c) (R)—N-(6-Amino-5,6,7,8-tetrahydronaphthalen-2-yl)-1-(2,2-difluoroethyl)-5-propyl-1H-pyrazole-3-carboxamide hydrochloride (R)-tert-Butyl 6-(1-(2,2-difluoroethyl)-5-propyl-1H-pyrazole-3-carboxamido)-1,2,3,4-tetrahydronaphthalen-2-ylcarbamate (84.1 mg, 0.182 mmol) was dissolved in dioxane (0.7 ml) and a 4 M solution of hydrogen chloride in dioxane (682 µl, 2.73 mmol) was added. The clear reaction mixture was shaken at 60° C. for 2 hours. The dioxane was removed under reduced pressure and diethyl ether was added. The solid was filtered and washed with more diethyl ether and then was dried under high vacuum. (R)—N-(6-Amino-5,6,7,8-tetrahydronaphthalen-2-yl)-1-(2,2-difluoroethyl)-5-propyl-1H-pyrazole-3-carboxamide was obtained as hydrochloride salt, white solid (54 mg, 74%). MS (ISP): 363.2 ([M+H]$^+$).

Example 5

(S)—N-(6-Amino-5,6,7,8-tetrahydronaphthalen-2-yl)-1-(2,2-difluoroethyl)-5-propyl-1H-pyrazole-3-carboxamide

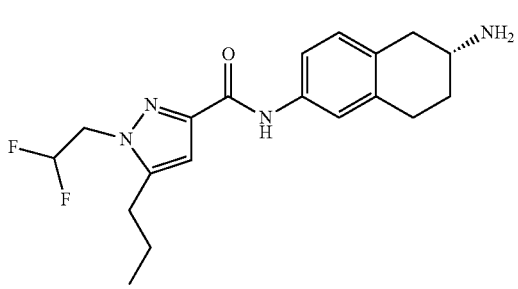 [SMILES: CCCc1cc(C(=O)Nc2ccc3c(c2)CC[C@@H](N)C3)nn1CC(F)F]

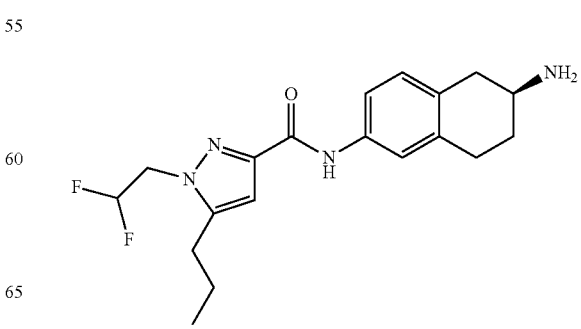

The title compound was obtained in analogy to Example 4 using (S)-tert-butyl 6-amino-1,2,3,4-tetrahydronaphthalen-2-ylcarbamate instead of (R)-tert-butyl 6-amino-1,2,3,4-tetrahydronaphthalen-2-ylcarbamate in step b). White solid, as hydrochloride salt. MS (ISP): 363.2 ([M+H]⁺).

Example 6

(R)—N-(6-Amino-5,6,7,8-tetrahydronaphthalen-2-yl)-6-methyl-2-(trifluoromethyl)-pyrimidine-4-carboxamide

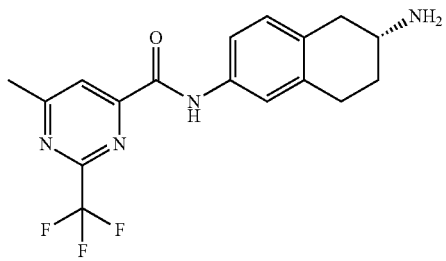

The title compound was obtained in analogy to Example 1 using 6-methyl-2-(trifluoromethyl)pyrimidine-4-carboxylic acid instead of 2-(trifluoromethyl)isonicotinic acid and (R)-tert-butyl 6-amino-1,2,3,4-tetrahydronaphthalen-2-ylcarbamate instead of tert-butyl 6-amino-1,2,3,4-tetrahydronaphthalen-2-ylcarbamate in step e). White solid, as hydrochloride salt. MS (ISP): 351.1 ([M+H]⁺).

Example 7

(S)—N-(6-Amino-5,6,7,8-tetrahydronaphthalen-2-yl)-6-methyl-2-(trifluoromethyl)-pyrimidine-4-carboxamide

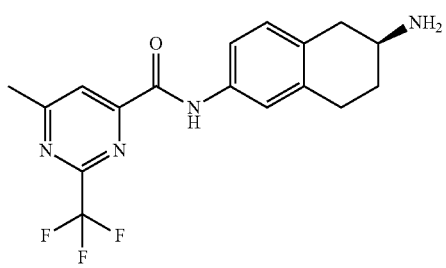 [SMILES: Cc1cc(C(=O)Nc2ccc3c(c2)CC[C@H](N)C3)nc(C(F)(F)F)n1]

The title compound was obtained in analogy to Example 1 using 6-methyl-2-(trifluoromethyl)pyrimidine-4-carboxylic acid instead of 2-(trifluoromethyl)isonicotinic acid and (S)-tert-butyl 6-amino-1,2,3,4-tetrahydronaphthalen-2-ylcarbamate instead of tert-butyl 6-amino-1,2,3,4-tetrahydronaphthalen-2-ylcarbamate in step e). White solid, as hydrochloride salt. MS (ISP): 351.1 ([M+H]⁺).

Example 8

N-(3-Aminochroman-7-yl)-1-(2,2-difluoroethyl)-5-propyl-1H-pyrazole-3-carboxamide

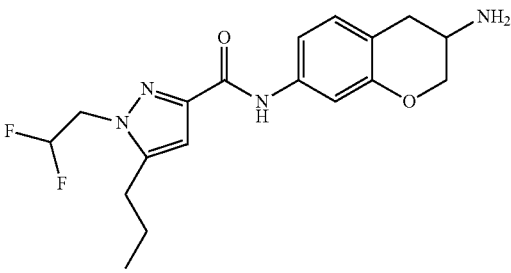

a) 7-Bromo-3-nitro-2H-chromene

A mixture of 4-bromo-2-hydroxybenzaldehyde (10 g, 49.8 mmol), dibutylamine hydrochloride (4.12 g, 24.9 mmol) and nitroethanol (9.06 g, 7.13 ml, 99.5 mmol) in amyl acetate (150 ml) was heated to reflux for 8 hours with continuous removal of water using a Dean-Stark apparatus under argon atmosphere. After cooling to room temperature a dark solid was filtered off and washed with ethyl acetate. The filtrate was evaporated under reduced pressure. The crude material was purified by flash chromatography (silica gel, 330 g, 2% to 30% ethyl acetate in heptane) to yield a yellow solid (6.13 g, 48%), 1H NMR (300 MHz, CDCl3) δ ppm: 7.74 (s, 1H), 7.09-7.18 (m, 3H), 5.25 (s, 2H).

b) 6-Bromo-1,2,3,4-tetrahydronaphthalen-2-amine

At 0° C. and under argon a solution of borane tetrahydrofuran complex (1M, 119 ml, 119 mmol) was added dropwise to a solution of 7-bromo-3-nitro-2H-chromene (6.1 g, 23.8 mmol) in tetrahydrofuran (103 ml). After addition the ice bath was removed. Sodium borohydride (0.9 g, 23.8 mmol) was added and the reaction was allowed to stir for 18 h at 65° C. The reaction mixture was cooled to room temperature and poured into a 2 M solution of hydrochloric acid. After stirring for 1.5 h at 70° C. the mixture was cooled to room temperature and extracted twice with diethyl ether. The aqueous layer was basified with 2 N sodium hydroxide solution to pH 10, then extracted three times with ethyl acetate. The combined organic extracts were dried over magnesium sulfate, filtered and concentrated in vacuum to yield a light brown solid (3.68 g, 68%). MS (ISP): 228.0 ({⁷⁹Br} [M+H]⁺), 230.0 ({⁸¹Br} [M+H]⁺).

c) tert-Butyl 6-bromo-1,2,3,4-tetrahydronaphthalen-2-ylcarbamate

Di-tert-butyl dicarbonate (3.44 g, 15.8 mmol) was added to a solution of 7-bromochroman-3-amine (3.6 g, 15.8 mmol), diisopropylethylamine (3.06 g, 4.05 ml, 23.7 mmol) in dichloromethane (53 ml) at room temperature. The mixture was stirred overnight and the solvent was evaporated under reduced pressure. The residue was extracted with ethyl acetate and washed with 1 N aqueous hydrochloric acid, saturated sodium bicarbonate solution and brine, then dried with magnesium sulfate, filtered and concentrated under reduced pressure. The crude material was purified by flash chromatography (silica gel, 50 g, 10% to 30% ethyl acetate in heptane) to yield a white solid (4.47 g, 86.3%), MS (ISP): 272.0 ({$^{79}$Br} [M−tBu+H]$^+$), 274.0 ({$^{81}$Br} [M−tBu+H]$^+$).

d) tert-Butyl 7-(diphenylmethyleneamino)chroman-3-ylcarbamate tert-Butyl 7-bromochroman-3-ylcarbamate (4.43 g, 13.5 mmol) was combined with toluene (18.3 ml) to give a colourless solution. Diphenylmethanimine (2.69 g, 2.49 ml, 14.8 mmol) and sodium tert.-butoxide (2.08 g, 21.6 mmol) were added. The reaction mixture was degassed by bubbling argon into the mixture for several minutes. 2,2-Bis(diphenylphosphino)-1,1-binaphthalene (BINAP, 840 mg, 1.35 mmol) and tris(dibenzylideneacetone)dipalladium (Pd2(dba)3, 371 mg, 0.405 mmol) were added. The reaction mixture was stirred for 3 h at 90° C. The reaction mixture was filtered and concentrated in vacuo. The crude material was purified by flash chromatography (silica gel, 120 g, 10% to 30% ethyl acetate in heptane) to yield an orange solid (2.69 g, 46%). MS (ISP): 429.2 ([M+H]$^+$).

e) tert-Butyl 7-aminochroman-3-ylcarbamate tert-Butyl 7-(diphenylmethyleneamino)chroman-3-ylcarbamate (2.65 g, 6.18 mmol) was combined with methanol (25 ml). Sodium acetate (1.52 g, 18.6 mmol) and hydroxylamine hydrochloride (0.945 g, 13.6 mmol) were added. The reaction mixture was stirred at 50° C. overnight. The reaction mixture was filtered through a sintered glass funnel. The filtrate was concentrated in vacuo. The crude material was purified by flash chromatography (silica gel, heptane/ethyl acetate, 3:2) to yield a light yellow foam (1.6 g, 98%). MS (ISP): 209.1 ([M−tBu+H]$^+$).

f) tert-Butyl 7-(1-(2,2-difluoroethyl)-5-propyl-1H-pyrazole-3-carboxamido)chroman-3-ylcarbamate In a sealed tube, tert-butyl 7-aminochroman-3-ylcarbamate (100 mg, 0.378 mmol) and 1-(2,2-difluoroethyl)-5-propyl-1H-pyrazole-3-carboxylic acid (90.8 mg, 0.416 mmol) were combined with tetrahydrofuran (2.1 ml). O-(Benzotriazol-1-yl)-N,N,N,N-tetramethyluronium tetrafluoroborate (TBTU, 243 mg, 0.757 mmol) and N-methylmorpholine (153 mg, 166 μl, 1.51 mmol) were added and the reaction mixture was shaken at 60° C. for 17 h. Ethyl acetate and water were added. The organic layer was dried over magnesium sulfate and evaporated. The crude material was purified by flash chromatography (silica gel, 10 g, 10% to 30% ethyl acetate in heptane) to yield a light yellow solid (144 mg, 82%). MS (ISP): 409.2 ([M−tBu+H]$^+$).

g) N-(3-Aminochroman-7-yl)-1-(2,2-difluoroethyl)-5-propyl-1H-pyrazole-3-carboxamide hydrochloride tert-Butyl 7-(1-(2,2-difluoroethyl)-5-propyl-1H-pyrazole-3-carboxamido)chroman-3-ylcarbamate (141 mg, 0.3 mmol) was dissolved in dioxane (1.17 ml) and a 4 M solution of hydrogen chloride in dioxane (1.14 ml, 4.55 mmol) was added. The clear reaction mixture was shaken at 60° C. for 2 hours. The dioxane was removed under reduced pressure and diethyl ether was added. The solid was filtered and washed with more diethyl ether and then was dried under high vacuum. N-(3-Aminochroman-7-yl)-1-(2,2-difluoroethyl)-5-propyl-1H-pyrazole-3-carboxamide was obtained as hydrochloride salt, light yellow solid (96 mg, 79%). MS (ISP): 365.2 ([M+H]$^+$).

Example 9

N-(3-Aminochroman-7-yl)-6-methyl-2-(trifluoromethyl)pyrimidine-4-carboxamide

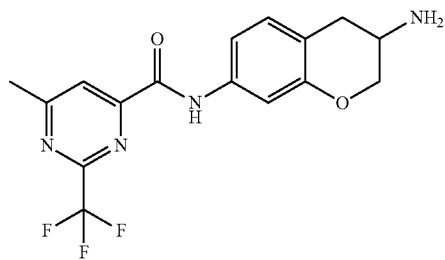 [SMILES: Cc1cc(C(=O)Nc2ccc3c(c2)OCC(N)C3)nc(C(F)(F)F)n1]

The title compound was obtained in analogy to Example 8 using 6-methyl-2-(trifluoromethyl)pyrimidine-4-carboxylic acid instead of 1-(2,2-difluoroethyl)-5-propyl-1H-pyrazole-3-carboxylic acid in step f). Light yellow solid, as hydrochloride salt. MS (ISP): 353.1 ([M+H]$^+$).

Example 10

(R)—N-(3-Aminochroman-7-yl)-1-(2,2-difluoroethyl)-5-propyl-1H-pyrazole-3-carboxamide

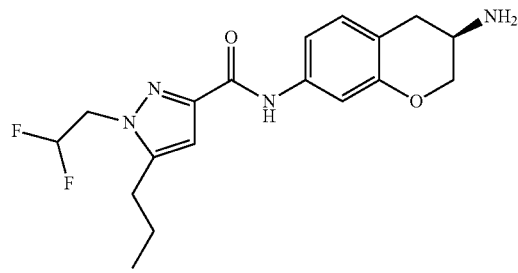

a) (S)-tert-butyl 7-aminochroman-3-ylcarbamate and (R)-tert-butyl 7-aminochroman-3-ylcarbamate Racemic tert-butyl 7-aminochroman-3-ylcarbamate (1250 mg, preparation see Example 10) was separated on a Lux Amylose chiral column into its enantiomers using a heptane/isopropanol gradient. The solvents were evaporated to yield the enantiomeric compounds. (R)-tert-Butyl 6-amino-1,2,3,4-tetrahydronaphthalen-2-ylcarbamate: retention time 12.3 min, 545 mg, off-white solid. (S)-tert-Butyl 6-amino-1,2,3,4-tetrahydronaphthalen-2-ylcarbamate: retention time 14.0 min, 589 mg, light yellow solid.

b) (R)-tert-Butyl 7-(1-(2,2-difluoroethyl)-5-propyl-1H-pyrazole-3-carboxamido)chroman-3-ylcarbamate In a sealed tube, (R)-tert-butyl 7-aminochroman-3-ylcarbamate (100 mg, 0.38 mmol) and 1-(2,2-difluoroethyl)-5-propyl-1H-pyrazole-3-carboxylic acid (91 mg, 0.415 mmol) were combined with tetrahydrofuran (2.1 ml). O-(Benzotriazol-1-yl)-N,N,N,N-tetramethyluronium tetrafluoroborate (TBTU, 243 mg, 0.76 mmol) and N-methylmorpholine (153 mg, 165 μl, 1.5 mmol) were added. The reaction mixture was shaken at 60° C. for 17 h. Ethyl acetate and water were added. The organic layer was dried over magnesium sulfate and evaporated. The crude material was purified by flash chromatography (silica gel, 10 g, 10% to 30% ethyl acetate in heptane) to yield a white solid (92 mg, 80%). MS (ISP): 409.2 ([M−tBu+H]$^+$).

c) (R)—N-(3-Aminochroman-7-yl)-1-(2,2-difluoroethyl)-5-propyl-1H-pyrazole-3-carboxamide hydrochloride (R)-tert-Butyl 7-(1-(2,2-difluoroethyl)-5-propyl-1H-pyrazole-3-carboxamido)chroman-3-ylcarbamate (42.7 mg, 0.092 mmol) was dissolved in dioxane (0.35 ml) and a 4 M solution of hydrogen chloride in dioxane (345 μl, 1.38 mmol) was added. The clear reaction mixture was shaken at 60° C. for 2 hours. The dioxane was removed under reduced pressure and diethyl ether was added. The solid was filtered and washed with more diethyl ether and then was dried under high vacuum. (R)—N—)—N-(3-Aminochroman-7-yl)-1-(2,2-difluoroethyl)-5-propyl-1H-pyrazole-3-carboxamide was obtained as hydrochloride salt, off-white powder (25 mg, 68%). MS (ISP): 365.2 ([M+H]$^+$).

Example 11

(S)—N-(3-Aminochroman-7-yl)-1-(2,2-difluoroethyl)-5-propyl-1H-pyrazole-3-carboxamide

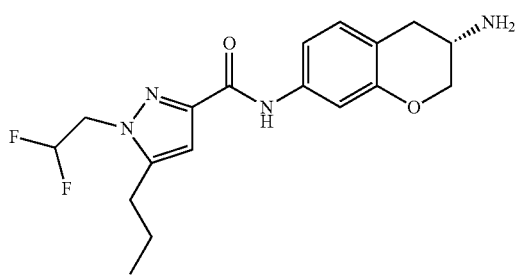

The title compound was obtained in analogy to Example 10 using (S)-tert-butyl 6-amino-1,2,3,4-tetrahydronaphthalen-2-ylcarbamate instead of (R)-tert-butyl 6-amino-1,2,3,4-tetrahydronaphthalen-2-ylcarbamate in step b). Off-white powder, as hydrochloride salt. MS (ISP): 365.2 ([M+H]$^+$).

Example 12

(R)—N-(3-Aminochroman-7-yl)-6-methyl-2-(trifluoromethyl)pyrimidine-4-carboxamide

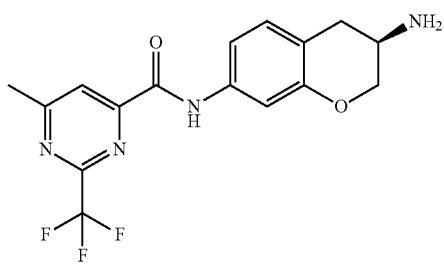 [SMILES: Cc1cc(C(=O)Nc2ccc3c(c2)OC[C@H](N)C3)nc(C(F)(F)F)n1]

The title compound was obtained in analogy to Example 10 using 6-methyl-2-(trifluoromethyl)pyrimidine-4-carboxylic acid instead of 1-(2,2-difluoroethyl)-5-propyl-1H-pyrazole-3-carboxylic acid in step b). Light yellow solid, as hydrochloride salt. MS (ISP): 353.1 ([M+H]$^+$).

Example 13

(S)—N-(3-Aminochroman-7-yl)-6-methyl-2-(trifluoromethyl)pyrimidine-4-carboxamide

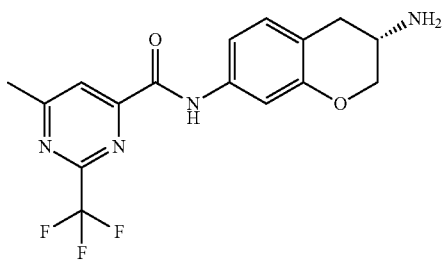 [SMILES: Cc1cc(C(=O)Nc2ccc3c(c2)OC[C@@H](N)C3)nc(C(F)(F)F)n1]

The title compound was obtained in analogy to Example 10 using 6-methyl-2-(trifluoromethyl)pyrimidine-4-carboxylic acid instead of 1-(2,2-difluoroethyl)-5-propyl-1H-pyrazole-3-carboxylic acid and (S)-tert-butyl 6-amino-1,2,3,4-tetrahydronaphthalen-2-ylcarbamate instead of (R)-tert-butyl 6-amino-1,2,3,4-tetrahydronaphthalen-2-ylcarbamate in step b). Light yellow solid, as hydrochloride salt. MS (ISP): 353.1 ([M+H]$^+$).

Example 14

(R)—N-(6-Amino-5,6,7,8-tetrahydronaphthalen-2-yl)-4-chlorobenzamide

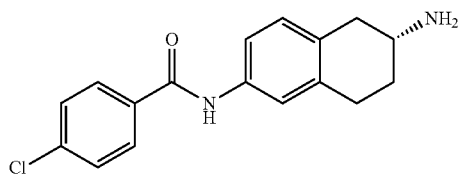 [SMILES: N[C@@H]1CCc2cc(NC(=O)c3ccc(Cl)cc3)ccc2C1]

The title compound was obtained in analogy to Example 1 using 4-chlorobenzoic acid instead of 2-(trifluoromethyl)isonicotinic acid and (R)-tert-butyl 6-amino-1,2,3,4-tetrahydronaphthalen-2-ylcarbamate instead of tert-butyl 6-amino-1,2,3,4-tetrahydronaphthalen-2-ylcarbamate in step e). Light brown solid, as hydrochloride salt. MS (ISP): 301.1 ($\{^{35}Cl\}$ [M+H]$^+$), 303.1 ($\{^{37}Cl\}$[M+H]$^+$).

Example 15

(R)—N-(6-Amino-5,6,7,8-tetrahydronaphthalen-2-yl)-2-chlorobenzamide

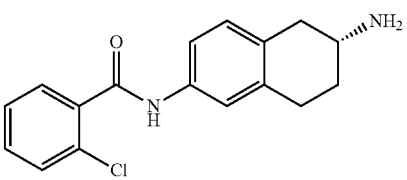 [SMILES: N[C@@H]1CCc2cc(NC(=O)c3ccccc3Cl)ccc2C1]

The title compound was obtained in analogy to Example 1 using 2-chlorobenzoic acid instead of 2-(trifluoromethyl)isonicotinic acid and (R)-tert-butyl 6-amino-1,2,3,4-tetrahydronaphthalen-2-ylcarbamate instead of tert-butyl 6-amino-1,2,3,4-tetrahydronaphthalen-2-ylcarbamate in step e). Light brown solid, as hydrochloride salt. MS (ISP): 301.1 ({$^{35}$Cl} [M+H]$^+$), 303.1 ({$^{37}$Cl}[M+H]$^+$).

Example 16

(S)-1-(6-Amino-5,6,7,8-tetrahydronaphthalen-2-yl)-3-(6-(trifluoromethyl)pyridin-3-yl)urea

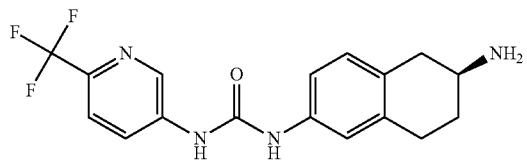 [SMILES: N[C@H]1CCc2cc(NC(=O)Nc3ccc(C(F)(F)F)nc3)ccc2C1]

a) (S)-tert-Butyl 6-(3-(6-(trifluoromethyl)pyridin-3-yl)ureido)-1,2,3,4-tetrahydronaphthalen-2-ylcarbamate In a 25 mL round-bottomed flask, (S)-tert-butyl 6-amino-1,2,3,4-tetrahydronaphthalen-2-ylcarbamate (70 mg, 0.267 mmol) was dissolved in dichloroethane (2 ml). Triethylamine (54 mg, 74.4 μl, 0.534 mmol) was added. The reaction mixture was cooled to 0° C. and triphosgene (29.3 mg, 0.1 mmol) was added. After stirring the mixture at room temperature for 1 h, 6-(trifluoromethyl)pyridin-3-amine (43.3 mg, 0.267 mmol) was added. The reaction mixture was stirred at room temperature overnight. The crude material was purified by flash chromatography (silica gel, 50 g, 0% to 80% Ethyl acetate in hexanes) to yield an off-white solid (23 mg, 19%). MS (ISP): 395.2 ([M−tBu+H]$^+$).

b) (S)-1-(6-Amino-5,6,7,8-tetrahydronaphthalen-2-yl)-3-(6-(trifluoromethyl)pyridin-3-yl)urea In a sealed tube, (S)-tert-butyl 6-(3-(6-(trifluoromethyl)pyridin-3-yl)ureido)-1,2,3,4-tetrahydronaphthalen-2-ylcarbamate (23 mg, 0.051 mmol) was combined with dioxane (1 ml) to give a yellow solution. A solution of hydrochloric acid in dioxane (4M, 0.19 ml, 0.766 mmol) was added and the solution was shaken at 60° C. overnight. The reaction mixture was concentrated in vacuo and diethyl ether was added. The solid was separated by filtration through sintered glass and dried in vacuo. (S)-1-(6-Amino-5,6,7,8-tetrahydronaphthalen-2-yl)-3-(6-(trifluoromethyl)-pyridin-3-yl)urea was obtained as hydrochloride salt, yellow solid (12 mg, 61%). MS (ISP): 351.1 ([M+H]$^+$).

Example 17

(S)—N-(6-Amino-5,6,7,8-tetrahydronaphthalen-2-yl)-2-methylisonicotinamide

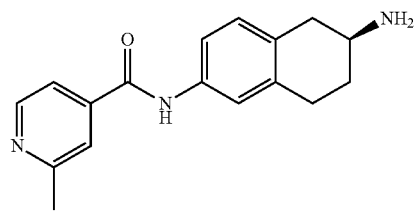 [SMILES: Cc1cc(C(=O)Nc2ccc3c(c2)CC[C@H](N)C3)ccn1]

The title compound was obtained in analogy to Example 1 using 2-methylisonicotinic acid instead of 2-(trifluoromethyl)isonicotinic acid and (S)-tert-butyl 6-amino-1,2,3,4-tetrahydronaphthalen-2-ylcarbamate instead of tert-butyl 6-amino-1,2,3,4-tetrahydronaphthalen-2-ylcarbamate in step e). Yellow solid, as hydrochloride salt. MS (ISP): 282.2 ([M+H]$^+$).

Example 18

(S)-2-Acetamido-N-(6-amino-5,6,7,8-tetrahydronaphthalen-2-yl)isonicotinamide

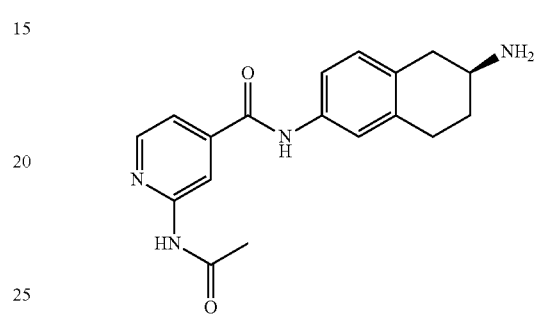

The title compound was obtained in analogy to Example 1 using 2-acetamidoisonicotinic acid instead of 2-(trifluoromethyl)isonicotinic acid and (S)-tert-butyl 6-amino-1,2,3,4-tetrahydronaphthalen-2-ylcarbamate instead of tert-butyl 6-amino-1,2,3,4-tetrahydronaphthalen-2-ylcarbamate in step e). Yellow solid, as hydrochloride salt. MS (ISP): 325.2 ([M+H]$^+$).

Example 19

(S)—N-(6-Amino-5,6,7,8-tetrahydronaphthalen-2-yl)-2-ethoxyisonicotinamide

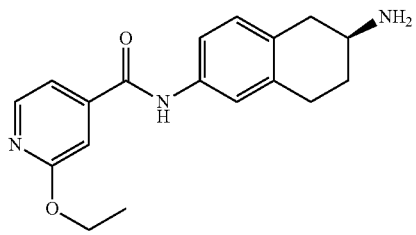 [SMILES: CCOc1cc(C(=O)Nc2ccc3c(c2)CC[C@H](N)C3)ccn1]

a) N-(6-Bromo-3,4-dihydronaphthalen-2-yl)benzamide

To a solution of 6-bromo-3,4-dihydronaphthalen-2(1H)-one (10 g, 44.4 mmol) and benzamide (13.5 g, 111 mmol) in toluene (50 ml) was added dry Amberlyst 15 resin (5 g). The mixture was heated to reflux for 30 hours with continuous removal of water using a Dean-Stark apparatus. The hot mixture was filtered, and the resin was washed with toluene and ethyl acetate. The filtrate was extracted with 1 N aqueous sodium bicarbonate and water. The organic layer was dried over magnesium sulfate and evaporated under reduced pressure. The crude material was purified by flash chromatography (silica gel, dichloromethane) to yield a b) (S)—N-(6-Bromo-1,2,3,4-tetrahydronaphthalen-2-yl)benzamide

In a glove box an autoclave was filled with N-(6-bromo-3,4-dihydronaphthalen-2-yl)benzamide (3.8 g, 11.5 mmol) and methanol (30 ml). A solution of diacetato[(R)-(−)-2,2-bis(ditolyl-phosphino)-1,1'-binaphthyl]ruthenium(II) (Ru(OAc)$_2$((R)-p-Tol-BINAP), 13.7 mg, 15.3 µmol) in methanol (5 ml) and sulfuric acid (234 mg, 128 µl, 2.29 mmol) were added. The mixture was hydrogenated at 10 bar H$_2$ atmosphere at room temperature for 4.5 hours. For work-up dichloromethane (60 ml) was added to give a green solution which was transferred to a round bottomed flask. The solvents were evaporated, but not to complete dryness. The solid formed was filtered and washed with cold methanol. The crude material was purified by flash chromatography (silica gel, 100 g, 10% to 30% ethyl acetate in heptane) to yield a brown solid (3.16 g, 83%), MS (ISP): 330.1 ({$^{79}$Br}[M+H]$^+$), 332.1 ({$^{81}$Br} [M+H]$^+$).

c) (S)-6-Bromo-1,2,3,4-tetrahydronaphthalen-2-amine

In an autoclave (S)—N-(6-bromo-1,2,3,4-tetrahydronaphthalen-2-yl)benzamide (3.9 g, 11.8 mmol) was suspended in water (6.6 ml). Methansulfonic acid (13.5 g, 9.1 ml, 140 mmol) and acetic acid (6.97 g, 6.64 ml, 116 mmol) were added. The autoclave was pressurized with 7 bar argon and shaken at 160° C. for 24 hours. After cooling the pH was adjusted to 12 by adding 1 N aqueous sodium hydroxide solution. The product was extracted twice with tert-butyl methyl ether. The organic layer was extracted with 1 N aqueous sodium hydroxide solution and brine. The organic layer was dried over magnesium sulfate, filtered and concentrated in vacuo to yield a brown oil that was used directly for the next step (2.59 g, 97%). MS (ISP): 226.0 ({$^{79}$Br}[M+H]$^+$), 228.0 ({$^{81}$Br} [M+H]$^+$).

d) (S)-tert-Butyl 6-bromo-1,2,3,4-tetrahydronaphthalen-2-ylcarbamate

The title compound was obtained in analogy to Example 1b using (S)-6-bromo-1,2,3,4-tetrahydronaphthalen-2-amine instead of 6-bromo-1,2,3,4-tetrahydronaphthalen-2-amine. Off-white solid. MS (ISP): 270.0 ({$^{79}$Br} [M+H]$^+$), 272.0 0 ({$^{81}$Br} [M+H]$^+$).

e) (S)-tert-Butyl 6-(diphenylmethyleneamino)-1,2,3,4-tetrahydronaphthalen-2-ylcarbamate The title compound was obtained in analogy to Example 1c using (S)-tert-butyl 6-bromo-1,2,3,4-tetrahydronaphthalen-2-ylcarbamate instead of tert-butyl 6-bromo-1,2,3,4-tetrahydronaphthalen-2-ylcarbamate. Yellow viscous oil. MS (ISP): 427.3 ([M+H]$^+$).

f) (S)-tert-Butyl 6-amino-1,2,3,4-tetrahydronaphthalen-2-ylcarbamate

The title compound was obtained in analogy to Example 1d using (S)-tert-Butyl 6-(diphenylmethyleneamino)-1,2,3,4-tetrahydronaphthalen-2-ylcarbamate instead of (S)-tert-Butyl 6-(diphenylmethyleneamino)-1,2,3,4-tetrahydronaphthalen-2-ylcarbamate. Off-white solid. MS (ISP): 207.1 ([M−tBu+H]$^+$).

g) (S)-tert-Butyl 6-(2-ethoxyisonicotinamido)-1,2,3,4-tetrahydronaphthalen-2-ylcarbamate Under argon 2-ethoxyisonicotinic acid (19 mg, 0.11 mmol) was suspended in dichloromethane (1 ml). 1-Chloro-N,N,2-trimethyl-1-propenylamine (19 mg, 19 µl, 0.14 mmol) was added dropwise and the reaction mixture was stirred for 30 minutes at room temperature to form the acid chloride. (S)-tert-Butyl 6-amino-1,2,3,4-tetrahydronaphthalen-2-ylcarbamate (30 mg, 0.11 mmol) was dissolved in dichloromethane (1 ml) and ethyldiisopropylamine (37 mg, 47 µl, 0.286 mmol) was added. To this solution the acid chloride solution was added dropwise and the reaction mixture was stirred at room temperature for 30 min. The reaction mixture was distributed between water and dichloromethane. The organic layer was dried over magnesium sulfate and evaporated. The crude material was purified by flash chromatography (silica gel, 12 g, 10% to 30% ethyl acetate in heptane) to yield a light yellow solid which was used for the next step (27 mg, 58%).

h) (S)—N-(6-Amino-5,6,7,8-tetrahydronaphthalen-2-yl)-2-ethoxyisonicotinamide hydrochloride (S)-tert-Butyl 6-(2-ethoxyisonicotinamido)-1,2,3,4-tetrahydronaphthalen-2-ylcarbamate (27 mg, 0.066 mmol) was dissolved in dioxane (0.3 ml) and a 4 M solution of hydrogen chloride in dioxane (0.32 ml, 1.28 mmol) was added. The clear reaction mixture was shaken at 60° C. for 2 hours. The dioxane was removed under reduced pressure and diethyl ether was added. The solid was filtered and washed with more diethyl ether and then was dried under high vacuum. (S)—N-(6-Amino-5,6,7,8-tetrahydronaphthalen-2-yl)-2-ethoxyisonicotinamide was obtained as hydrochloride salt, yellow solid (18 mg, 80%). MS (ISP): 312.2 ([M+H]$^+$).

Example 20

(S)—N-(6-Amino-5,6,7,8-tetrahydronaphthalen-2-yl)-6-(trifluoromethyl)nicotinamide

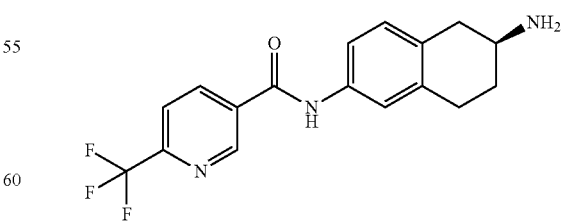

The title compound was obtained in analogy to Example 19 using 6-(trifluoromethyl)nicotinic acid instead of 2-ethoxyisonicotinic acid in step g). Light brown solid, as hydrochloride salt. MS (ISP): 336.1 ([M+H]$^+$).

Example 21

(S)—N-(6-Amino-5,6,7,8-tetrahydronaphthalen-2-yl)-6-methoxynicotinamide

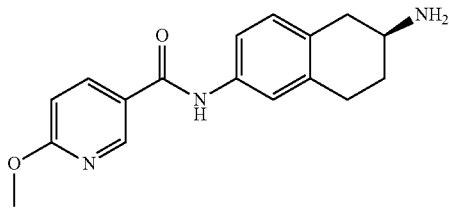 [SMILES: COc1ccc(C(=O)Nc2ccc3c(c2)CC[C@H](N)C3)cn1]

The title compound was obtained in analogy to Example 19 using 6-methoxynicotinic acid instead of 2-ethoxyisonicotinic acid in step g). Light brown solid, as hydrochloride salt. MS (ISP): 298.2 ([M+H]$^+$).

Example 22

(S)—N-(6-Amino-5,6,7,8-tetrahydronaphthalen-2-yl)-6-(2,2,2-trifluoroethoxy)nicotinamide

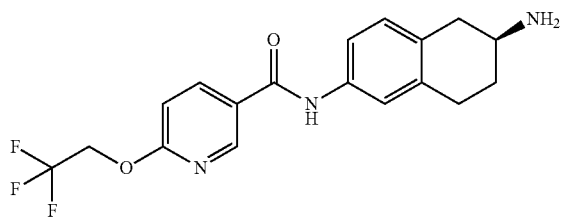 [SMILES: N[C@H]1CCc2cc(NC(=O)c3ccc(OCC(F)(F)F)nc3)ccc2C1]

The title compound was obtained in analogy to Example 19 using 6-(2,2,2-trifluoroethoxy)-nicotinic acid instead of 2-ethoxyisonicotinic acid in step g). Brown solid, as hydrochloride salt. MS (ISP): 364.3 ([M+H]$^+$).

Example 23

(S)—N6-(5-(Trifluoromethyl)pyrimidin-2-yl)-1,2,3,4-tetrahydronaphthalene-2,6-diamine

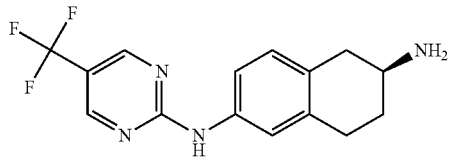 [SMILES: N[C@H]1CCc2cc(Nc3ncc(C(F)(F)F)cn3)ccc2C1]

a) (S)-tert-Butyl 6-(5-(trifluoromethyl)pyrimidin-2-ylamino)-1,2,3,4-tetrahydronaphthalen-2-ylcarbamate In a sealed tube, (S)-tert-butyl 6-amino-1,2,3,4-tetrahydronaphthalen-2-ylcarbamate (100 mg, 0.38 mmol), 2-chloro-5-(trifluoromethyl)pyrimidine (76.5 mg, 0.42 mmol) and diisopropyl ethylamine (78.8 mg, 0.107 ml, 0.610 mmol) were dissolved in 2-propanol (1 ml). The reaction mixture was capped and stirred for 5 h at 90° C. The crude material was purified by flash chromatography (silica gel, 50 g, 0% to 50% Ethyl acetate in hexanes) to yield a yellow solid (153 mg, 98%). MS (ISP): 353.1 ([M−tBu+H]$^+$).

b) (S)—N6-(5-(Trifluoromethyl)pyrimidin-2-yl)-1,2,3,4-tetrahydronaphthalene-2,6-diamine In a sealed tube, (S)-tert-butyl 6-(5-(trifluoromethyl)pyrimidin-2-ylamino)-1,2,3,4-tetrahydronaphthalen-2-ylcarbamate (150 mg, 0.367 mmol) was combined with dioxane (2 ml) to give a yellow solution. A solution of hydrochloric acid in dioxane (4M, 1.38 ml, 5.5 mmol) was added and the solution was shaken at 60° C. for 2.5 hours. The reaction mixture was concentrated in vacuo and diethylether was added. The solid was separated by filtration through sintered glass and dried in vacuo. (S)—N6-(5-(Trifluoromethyl)pyrimidin-2-yl)-1,2,3,4-tetrahydronaphthalene-2,6-diamine was obtained as hydrochloride salt, yellow solid (97 mg, 77%). MS (ISP): 309.1 ([M+H]$^+$).

Example 24

(S)-1-(6-Amino-5,6,7,8-tetrahydronaphthalen-2-yl)-3-(4-(trifluoromethyl)phenyl)urea

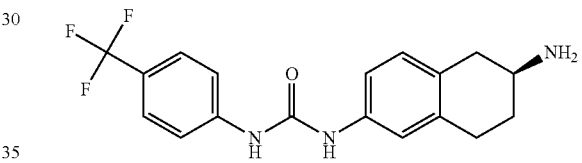

The title compound was obtained in analogy to Example 16 using 4-(trifluoromethyl)aniline instead of 6-(trifluoromethyl)pyridin-3-amine in step a). Off-white solid, as hydrochloride salt. MS (ISP): 350.2 ([M+H]$^+$).

Example 25

(S)—N-(6-Amino-5,6,7,8-tetrahydronaphthalen-2-yl)-4-chloro-3-(5-chlorofuran-2-yl)-1H-pyrazole-5-carboxamide

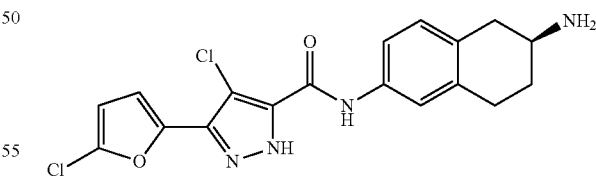

a) 4-chloro-3-(5-chlorofuran-2-yl)-1H-pyrazole-5-carboxylic acid 3-(Furan-2-yl)-1H-pyrazole-5-carboxylic acid (1.05 g, 5.89 mmol) was combined with dimethylformamide (10 ml) to give a yellow solution. The solution was cooled to 0° C. Perchloric acid (70%, 8.5 mg, 59 μmol) and N-chlorosuccinimide (1.65 g, 12.4 mmol) were added. After stirring at 80° C. for 30 min, the reaction mixture was diluted with ethylacetate and washed twice with water. The combined aqueous phase was basified by addition of 2 N aqueous sodium hydroxide solution and was extracted twice with ethylacetate. 5 N Aqueous hydrochloric acid was added to the aqueous layer and was extracted with ethyl acetate. The organic layer was dried over sodium sulfate, filtered and concentrated in vacuo to yield a brown solid (956 mg, 66%). MS (ISP): 247.4 ($\{^{35}Cl\}$ [M+H]$^+$), 249.4 ($\{^{37}Cl\}$ [M+H]$^+$).

b) (S)-tert-Butyl 6-(4-chloro-3-(5-chlorofuran-2-yl)-1H-pyrazole-5-carboxamido)-1,2,3,4-tetrahydronaphthalen-2-ylcarbamate (S)-tert-Butyl 6-amino-1,2,3,4-tetrahydronaphthalen-2-ylcarbamate (25 mg, 0.095 mmol) and 4-chloro-3-(5-chlorofuran-2-yl)-1H-pyrazole-5-carboxylic acid (24 mg, 0.095 mmol) were dissolved in methanol (0.5 ml) and cooled to 0° C. 4-(4,6-Dimethoxy-1,3,5-triazin-2-yl)-4-methylmorpholinium chloride (DMTMM, 32 mg, 0.114 mmol) was added and the cooling bath was removed. The reaction mixture was stirred at room temperature overnight. The solvent was evaporated and the residue was dissolved in ethyl acetate, washed with 1 N aqueous sodium hydroxide solution and 1 M aqueous ammonium chloride solution. The organic layer was dried over magnesium sulfate and evaporated. The crude material was purified by flash chromatography (silica gel, 10 g, 10% to 35% ethyl acetate in heptane) to yield a white solid (28 mg, 60%). MS (ISP): 435.1 ($\{^{35}Cl\}$ [M+H]$^+$), 437.1 ($\{^{37}Cl\}$ [M+H]$^+$).

c) (S)—N-(6-Amino-5,6,7,8-tetrahydronaphthalen-2-yl)-4-chloro-3-(5-chlorofuran-2-yl)-1H-pyrazole-5-carboxamide hydrochloride (S)-tert-Butyl 6-(4-chloro-3-(5-chlorofuran-2-yl)-1H-pyrazole-5-carboxamido)-1,2,3,4-tetrahydronaphthalen-2-ylcarbamate (25 mg, 0.051 mmol) was dissolved in dioxane (0.2 ml) and a 4 M solution of hydrogen chloride in dioxane (200 µl, 0.76 mmol) was added. The clear reaction mixture was shaken at 60° C. for 2 hours. The dioxane was removed under reduced pressure and diethyl ether was added. The solid was filtered and washed with more diethyl ether and then was dried under high vacuum. (S)—N-(6-Amino-5,6,7,8-tetrahydronaphthalen-2-yl)-4-chloro-3-(5-chlorofuran-2-yl)-1H-pyrazole-5-carboxamide was obtained as hydrochloride salt, light yellow solid (25 mg, 68%). MS (ISP): 391.1 ($\{^{35}Cl\}$ [M+H]$^+$), 393.1 ($\{^{37}Cl\}$ [M+H]$^+$).

Example 26

(S)—N-(6-Amino-5,6,7,8-tetrahydronaphthalen-2-yl)-4-chloro-5-methylisoxazole-3-carboxamide

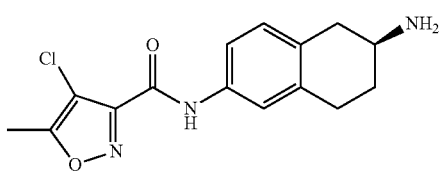 [SMILES: Cc1onc(C(=O)Nc2ccc3c(c2)CC[C@H](N)C3)c1Cl]

The title compound was obtained in analogy to Example 25 using 4-chloro-5-methylisoxazole-3-carboxylic acid instead of 4-chloro-3-(5-chlorofuran-2-yl)-1H-pyrazole-5-carboxylic acid in step b). Yellow solid, as hydrochloride salt. MS (ISP): 401.1 ($\{^{35}Cl\}$ [M+H]$^+$), 403.1 ($\{^{37}Cl\}$[M+H]$^+$).

Example 27

(S)—N-(6-Amino-5,6,7,8-tetrahydronaphthalen-2-yl)-1-p-tolyl-1H-pyrazole-4-carboxamide

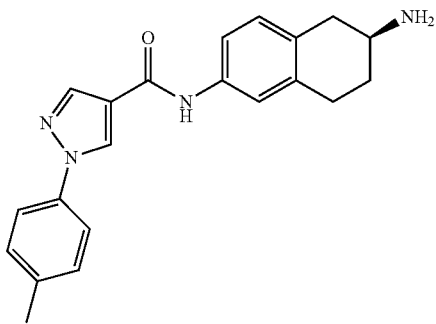 [SMILES: Cc1ccc(-n2cc(C(=O)Nc3ccc4c(c3)CC[C@H](N)C4)cn2)cc1]

The title compound was obtained in analogy to Example 25 using 1-p-tolyl-1H-pyrazole-4-carboxylic acid instead of 4-chloro-3-(5-chlorofuran-2-yl)-1H-pyrazole-5-carboxylic acid in step b). Off-white solid, as hydrochloride salt. MS (ISP): 347.2 ([M+H]$^+$).

Example 28

(S)—N-(6-Amino-5,6,7,8-tetrahydronaphthalen-2-yl)-1-(3,4-dichlorophenyl)-1H-pyrazole-4-carboxamide

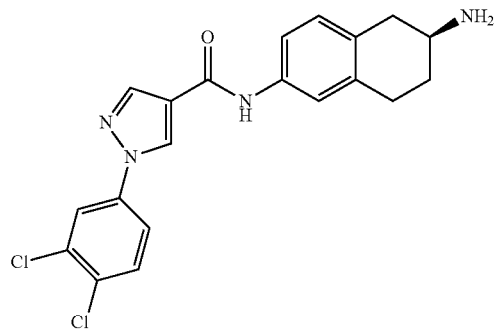 [SMILES: N[C@H]1CCc2cc(NC(=O)c3cnn(-c4ccc(Cl)c(Cl)c4)c3)ccc2C1]

The title compound was obtained in analogy to Example 25 using 1-(3,4-dichlorophenyl)-1H-pyrazole-4-carboxylic acid instead of 4-chloro-3-(5-chlorofuran-2-yl)-1H-pyrazole-5-carboxylic acid in step b). Off-white solid, as hydrochloride salt. MS (ISP): 306.1 ($\{^{35}Cl\}$ [M+H]$^+$), 308.1 ($\{^{37}Cl\}$ [M+H]$^+$).

Example 29

(S)—N-(6-Amino-5,6,7,8-tetrahydronaphthalen-2-yl)-1-(4-(trifluoromethoxy)phenyl)-1H-pyrazole-4-carboxamide

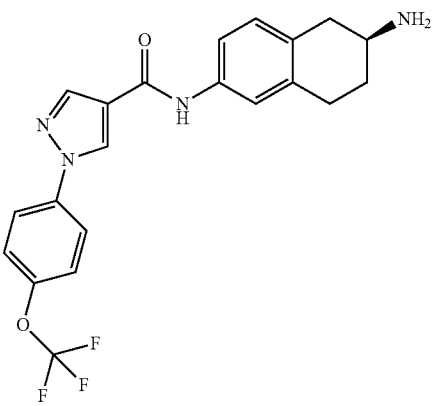 [SMILES: N[C@H]1CCc2cc(NC(=O)c3cnn(-c4ccc(OC(F)(F)F)cc4)c3)ccc2C1]

The title compound was obtained in analogy to Example 25 using 1-(4-(trifluoromethoxy)-phenyl)-1H-pyrazole-4-carboxylic acid instead of 4-chloro-3-(5-chlorofuran-2-yl)-1H-pyrazole-5-carboxylic acid in step b). Light yellow solid, as hydrochloride salt. MS (ISP): 417.2 ([M+H]$^+$).

Example 30

(S)—N6-(5-Chloropyrimidin-2-yl)-1,2,3,4-tetrahydronaphthalene-2,6-diamine

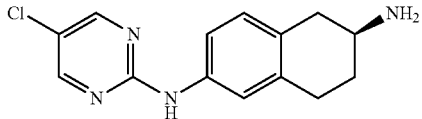 [SMILES: N[C@H]1CCc2cc(Nc3ncc(Cl)cn3)ccc2C1]

The title compound was obtained in analogy to Example 23 using 2-chloro-5-(trifluoromethyl)pyrimidine instead of 2,5-dichloropyrimidine in step a). Yellow solid, as hydrochloride salt. MS (ISP): 275.1 ({$^{35}$Cl} [M+H]$^+$), 277.1 ({$^{37}$Cl} [M+H]$^+$).

Example 31

6-Amino-N-(6-ethoxypyridin-3-yl)-5,6,7,8-tetrahydronaphthalene-2-carboxamide

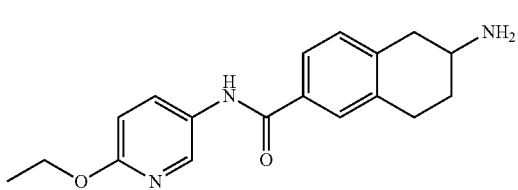 [SMILES: CCOc1ccc(NC(=O)c2ccc3c(c2)CCC(N)C3)cn1]

a) Methyl 6-(tert-butoxycarbonylamino)-5,6,7,8-tetrahydronaphthalene-2-carboxylate tert-Butyl 6-bromo-1,2,3,4-tetrahydronaphthalen-2-ylcarbamate (1.75 g, 5.36 mmol) was dissolved in a mixture of ethyl acetate (30 ml) and methanol (30 ml). The solution was transferred in an autoclave and under argon 1,1'-bis(diphenylphosphino)ferrocene-palladium(II)dichloride dichloromethane adduct (400 mg, 0.49 mmol) and triethylamine (818 mg, 1.13 ml, 8.05 mmol) were added. The autoclave was pressurized with carbon monoxide at 50 bar and the mixture was stirred at 110° C. for 20 hours. After cooling down to room temperature the reaction mixture was concentrated in vacuo and purified by flash chromatography (silica gel, 70 g, 0% to 50% ethyl acetate in hexanes) to yield a white solid (1.19 g, 73%). MS (ISP): 250.2 ([M–tBu+H]$^+$).

b) 6-(tert-Butoxycarbonylamino)-5,6,7,8-tetrahydronaphthalene-2-carboxylic acid

In a 50 mL round-bottomed flask, methyl 6-(tert-butoxycarbonylamino)-5,6,7,8-tetrahydronaphthalene-2-carboxylate (1.19 g, 3.9 mmol) was dissolved in tetrahydrofuran (8 ml) to give a colourless solution. A solution of lithium hydroxide in water (1M, 10 ml, 10 mmol) was added and the mixture was stirred at room temperature overnight. For work-up a solution of 5 N hydrochloric acid was added until acidic pH. The reaction mixture was extracted with ethyl acetate which was washed with brine. The organic layer was dried over sodium sulfate and concentrated in vacuo to yield a white solid (1.3 g, 99.6%). MS (ISP): 290.1 ([M–H]$^+$).

c) tert-Butyl 6-(6-ethoxypyridin-3-ylcarbamoyl)-1,2,3,4-tetrahydronaphthalen-2-ylcarbamate In a 10 mL round-bottomed flask, 1-chloro-N,N,2-trimethylpropenylamine (25 mg, 25 µl, 0.189 mmol) was dissolved in dichloromethane (1 ml) and 6-(tert-butoxycarbonylamino)-5,6,7,8-tetrahydronaphthalene-2-carboxylic acid (50 mg, 0.172 mmol) was added. The reaction mixture was stirred 30 min at room temperature. This acid chloride solution was added to a solution of diisopropylethylamine (44 mg, 60 µl, 0.343 mmol) and 6-ethoxypyridin-3-amine (24 mg, 0.172 mmol) in 1 ml dichloromethane. The mixture was stirred at room temperature overnight. For workup the reaction mixture was poured into ethyl acetate, washed with diluted sodium hydroxide solution, diluted hydrochloric acid and brine. The organic layer was dried over sodium sulfate and concentrated in vacuo. The crude material was purified by flash chromatography (silica gel, 20 g, 0% to 70% ethyl acetate in hexanes) to yield a white solid (27 mg, 38%). MS (ISP): 412.3 ([M+H]$^+$).

d) 6-Amino-N-(6-ethoxypyridin-3-yl)-5,6,7,8-tetrahydronaphthalene-2-carboxamide hydrochloride tert-Butyl 6-(6-ethoxypyridin-3-ylcarbamoyl)-1,2,3,4-tetrahydronaphthalen-2-ylcarbamate (27 mg, 0.066 mmol) was dissolved in dioxane (2 ml) and a 4 M solution of hydrogen chloride in dioxane (0.33 ml, 1.31 mmol) was added. The reaction mixture was shaken at 60° C. overnight. The dioxane was removed under reduced pressure and diethyl ether was added. The solid was filtered and washed with more diethyl ether and then was dried under high vacuum. 6-Amino-N-(6-ethoxypyridin-3-yl)-5,6,7,8-tetrahydronaphthalene-2-carboxamide was obtained as hydrochloride salt, white solid (17 mg, 75%). MS (ISP): 312.2 ([M+H]+).

Example 32

6-Amino-N-(2-cyclopropylpyrimidin-5-yl)-5,6,7,8-tetrahydronaphthalene-2-carboxamide

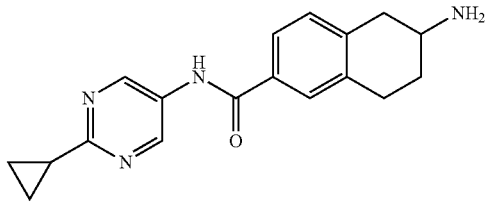 [SMILES: NC1CCc2cc(C(=O)Nc3cnc(C4CC4)nc3)ccc2C1]

The title compound was obtained in analogy to Example 31 using 2-cyclopropylpyrimidin-5-amine instead of 6-ethoxypyridin-3-amine in step c). White solid, as hydrochloride salt. MS (ISP): 309.1 ([M+H]+).

Example 33

6-Amino-N-(5-(trifluoromethyl)pyrazin-2-yl)-5,6,7,8-tetrahydronaphthalene-2-carboxamide

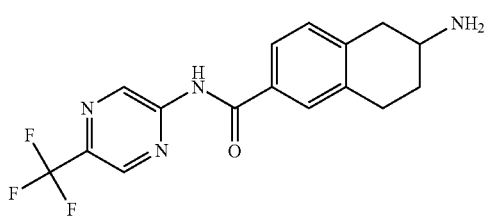 [SMILES: NC1CCc2cc(C(=O)Nc3cnc(C(F)(F)F)cn3)ccc2C1]

The title compound was obtained in analogy to Example 31 using 5-(trifluoromethyl)pyrazin-2-amine instead of 6-ethoxypyridin-3-amine in step c). Off-white solid, as hydrochloride salt. MS (ISP): 337.1 ([M+H]+).

Example 34

6-Amino-N-(4-(trifluoromethyl)phenyl)-5,6,7,8-tetrahydronaphthalene-2-carboxamide

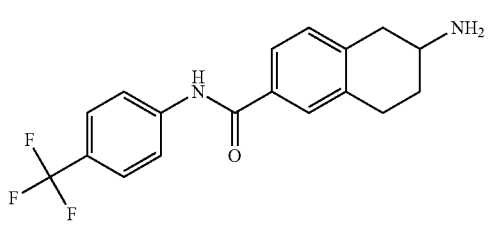 [SMILES: NC1CCc2cc(C(=O)Nc3ccc(C(F)(F)F)cc3)ccc2C1]

The title compound was obtained in analogy to Example 31 using 4-(trifluoromethyl)aniline instead of 6-ethoxypyridin-3-amine in step c). White solid, as hydrochloride salt. MS (ISP): 335.1 ([M+H]+).

Example 35

6-Amino-N-(4-(trifluoromethyl)benzyl)-5,6,7,8-tetrahydronaphthalene-2-carboxamide

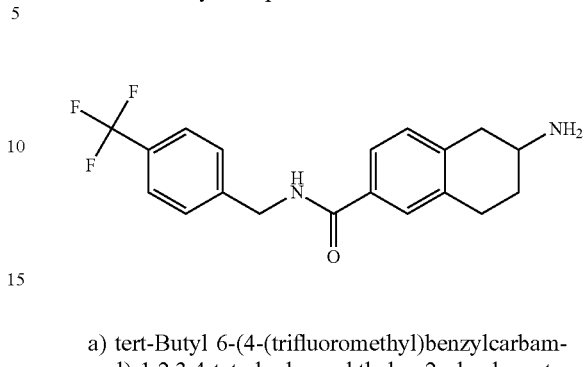

a) tert-Butyl 6-(4-(trifluoromethyl)benzylcarbamoyl)-1,2,3,4-tetrahydronaphthalen-2-ylcarbamate In a sealed tube, 4-(trifluoromethyl)-benzylamine (30.1 mg, 0.172 mmol) and 6-(tert-butoxycarbonylamino)-5,6,7,8-tetrahydronaphthalene-2-carboxylic acid (50 mg, 0.172 mmol) were combined with tetrahydrofuran (1 ml), N-methylmorpholine (69.4 mg, 75.6 µl, 0.686 mmol) and O-(benzotriazol-1-yl)-N,N,N',N'-tetramethyluronium tetrafluoroborate (TBTU, 110 mg, 0.343 mmol). The reaction mixture was stirred at 50° C. overnight. The reaction mixture was poured into ethyl acetate and extracted with diluted hydrochloric acid and brine. The organic layer was concentrated in vacuo. The crude material was purified by flash chromatography (silica gel, 20 g, 0% to 80% ethyl acetate in hexanes) to yield a white solid (55 mg, 72%). MS (ISP): 393.2 ([M−tBu+H]+).

b) 6-Amino-N-(4-(trifuoromethyl)benzyl)-5,6,7,8-tetrahydronaphthalene-2-carboxamide hydrochloride tert-Butyl 6-(4-(trifluoromethyl)benzylcarbamoyl)-1,2,3,4-tetrahydronaphthalen-2-ylcarbamate (53 mg, 0.118 mmol) was dissolved in dioxane (2 ml) and a 4 M solution of hydrogen chloride in dioxane (0.59 ml, 2.36 mmol) was added. The reaction mixture was shaken at 60° C. overnight. The dioxane was removed under reduced pressure and diethyl ether was added. The solid was filtered and washed with more diethyl ether and then was dried under high vacuum. 6-Amino-N-(4-(trifluoromethyl)benzyl)-5,6,7,8-tetrahydronaphthalene-2-carboxamide was obtained as hydrochloride salt (34 mg, 76%). White solid, MS (ISP): 349.1 ([M+H]+).

Example 36

6-Amino-N-((6-chloropyridin-3-yl)methyl)-5,6,7,8-tetrahydronaphthalene-2-carboxamide

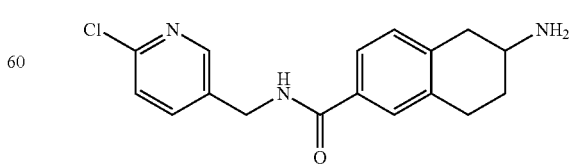

The title compound was obtained in analogy to Example 35 using (6-chloropyridin-3-yl)methanamine instead of 4-(trifluoromethyl)-benzylamine in step a). White solid, as hydrochloride salt. MS (ISP): 316.1 ({$^{35}$Cl} [M+H]$^+$), 318.1 ({$^{37}$Cl} [M+H]$^+$).

Example 37

6-Amino-N-(6-chloropyridin-3-yl)-5,6,7,8-tetrahydronaphthalene-2-carboxamide

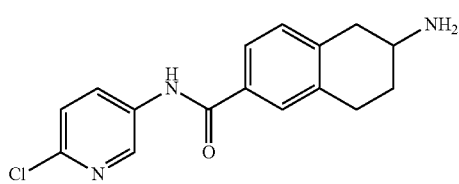 [SMILES: NC1CCc2cc(C(=O)Nc3ccc(Cl)nc3)ccc2C1]

The title compound was obtained in analogy to Example 31 using 6-chloropyridin-3-amine instead of 6-ethoxypyridin-3-amine in step c). White solid, as hydrochloride salt. MS (ISP): 302.1 ({$^{35}$Cl} [M+H]$^+$), 304.1 ({$^{37}$Cl} [M+H]$^+$).

Example 38

(S)—N6-(5-(Trifluoromethyl)pyridin-2-yl)-1,2,3,4-tetrahydronaphthalene-2,6-diamine

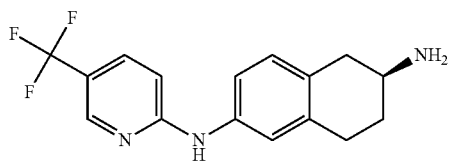 [SMILES: N[C@H]1CCc2cc(Nc3ccc(C(F)(F)F)cn3)ccc2C1]

The title compound was obtained in analogy to Example 23 using 2-chloro-5-(trifluoromethyl)pyridine instead of 2,5-dichloropyrimidine in step a). Light brown solid, as hydrochloride salt. MS (ISP): 308.1 ([M+H]$^+$).

Example 39

(S)—N-(6-Amino-5,6,7,8-tetrahydronaphthalen-2-yl)-2-fluoronicotinamide

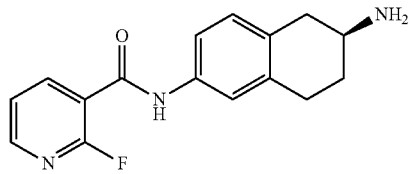 [SMILES: N[C@H]1CCc2cc(NC(=O)c3cccnc3F)ccc2C1]

a) (S)-tert-Butyl 6-(2-fluoronicotinamido)-1,2,3,4-tetrahydronaphthalen-2-ylcarbamate In a sealed tube, (S)-tert-butyl 6-amino-1,2,3,4-tetrahydronaphthalen-2-ylcarbamate (30 mg, 0.114 mmol) and 2-fluoronicotinic acid (21 mg, 0.15 mmol) were combined with tetrahydrofuran (0.65 ml). O-(Benzotriazol-1-yl)-N,N,N',N'-tetramethyluronium hexafluorophosphate (HBTU, 87 mg, 0.23 mmol) and N-methylmorpholine (46 mg, 50 µl, 0.46 mmol) were added. The reaction mixture was shaken at 60° C. for 17 h. Ethyl acetate and water were added. The organic layer was dried over magnesium sulfate and evaporated. The crude material was purified by flash chromatography (silica gel, 10 g, 10% to 30% ethyl acetate in heptane) to yield a light yellow solid (28 mg, 62%). MS (ISP): 330.2 ([M-tBu+H]$^+$).

b) (S)—N-(6-Amino-5,6,7,8-tetrahydronaphthalen-2-yl)-2-fluoronicotinamide hydrochloride (S)-tert-Butyl 6-(2-fluoronicotinamido)-1,2,3,4-tetrahydronaphthalen-2-ylcarbamate (23 mg, 0.60 mmol) was dissolved in dioxane (0.23 ml) and a 4 M solution of hydrogen chloride in dioxane (224 µl, 0.89 mmol) was added. The clear reaction mixture was shaken at 60° C. for 2 hours. The dioxane was removed under reduced pressure and diethyl ether was added. The solid was filtered and washed with more diethyl ether and then was dried under high vacuum. (S)—N-(6-Amino-5,6,7,8-tetrahydronaphthalen-2-yl)-2-fluoronicotinamide was obtained as hydrochloride salt, light brown solid (10 mg, 52%). MS (ISP): 286.2 ([M+H]$^+$).

Example 40

(S)—N-(6-Amino-5,6,7,8-tetrahydronaphthalen-2-yl)-6-chloronicotinamide

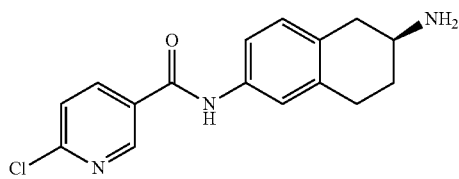 [SMILES: N[C@H]1CCc2cc(NC(=O)c3ccc(Cl)nc3)ccc2C1]

The title compound was obtained in analogy to Example 39 using 6-chloronicotinic acid instead of 2-fluoronicotinic acid in step a). Light yellow solid, as hydrochloride salt. MS (ISP): 302.2 ({$^{35}$Cl} [M+H]$^+$), 304.1 ({$^{37}$Cl} [M+H]$^+$).

Example 41

(S)—N-(6-Amino-5,6,7,8-tetrahydronaphthalen-2-yl)-5,6-dichloronicotinamide

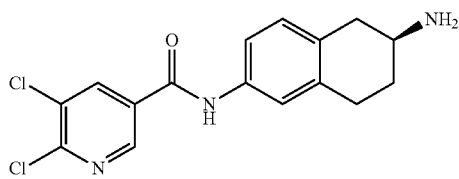 [SMILES: N[C@H]1CCc2cc(NC(=O)c3cnc(Cl)c(Cl)c3)ccc2C1]

The title compound was obtained in analogy to Example 39 using 5,6-dichloronicotinic acid instead of 2-fluoronicotinic acid in step a). Off-white solid, as hydrochloride salt. MS (ISP): 336.1 ({$^{35}$Cl} [M+H]$^+$), 338.1 ({$^{37}$Cl} [M+H]$^+$).

Example 42

(S)—N-(6-Amino-5,6,7,8-tetrahydronaphthalen-2-yl)-3,4-difluorobenzamide

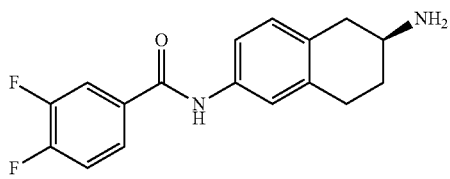 [SMILES: N[C@H]1CCc2cc(NC(=O)c3ccc(F)c(F)c3)ccc2C1]

The title compound was obtained in analogy to Example 39 using 3,4-difluorobenzoic acid instead of 2-fluoronicotinic acid in step a). Light-brown solid, as hydrochloride salt. MS (ISP): 303.2 ([M+H]$^+$).

Example 43

(S)—N-(6-Amino-5,6,7,8-tetrahydronaphthalen-2-yl)-2-naphthamide

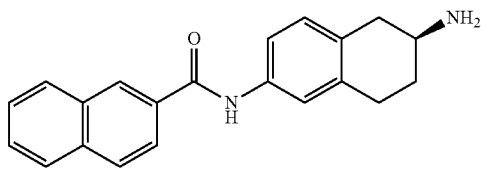 [SMILES: N[C@H]1CCc2cc(NC(=O)c3ccc4ccccc4c3)ccc2C1]

The title compound was obtained in analogy to Example 39 using 2-naphthoic acid instead of 2-fluoronicotinic acid in step a). White solid, as hydrochloride salt. MS (ISP): 317.2 ([M+H]$^+$).

Example 44

(S)—N6-(4-(Trifluoromethyl)phenyl)-1,2,3,4-tetrahydronaphthalene-2,6-diamine

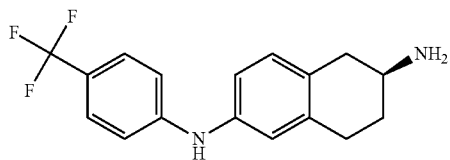 [SMILES: N[C@H]1CCc2cc(Nc3ccc(C(F)(F)F)cc3)ccc2C1]

a) (S)-tert-Butyl 6-(4-(trifluoromethyl)phenylamino)-1,2,3,4-tetrahydronaphthalen-2-ylcarbamate In a sealed tube, (S)-tert-butyl 6-amino-1,2,3,4-tetrahydronaphthalen-2-ylcarbamate (70 mg, 0.267 mmol), 1-iodo-4-(trifluoromethyl)benzene (80 mg, 42.6 µl, 0.294 mmol) and cesium carbonate (130 mg, 0.4 mmol) were combined with dioxane (2 ml) to give a yellow suspension. The mixture was degassed by bubbling through argon for several minutes. 4,5-Bis(diphenylphosphino)-9,9-dimethylxanthene (Xantphos, 9.26 mg, 16.0 µmol) and tris(dibenzylideneacetone)dipalladium chloroform complex (8.3 mg, 8 µmol) were added. The reaction mixture was capped and stirred at 100° C. for 2 h. For work-up the crude reaction mixture was filtered, concentrated in vacuo and purified by flash chromatography (silica gel, 20 g, 0% to 80% Ethyl acetate in hexanes) to yield a yellow oil (45 mg, 41%). MS (ISP): 351.2 ([M–tBu+H]$^+$).

b) (S)—N6-(4-(Trifluoromethyl)phenyl)-1,2,3,4-tetrahydronaphthalene-2,6-diamine (S)-tert-Butyl 6-(4-(trifluoromethyl)phenylamino)-1,2,3,4-tetrahydronaphthalen-2-ylcarbamate (43 mg, 0.106 mmol) was dissolved in dioxane (2 ml) and a 4 M solution of hydrogen chloride in dioxane (529 µl, 2.12 mmol) was added. The clear reaction mixture was shaken at 60° C. for 2.5 hours. The dioxane was removed under reduced pressure and diethyl ether was added. After short sonication in an ultrasound bath the solid was filtered and washed with more diethyl ether and was dried under high vacuum. (S)—N6-(4-(Trifluoromethyl)phenyl)-1,2,3,4-tetrahydronaphthalene-2,6-diamine was obtained as hydrochloride salt, light brown solid (22 mg, 62%). MS (ISP): 307.1 ([M+H]$^+$).

Example 45

(S)—N-(6-Amino-5,6,7,8-tetrahydronaphthalen-2-yl)-2-(trifluoromethyl)isonicotinamide

The title compound was obtained in analogy to Example 39 using 2-(trifluoromethyl)isonicotinic acid instead of 2-fluoronicotinic acid in step a). Yellow solid, as hydrochloride salt. MS (ISP): 336.1 ([M+H]$^+$).

Example 46

(S)—N-(6-Amino-5,6,7,8-tetrahydronaphthalen-2-yl)-2,6-dichloroisonicotinamide

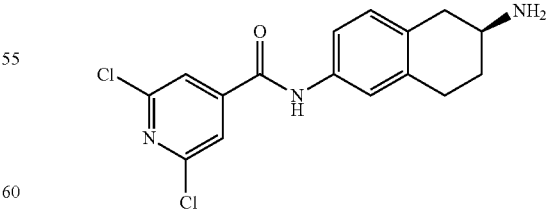

The title compound was obtained in analogy to Example 39 using 2,6-dichloroisonicotinic acid instead of 2-fluoronicotinic acid in step a). Light yellow solid, as hydrochloride salt. MS (ISP): 336.1 ({$^{35}$Cl} [M+H]$^+$), 338.1 ({$^{37}$Cl} [M+H]$^+$).

Example 47

(S)-4-(6-Amino-5,6,7,8-tetrahydronaphthalen-2-ylamino)benzonitrile

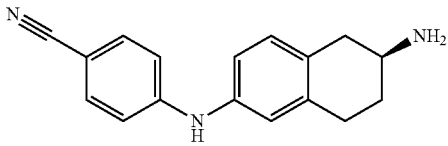 [SMILES: N#Cc1ccc(Nc2ccc3c(c2)CC[C@H](N)C3)cc1]

The title compound was obtained in analogy to Example 44 using 4-iodobenzonitrile instead of 1-iodo-4-(trifluoromethyl)benzene in step a). Light brown solid, as hydrochloride salt. MS (ISP): 264.1 ([M+H]$^+$).

Example 48

(S)—N6-(4-Chlorophenyl)-1,2,3,4-tetrahydronaphthalene-2,6-diamine

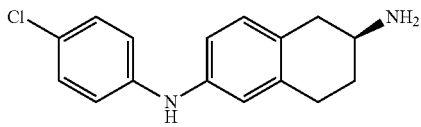 [SMILES: N[C@H]1CCc2cc(Nc3ccc(Cl)cc3)ccc2C1]

The title compound was obtained in analogy to Example 44 using 1-chloro-4-iodobenzene instead of 1-iodo-4-(trifluoromethyl)benzene in step a). Light brown solid, as hydrochloride salt. MS (ISP): 273.1 ({$^{35}$Cl} [M+H]$^+$), 275.1 ({$^{37}$Cl} [M+H]$^+$).

Example 49

(S)—N-(6-Amino-5,6,7,8-tetrahydronaphthalen-2-yl)-5-chloronicotinamide

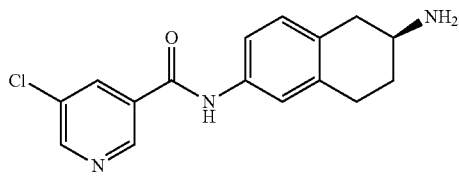 [SMILES: N[C@H]1CCc2cc(NC(=O)c3cncc(Cl)c3)ccc2C1]

The title compound was obtained in analogy to Example 39 using 5-chloronicotinic acid instead of 2-fluoronicotinic acid in step a). Light yellow solid, as hydrochloride salt. MS (ISP): 302.1 ({$^{35}$Cl} [M+H]$^+$), 304.1 ({$^{37}$Cl} [M+H]$^+$).

Example 50

(S)—N-(6-Amino-5,6,7,8-tetrahydronaphthalen-2-yl)-2-chloro-6-methylisonicotinamide

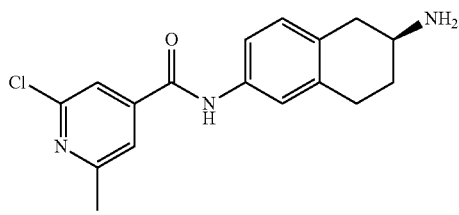 [SMILES: Cc1cc(C(=O)Nc2ccc3c(c2)CC[C@H](N)C3)cc(Cl)n1]

The title compound was obtained in analogy to Example 39 using 2-chloro-6-methylisonicotinic acid instead of 2-fluoronicotinic acid in step a). Yellow solid, as hydrochloride salt. MS (ISP): 316.1 ({$^{35}$Cl} [M+H]$^+$), 318.1 ({$^{37}$Cl} [M+H]$^+$).

Example 51

(S)—N-(6-Amino-5,6,7,8-tetrahydronaphthalen-2-yl)-3-ethyl-4-methyl-1H-pyrazole-5-carboxamide

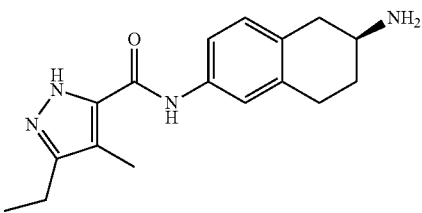 [SMILES: CCc1n[nH]c(C(=O)Nc2ccc3c(c2)CC[C@H](N)C3)c1C]

The title compound was obtained in analogy to Example 39 using 3-ethyl-4-methyl-1H-pyrazole-5-carboxylic acid instead of 2-fluoronicotinic acid in step a). Off-white solid, as hydrochloride salt. MS (ISP): 299.2 ([M+H]$^+$).

Example 52

(S)—N-(6-Amino-5,6,7,8-tetrahydronaphthalen-2-yl)-4-bromo-5-(2,2-difluoroethoxy)-1-ethyl-1H-pyrazole-3-carboxamide

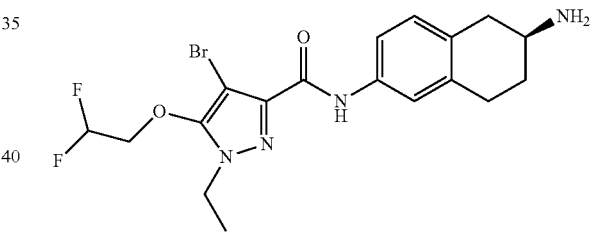

a) Ethyl 5-(2,2-difluoroethoxy)-1-ethyl-1H-pyrazole-3-carboxylate

Ethyl 1-ethyl-5-hydroxy-1H-pyrazole-3-carboxylate (200 mg, 1.09 mmol) was dissolved in dimethylformamide (1.00 ml), 2,2-difluoroethyl trifluoromethanesulfonate (279 mg, 173 µl, 1.3 mmol) and potassium carbonate (225 mg, 1.63 mmol) were added. The reaction mixture was shaken overnight at 60° C. Ethyl acetate and water were added. The organic layer was washed with brine, dried over magnesium sulfate and evaporated.

The crude material was purified by flash chromatography (silica gel, 10 g, 10% to 30% Ethyl acetate in heptane) to yield an off-white solid (120 mg, 45%). MS (ISP): 249.2 ([M+H]$^+$).

b) Ethyl 4-bromo-5-(2,2-difluoroethoxy)-1-ethyl-1H-pyrazole-3-carboxylate

Ethyl 5-(2,2-difluoroethoxy)-1-ethyl-1H-pyrazole-3-carboxylate (320 mg, 1.29 mmol) was dissolved in dimethylformamide (6.45 ml) and the reaction mixture was cooled to 0° C. N-Bromosuccinimide (298 mg, 1.68 mmol) was slowly added and the reaction mixture was allowed to stir at rt for 5 hours. The solution was then extracted with water and ethyl acetate. The organic layer was dried with magnesium sulfate, filtered and concentrated in vacuo.

The crude material was purified by flash chromatography (silica gel, 20 g, 10% to 30% Ethyl acetate in heptane) to yield a light yellow oil (386 mg, 92%). MS (ISP): 327.0 ({$^{79}$Br} [M+H]$^+$), 329.0 ({$^{81}$Br} [M+H]$^+$).

c) 4-Bromo-5-(2,2-difluoroethoxy)-1-ethyl-1H-pyrazole-3-carboxylic acid

Ethyl 4-bromo-5-(2,2-difluoroethoxy)-1-ethyl-1H-pyrazole-3-carboxylate (374 mg, 1.14 mmol) was dissolved in tetrahydrofuran (2.38 ml) and 1 M aqueous lithium hydroxide solution (1.37 ml, 1.37 mmol) was added. The reaction mixture was shaken at 60° C. overnight. Diethyl ether was added. The aqueous layer was separated, acidified by addition of 2 M aqueous hydrochloric acid solution and extracted with a mixture diethyl ether/ethyl acetate. The organic layer was dried over magnesium sulfate, filtered and evaporated to give a light brown solid (305 mg, 89%). MS (ISP): 299.1 ({$^{79}$Br} [M+H]$^+$), 301.0 ({$^{81}$Br} [M+H]$^+$).

d) (S)—N-(6-Amino-5,6,7,8-tetrahydronaphthalen-2-yl)-4-bromo-5-(2,2-difluoroethoxy)-1-ethyl-1H-pyrazole-3-carboxamide The title compound was obtained in analogy to Example 39 using 4-bromo-5-(2,2-difluoroethoxy)-1-ethyl-1H-pyrazole-3-carboxylic acid instead of 2-fluoronicotinic acid in step a) White solid, as hydrochloride salt. MS (ISP): 443.1 ({$^{79}$Br} [M+H]$^+$), 445.1 ({$^{81}$Br} [M+H]$^+$).

Example 53

(S)—N6-(4-Ethylphenyl)-1,2,3,4-tetrahydronaphthalene-2,6-diamine

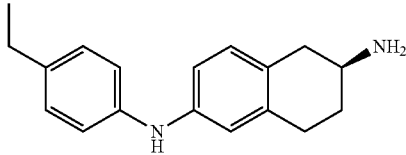 [SMILES: CCc1ccc(Nc2ccc3c(c2)CC[C@H](N)C3)cc1]

The title compound was obtained in analogy to Example 44 using 1-ethyl-4-iodobenzene instead of 1-iodo-4-(trifluoromethyl)benzene in step a). White solid, as hydrochloride salt. MS (ISP): 267.2 ([M+H]$^+$).

Example 54

6-Amino-N-(3-methoxyphenyl)-5,6,7,8-tetrahydronaphthalene-2-carboxamide

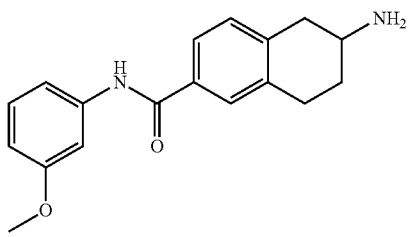 [SMILES: COc1cccc(NC(=O)c2ccc3c(c2)CCC(N)C3)c1]

a) tert-Butyl 6-(3-methoxyphenylcarbamoyl)-1,2,3,4-tetrahydronaphthalen-2-ylcarbamate In a sealed tube, 6-(tert-butoxycarbonylamino)-5,6,7,8-tetrahydronaphthalene-2-carboxylic acid (50 mg, 0.172 mmol) was dissolved in methanol (1 ml) and the solution was cooled to 0-5° C. 4-(4,6-Dimethoxy-1,3,5-triazin-2-yl)-4-methylmorpholinium chloride (DMTMM, 52 mg, 0.189 mmol) in methanol (0.5 ml) was added by syringe. The mixture was stirred for 30 min at 0-5° C. Then 3-methoxyaniline (21 mg, 0.172 mmol) was added. The reaction mixture was stirred at room temperature overnight. The reaction mixture was poured into ethyl acetate and extracted with diluted hydrochloric acid and brine. The organic layer was concentrated in vacuo. The crude material was purified by flash chromatography (silica gel, 20 g, 0% to 70% ethyl acetate in hexanes) to yield a white solid (64 mg, 94%). MS (ISP): 341.2 ([M−tBu+H]$^+$).

b) 6-Amino-N-(3-methoxyphenyl)-5,6,7,8-tetrahydronaphthalene-2-carboxamide hydrochloride tert-Butyl 6-(3-methoxyphenylcarbamoyl)-1,2,3,4-tetrahydronaphthalen-2-ylcarbamate (60 mg, 0.151 mmol) was dissolved in dioxane (2 ml) and a 4 M solution of hydrogen chloride in dioxane (0.57 ml, 2.27 mmol) was added. The reaction mixture was shaken at 60° C. overnight. The dioxane was removed under reduced pressure and diethyl ether was added. The solid was filtered and washed with more diethyl ether. Further purification was obtained by distribution of this solid between ethyl acetate and sodium hydroxide solution (0.5N). The organic layer was washed with brine, dried over sodium sulfate and concentrated in vacuo. The product was purified by reversed phase HPLC (column YMC Triart C18, acetonitrile/water with 0.1% triethylamine). The product obtained was concentrated in vacuo and dissolved in ethyl acetate (1 ml). A solution of hydrochloric acid in diethyl ether (2 N, 1 ml) was added. After concentration in vacuo a yellow solid was obtained (6 mg, 12%). MS (ISP): 297.1 ([M+H]$^+$).

Example 55

6-Amino-N-(3-(trifluoromethoxy)phenyl)-5,6,7,8-tetrahydronaphthalene-2-carboxamide

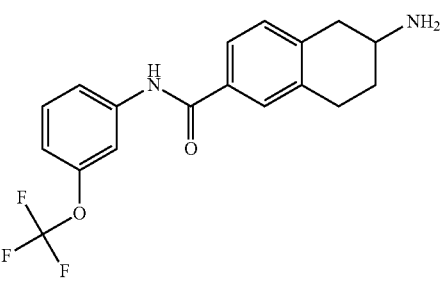

a) tert-Butyl 6-(3-(trifluoromethoxy)phenylcarbamoyl)-1,2,3,4-tetrahydronaphthalen-2-ylcarbamate In a sealed tube, 6-(tert-butoxycarbonylamino)-5,6,7,8-tetrahydronaphthalene-2-carboxylic acid (50 mg, 0.172 mmol) was dissolved in methanol (1 ml) and the solution was cooled to 0-5° C. 4-(4,6-Dimethoxy-1,3,5-triazin-2-yl)-

4-methylmorpholinium chloride (DMTMM, 52 mg, 0.189 mmol) in methanol (0.5 ml) was added by syringe. The mixture was stirred for 30 min at 0-5° C. Then 3-(trifluoromethoxy)aniline (30 mg, 0.172 mmol) was added. The reaction mixture was stirred at room temperature overnight. The reaction mixture was poured into ethyl acetate and extracted with diluted hydrochloric acid and brine. The organic layer was concentrated in vacuo. The crude material was purified by flash chromatography (silica gel, 20 g, 0% to 70% Ethyl acetate in hexanes) to yield a white solid (76 mg, 98%). MS (ISP): 395.2 ([M−tBu+H]$^+$).

b) 6-Amino-N-(3-(trifluoromethoxy)phenyl)-5,6,7,8-tetrahydronaphthalene-2-carboxamide hydrochloride tert-Butyl 6-(3-(trifluoromethoxy)phenylcarbamoyl)-1,2,3,4-tetrahydronaphthalen-2-ylcarbamate (70 mg, 0.155 mmol) was dissolved in dioxane (2 ml) and a 4 M solution of hydrogen chloride in dioxane (0.58 ml, 2.33 mmol) was added. The reaction mixture was shaken at 60° C. overnight. The dioxane was removed under reduced pressure and diethyl ether was added. The solid was filtered and washed with more diethyl ether. White solid (48 mg, 80%). MS (ISP): 351.1 ([M+H]$^+$).

Example 56

6-Amino-N-(4-ethylphenyl)-5,6,7,8-tetrahydronaphthalene-2-carboxamide

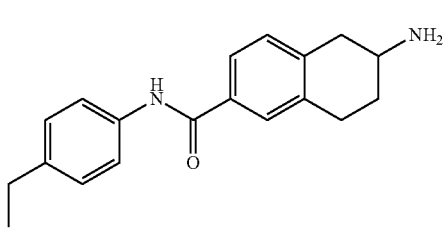 [SMILES: CCc1ccc(NC(=O)c2ccc3c(c2)CCC(N)C3)cc1]

The title compound was obtained in analogy to Example 55 using 4-ethylaniline instead of 3-(trifluoromethoxy)aniline in step a). White solid, as hydrochloride salt. MS (ISP): 295.2 ([M+H]$^+$).

Example 57

6-Amino-N-(4-chlorophenyl)-5,6,7,8-tetrahydronaphthalene-2-carboxamide

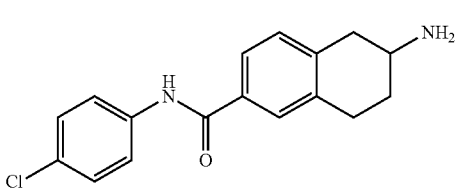 [SMILES: NC1CCc2cc(C(=O)Nc3ccc(Cl)cc3)ccc2C1]

The title compound was obtained in analogy to Example 55 using 4-chloroaniline instead of 3-(trifluoromethoxy)aniline in step a). White solid, as hydrochloride salt. MS (ISP): 301.1 ($\{^{35}Cl\}$[M+H]$^+$), 303.1 ($\{^{37}Cl\}$ [M+H]$^+$).

Example 58

6-Amino-N-(4-fluorophenyl)-5,6,7,8-tetrahydronaphthalene-2-carboxamide

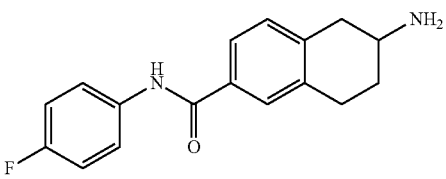 [SMILES: NC1CCc2cc(C(=O)Nc3ccc(F)cc3)ccc2C1]

The title compound was obtained in analogy to Example 55 using 4-fluoroaniline instead of 3-(trifluoromethoxy)aniline in step a). White solid, as hydrochloride salt. MS (ISP): 285.1 ([M+H]$^+$).

Example 59

6-Amino-N-(3-chlorophenyl)-5,6,7,8-tetrahydronaphthalene-2-carboxamide

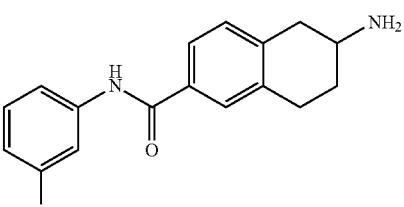

The title compound was obtained in analogy to Example 55 using 4-chloroaniline instead of 3-chloroaniline in step a). White solid, as hydrochloride salt. MS (ISP): 301.1 ($\{^{35}Cl\}$ [M+H]$^+$), 303.1 ($\{^{37}Cl\}$ [M+H]$^+$).

Example 60

6-Amino-N-(4-cyclopropylphenyl)-5,6,7,8-tetrahydronaphthalene-2-carboxamide

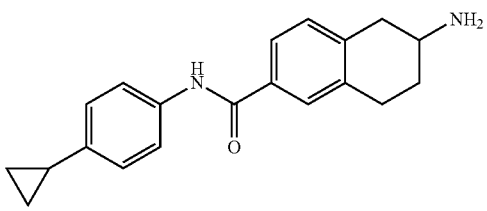 [SMILES: NC1CCc2cc(C(=O)Nc3ccc(C4CC4)cc3)ccc2C1]

The title compound was obtained in analogy to Example 55 using 4-fluoroaniline instead of 3-(trifluoromethoxy)aniline in step a). White solid, as hydrochloride salt. MS (ISP): 307.2 ([M+H]$^+$).

Example 61

(S)—N6-(3-(Trifluoromethoxy)phenyl)-1,2,3,4-tetrahydronaphthalene-2,6-diamine

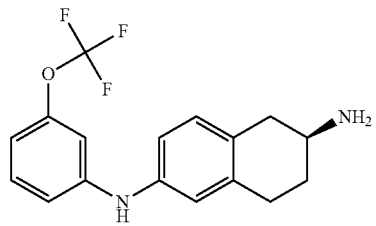 [SMILES: N[C@H]1CCc2cc(Nc3cccc(OC(F)(F)F)c3)ccc2C1]

The title compound was obtained in analogy to Example 44 using 1-iodo-3-(trifluoromethoxy)-benzene instead of 1-iodo-4-(trifluoromethyl)benzene in step a). White solid, as hydrochloride salt. MS (ISP): 323.1 ([M+H]$^+$).

Example 62

(S)-1-(6-Amino-5,6,7,8-tetrahydronaphthalen-2-yl)-3-((5-chloropyridin-2-yl)methyl)urea

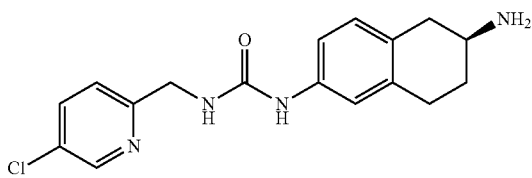

a) (S)-tert-Butyl 6-(3-((5-chloropyridin-2-yl)methyl)ureido)-1,2,3,4-tetrahydronaphthalen-2-ylcarbamate In a 25 mL round-bottomed flask, (S)-tert-butyl 6-amino-1,2,3,4-tetrahydronaphthalen-2-ylcarbamate (70 mg, 0.267 mmol) was dissolved in dichloroethane (2 ml). Triethylamine (81 mg, 112 µl, 0.8 mmol) was added. The reaction mixture was cooled to 0° C. and triphosgene (29.3 mg, 0.1 mmol) was added. After stirring the mixture at room temperature for 30 min, (5-chloropyridin-2-yl)methanamine hydrochloride (48 mg, 0.267 mmol) was added. The reaction mixture was stirred at room temperature overnight. The crude material was purified by flash chromatography (silica gel, 50 g, 0% to 80% Ethyl acetate in hexanes) to yield an off-white solid (38 mg, 33%). MS (ISP): 431.2 ({$^{35}$Cl} [M+H]$^+$), 433.2 ({$^{37}$Cl} [M+H]$^+$).

b) (S)-1-(6-Amino-5,6,7,8-tetrahydronaphthalen-2-yl)-3-((5-chloropyridin-2-yl)methyl)urea (S)-tert-Butyl 6-(3-((5-chloropyridin-2-yl)methyl)ureido)-1,2,3,4-tetrahydronaphthalen-2-ylcarbamate (38 mg, 0.051 mmol) was dissolved in dioxane (2 ml) to give a yellow solution. A solution of hydrochloric acid in dioxane (4M, 0.44 ml, 1.76 mmol) was added and the solution was shaken at 60° C. overnight. The reaction mixture was concentrated in vacuo and the residue was partitioned between ethyl acetate diluted sodium hydroxide solution. The organic layer was dried over sodium sulfate and concentrated in vacuo. The residue was purified by reversed phase HPLC (column YMC Triart C18, acetonitrile/water with 0.1% triethylamine) to yield an off-white solid (4 mg, 14%). MS (ISP): 331.1 ({$^{35}$Cl} [M+H]$^+$), 333.1 ({$^{37}$Cl} [M+H]$^+$).

Example 63

(S)-1-(6-Amino-5,6,7,8-tetrahydronaphthalen-2-yl)-3-(3-(trifluoromethoxy)benzyl)urea

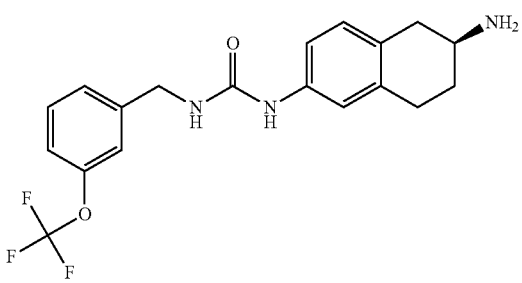 [SMILES: N[C@H]1CCc2cc(NC(=O)NCc3cccc(OC(F)(F)F)c3)ccc2C1]

The title compound was obtained in analogy to Example 16 using (3-(trifluoromethoxy)-benzylamine instead of 6-(trifluoromethyl)pyridin-3-amine in step a). Off-white solid, as hydrochloride salt. MS (ISP): 380.1 ([M+H]$^+$).

Example 64

(S)-1-(6-Amino-5,6,7,8-tetrahydronaphthalen-2-yl)-3-(4-ethylphenyl)urea

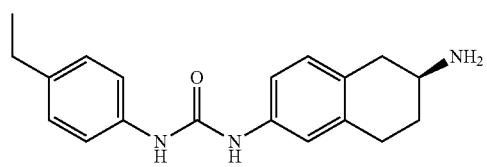 [SMILES: CCc1ccc(NC(=O)Nc2ccc3c(c2)CC[C@H](N)C3)cc1]

a) (S)-tert-Butyl 6-(3-(4-ethylphenyl)ureido)-1,2,3,4-tetrahydronaphthalen-2-ylcarbamate (S)-tert-Butyl 6-amino-1,2,3,4-tetrahydronaphthalen-2-ylcarbamate (70 mg, 0.267 mmol) was dissolved with dichloroethane (2 ml). 1-Ethyl-4-isocyanatobenzene (43.2 mg, 0.294 mmol) was added. The reaction mixture was shaken for 2 h at room temperature and for 1 h at 50° C. The reaction mixture was poured into ethyl acetate and extracted with diluted sodium hydroxide solution, diluted hydrochloric acid and brine. The organic layer was dried over sodium sulfate and concentrated in vacuo. The crude material was purified by flash chromatography (silica gel, 50 g, heptane/dichloromethane/methanol) to yield a white solid (100 mg, 92%). MS (ISP): 354.2 ([M−tBu+H]$^+$).

b) (S)-1-(6-Amino-5,6,7,8-tetrahydronaphthalen-2-yl)-3-(4-ethylphenyl)urea hydrochloride (S)-tert-Butyl 6-(3-(4-ethylphenyl)ureido)-1,2,3,4-tetrahydronaphthalen-2-ylcarbamate (100 mg, 0.244 mmol) was dissolved in dioxane (4 ml) and a 4 M solution of hydrogen chloride in dioxane (1.22 ml, 4.88 mmol) was added. The clear reaction mixture was shaken at 60° C. overnight. The dioxane was removed under reduced pressure and diethyl ether was added. The solid was filtered off and dried in vacuo. (S)-1-(6-Amino-5,6,7,8-tetrahydronaphthalen-2-yl)-3-(4-ethylphenyl)urea was obtained as hydrochloride salt, light brown solid (71 mg, 84%). MS (ISP): 310.2 ([M+H]⁺).

Example 65

(S)-1-(6-Amino-5,6,7,8-tetrahydronaphthalen-2-yl)-3-(4-(trifluoromethoxy)phenyl)urea

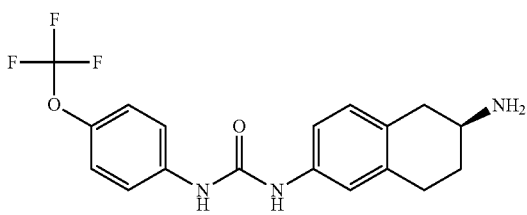 [SMILES: N[C@H]1CCc2cc(NC(=O)Nc3ccc(OC(F)(F)F)cc3)ccc2C1]

The title compound was obtained in analogy to Example 64 using 1-isocyanato-4-(trifluoromethoxy)benzene instead of 1-ethyl-4-isocyanatobenzene in step a). Light brown solid, as hydrochloride salt. MS (ISP): 366.1 ([M+H]⁺).

Example 66

(S)—N6-(4-Fluorophenyl)-1,2,3,4-tetrahydronaphthalene-2,6-diamine

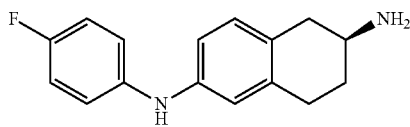 [SMILES: N[C@H]1CCc2cc(Nc3ccc(F)cc3)ccc2C1]

The title compound was obtained in analogy to Example 44 using 1-iodo-4-(trifluoromethyl)benzene instead of 1-fluoro-4-iodobenzene in step a). Off-white solid, as hydrochloride salt. MS (ISP): 257.1 ([M+H]⁺).

Example 67

(S)-1-(6-Amino-5,6,7,8-tetrahydronaphthalen-2-yl)-3-(3-methoxyphenyl)urea

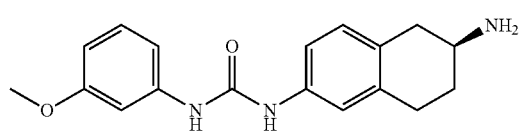 [SMILES: COc1cccc(NC(=O)Nc2ccc3c(c2)CC[C@H](N)C3)c1]

The title compound was obtained in analogy to Example 64 using 1-isocyanato-3-methoxybenzene instead of 1-ethyl-4-isocyanatobenzene in step a). Light brown solid, as hydrochloride salt. MS (ISP): 312.1 ([M+H]⁺).

Example 68

(S)—N6-(3-Chlorophenyl)-1,2,3,4-tetrahydronaphthalene-2,6-diamine

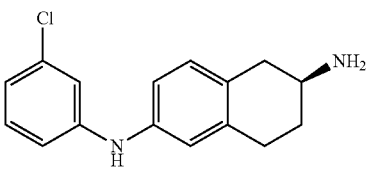 [SMILES: N[C@H]1CCc2cc(Nc3cccc(Cl)c3)ccc2C1]

The title compound was obtained in analogy to Example 44 using 1-chloro-3-iodobenzene instead of 1-fluoro-4-iodobenzene in step a). Light brown solid, as hydrochloride salt. MS (ISP): 273.1 ({³⁵Cl} [M+H]⁺), 275.1 ({³⁷Cl} [M+H]⁺).

Example 69

(S)-1-(6-Amino-5,6,7,8-tetrahydronaphthalen-2-yl)-3-(4-chlorobenzyl)urea

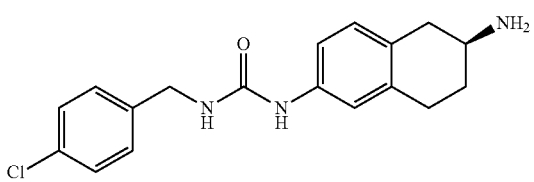

The title compound was obtained in analogy to Example 64 using 1-chloro-4-(isocyanatomethyl)benzene instead of 1-ethyl-4-isocyanatobenzene in step a). Light brown solid, as hydrochloride salt. MS (ISP): 330.1 ({³⁵Cl} [M+H]⁺), 332.1 ({³⁷Cl} [M+H]⁺).

Example 70

6-Amino-N-(3-chlorophenyl)-5,6,7,8-tetrahydronaphthalene-2-carboxamide

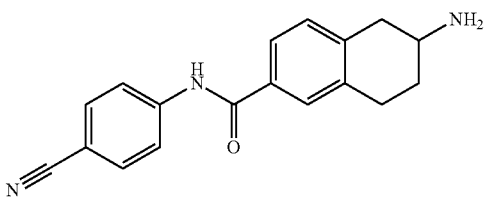 [SMILES: N#Cc1ccc(NC(=O)c2ccc3c(c2)CCC(N)C3)cc1]

The title compound was obtained in analogy to Example 55 using 4-aminobenzonitrile instead of 3-chloroaniline in step a). White solid, as hydrochloride salt. MS (ISP): 292.1 ([M+H]⁺).

Example 71

(S)-1-(6-Amino-5,6,7,8-tetrahydronaphthalen-2-yl)-3-(4-cyanophenyl)urea

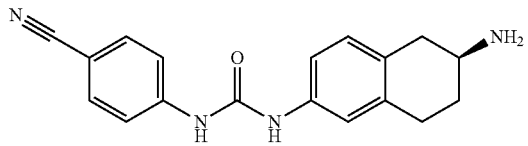 [SMILES: N#Cc1ccc(NC(=O)Nc2ccc3c(c2)CC[C@H](N)C3)cc1]

The title compound was obtained in analogy to Example 64 using 4-isocyanatobenzonitrile instead of 1-ethyl-4-isocyanatobenzene in step a). Brown solid, as hydrochloride salt. MS (ISP): 306.1 ([M+H]$^+$).

Example 72

(S)-1-(6-Amino-5,6,7,8-tetrahydronaphthalen-2-yl)-3-(4-cyclopropylphenyl)urea

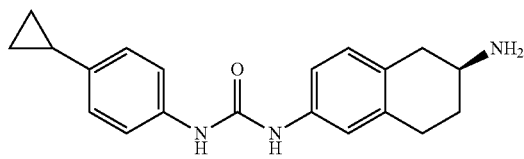 [SMILES: N[C@H]1CCc2cc(NC(=O)Nc3ccc(C4CC4)cc3)ccc2C1]

The title compound was obtained in analogy to Example 62 using 3-cyclopropylaniline instead of (5-chloropyridin-2-yl)methanamine hydrochloride in step a). White solid, MS (ISP): 322.2 ([M+H]$^+$).

Example 73

(S)—N6-(4-Cyclopropylphenyl)-1,2,3,4-tetrahydronaphthalene-2,6-diamine

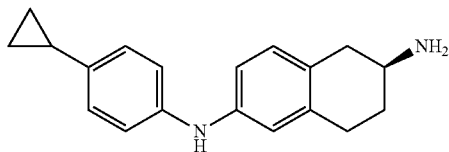 [SMILES: N[C@H]1CCc2cc(Nc3ccc(C4CC4)cc3)ccc2C1]

The title compound was obtained in analogy to Example 44 using 1-cyclopropyl-4-iodobenzene instead of 1-fluoro-4-iodobenzene in step a). Off-white solid, as hydrochloride salt. MS (ISP): 279.2 ([M+H]$^+$).

Example 74

(S)-1-(6-Amino-5,6,7,8-tetrahydronaphthalen-2-yl)-3-(4-chlorophenyl)urea

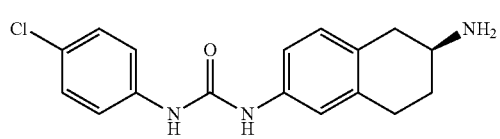 [SMILES: N[C@H]1CCc2cc(NC(=O)Nc3ccc(Cl)cc3)ccc2C1]

The title compound was obtained in analogy to Example 64 using 1-chloro-4-isocyanatobenzene instead of 1-ethyl-4-isocyanatobenzene in step a). Off-white solid, MS (ISP): 316.2 ({$^{35}$Cl}[M+H]$^+$), 318.1 ({$^{37}$Cl} [M+H]$^+$).

Example 75

(S)—N6-(4-Chlorobenzyl)-1,2,3,4-tetrahydronaphthalene-2,6-diamine

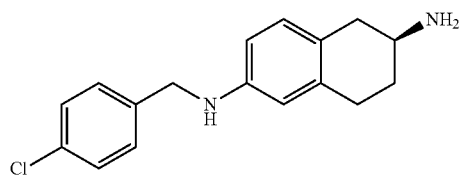 [SMILES: N[C@H]1CCc2cc(NCc3ccc(Cl)cc3)ccc2C1]

a) (S)-tert-Butyl 6-(4-chlorobenzylamino)-1,2,3,4-tetrahydronaphthalen-2-ylcarbamate In a 25 mL round-bottomed flask, (S)-tert-butyl 6-amino-1,2,3,4-tetrahydronaphthalen-2-ylcarbamate (100 mg, 0.38 mmol) was dissolved with methanol (6 ml). 4-Chlorobenzaldehyde (64 mg, 0.45 mmol) and sodium cyanoborohydride (36 mg, 0.57 mmol) were added. The reaction mixture was stirred at 40° C. overnight. The reaction mixture was poured into ethyl acetate and extracted with diluted hydrochloric acid and brine. The organic layer was dried over sodium sulfate and concentrated in vacuo. The crude material was purified by flash chromatography (silica gel, 50 g, 0% to 40% Ethyl acetate in hexanes) to yield a white solid, (72 mg, 49%). MS (ISP): 331.3 ({$^{35}$Cl} [M+H−tBu]$^+$), 333.1 ({$^{37}$Cl} [M+H−tBu]$^+$).

b) (S)—N6-(4-Chlorobenzyl)-1,2,3,4-tetrahydronaphthalene-2,6-diamine (S)-tert-Butyl 6-(4-chlorobenzylamino)-1,2,3,4-tetrahydronaphthalen-2-ylcarbamate (70 mg, 0.181 mmol) was dissolved in acetonitrile (2 ml). Water (3 ml) and a trifluoroacetic acid (206 mg, 139 µl, 1.81 mmol) were added. The reaction mixture was shaken for 2 h at 80° C. The reaction mixture was poured into ethyl acetate and extracted with 1 M sodium hydroxide solution and brine. The organic layer was dried over sodium sulfate and concentrated in vacuo. The crude material was purified by flash chromatography (silica gel, 20 g, heptane/dichloromethane/aq. ammonia/methanol) to yield a white solid (40 mg, 77%). MS (ISP): 287.1 ({$^{35}$Cl} [M+H]$^+$), 289.1 ({$^{37}$Cl} [M+H]$^+$).

Example 76

(S)—N-(6-Amino-1-chloro-5,6,7,8-tetrahydronaphthalen-2-yl)-6-chloronicotinamide

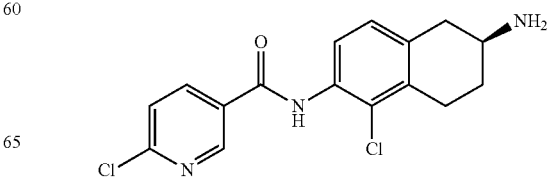

a) (S)-tert-Butyl 6-amino-5-chloro-1,2,3,4-tetrahydronaphthalen-2-ylcarbamate (S)-tert-Butyl 6-amino-1,2,3,4-tetrahydronaphthalen-2-ylcarbamate (200 mg, 0.762 mol) was dissolved in N,N-dimethylformamide (1.5 ml). N-Chlorosuccinimide (102 mg, 0.762 mmol) was added at 0° C. The reaction mixture was stirred at room temperature for 3 h. The reaction mixture was poured into ethyl acetate and extracted with water and brine. The organic layer was dried over sodium sulfate and concentrated in vacuo. The crude material was purified by flash chromatography (silica gel, 50 g, 0% to 60% ethyl acetate in hexanes) to yield a yellow solid (55 mg, 24%). MS (ISP): 241.1 ($\{^{35}Cl\}$ [M+H-tBu]$^+$), 243.1 ($\{^{37}Cl\}$ [M+H-tBu]$^+$).

b) (S)-tert-Butyl 5-chloro-6-(6-chloronicotinamido)-1,2,3,4-tetrahydronaphthalen-2-ylcarbamate 6-Chloronicotinic acid (42.2 mg, 0.268 mmol) was dissolved in dichloroethane (2 ml). Oxalyl chloride (113 mg, 78.2 µl, 0.893 mmol) and N,N-dimethylformamide (1 drop) were added. The reaction mixture was stirred 30 min at room temperature to give a yellow solution. The reaction mixture was concentrated in vacuo. This acid chloride was dissolved in dichloroethane (1 ml), added to a solution of (S)-tert-butyl 6-amino-5-chloro-1,2,3,4-tetrahydronaphthalen-2-ylcarbamate (53 mg, 0.179 mmol), N,N-diisopropylethylamine (46.2 mg, 62.4 µl, 0.357 mmol) in dioxane (2 ml). The reaction mixture was stirred at room temperature overnight. The reaction mixture was poured into ethyl acetate and extracted with 0.5 M sodium bicarbonate solution, 0.5M hydrochloric acid and brine. The organic layer was dried over sodium sulfate and concentrated in vacuo. The crude material was purified by flash chromatography (silica gel, 20 g, 0% to 70% ethyl acetate in hexanes) to yield an off-white solid (47 mg, 60%). MS (ISP): 434.3 ($\{^{35}Cl, ^{35}Cl\}$ [M-H]$^+$), 436.4 ($\{^{35}Cl, ^{37}Cl\}$ [M-H]$^-$).

c) (S)—N-(6-Amino-1-chloro-5,6,7,8-tetrahydronaphthalen-2-yl)-6-chloronicotinamide (S)-tert-Butyl 5-chloro-6-(6-chloronicotinamido)-1,2,3,4-tetrahydronaphthalen-2-ylcarbamate (46 mg, 0.105 mmol) was dissolved in acetonitrile (2 ml) and water (4 ml). Trifluoroacetic acid (240 mg, 162 µl, 2.11 mmol) was added. The reaction mixture was shaken at 80° C. overnight to give a colorless solution. The reaction mixture was poured into ethyl acetate and extracted with 1 M sodium hydroxide solution and brine. The organic layer was dried over sodium sulfate and concentrated in vacuo. The crude material was purified by flash chromatography (silica gel, 20 g, heptane/dichloromethane/aq. ammonia/methanol) to yield an off-white solid (47 mg, 53%). MS (ISP): 336.1 ($\{^{35}Cl, ^{35}Cl\}$ [M+H]$^+$), 338.1 ($\{^{35}Cl, ^{37}Cl\}$ [M+H]$^+$).

Example 77

(S)—N-(6-Amino-5,6,7,8-tetrahydronaphthalen-2-yl)-4-chlorobenzenesulfonamide

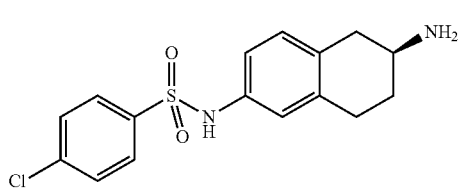 [SMILES: N[C@H]1CCc2cc(NS(=O)(=O)c3ccc(Cl)cc3)ccc2C1]

a) (S)-tert-Butyl 6-(4-chlorophenylsulfonamido)-1,2,3,4-tetrahydronaphthalen-2-ylcarbamate In a sealed tube, (S)-tert-butyl 6-amino-1,2,3,4-tetrahydronaphthalen-2-ylcarbamate (70 mg, 0.267 mmol) and 4-chlorobenzene-1-sulfonyl chloride (56.3 mg, 0.267 µmol) were combined with dioxane (2 ml) to give a light yellow solution. Diisopropylamine (38 mg, 51.3 µl, 0.294 mmol) was added and the reaction mixture was heated to 60° C. and stirred for 6 h. The crude material was purified by flash chromatography (silica gel, 50 g, 0% to 70% Ethyl acetate in heptane) to yield and off-white solid. Further purification by reversed phase HPLC (column YMC Triart C18, gradient acetonitrile/water with 0.1% triethylamine) yielded a white solid (38 mg, 33%). MS (ISP): 435.1 ($\{^{35}Cl\}$ [M-H]$^-$), 437.1 ($\{^{37}Cl\}$ [M-H]$^+$).

b) (S)—N-(6-amino-5,6,7,8-tetrahydronaphthalen-2-yl)-4-chlorobenzenesulfonamide (S)-tert-Butyl 6-(4-chlorophenylsulfonamido)-1,2,3,4-tetrahydronaphthalen-2-ylcarbamate (38 mg, 0.087 mmol) was dissolved in acetonitrile (2 ml). Water (4 ml) and trifluoroacetic acid (222 mg, 150 µl, 1.95 mmol) were added. The reaction mixture was shaken for 2 h at 80° C. The reaction mixture was poured into ethyl acetate and extracted with 1 M sodium hydroxide solution and brine. The organic layer was dried over sodium sulfate and concentrated in vacuo. The crude material was purified by flash chromatography (silica gel, 20 g, heptane/dichloromethane/aq. ammonia/methanol) to yield an off-white solid (7 mg, 23%). MS (ISP): 337.1 ($\{^{35}Cl\}$ [M+H]$^+$), 339.1 ($\{^{37}Cl\}$ [M+H]$^+$).

Example 78

(R)-6-Amino-N-(3-(trifluoromethoxy)phenyl)-5,6,7,8-tetrahydronaphthalene-2-carboxamide

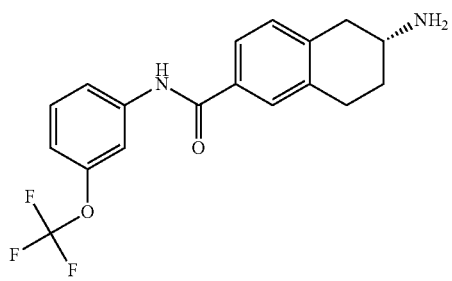 [SMILES: N[C@@H]1CCc2cc(C(=O)Nc3cccc(OC(F)(F)F)c3)ccc2C1]

The title compound was obtained in analogy to Example 55 using (R)-6-(tert-butoxycarbonylamino)-5,6,7,8-tetrahydronaphthalene-2-carboxylic acid instead of 6-(tert-butoxycarbonylamino)-5,6,7,8-tetrahydronaphthalene-2-carboxylic acid in step a). To obtain (R)-6-(tert-butoxycarbonylamino)-5,6,7,8-tetrahydronaphthalene-2-carboxylic acid a chiral separation of methyl 6-(tert-butoxycarbonylamino)-5,6,7,8-tetrahydronaphthalene-2-carboxylate was performed using a column Reprosil Chiral NR and a 15% isopropanol/heptane gradient. White solid, as hydrochloride salt. MS (ISP): 351.3 ([M+H]$^+$).

Example 79

(S)-6-Amino-N-(3-(trifluoromethoxy)phenyl)-5,6,7,8-tetrahydronaphthalene-2-carboxamide

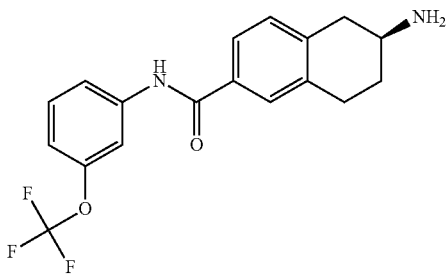 [SMILES: N[C@H]1CCc2cc(C(=O)Nc3cccc(OC(F)(F)F)c3)ccc2C1]

The title compound was obtained in analogy to Example 55 using (S)-6-(tert-butoxycarbonylamino)-5,6,7,8-tetrahydronaphthalene-2-carboxylic acid instead of 6-(tert-butoxycarbonylamino)-5,6,7,8-tetrahydronaphthalene-2-carboxylic acid in step a). To obtain (S)-6-(tert-butoxycarbonylamino)-5,6,7,8-tetrahydronaphthalene-2-carboxylic acid a chiral separation of methyl 6-(tert-butoxycarbonylamino)-5,6,7,8-tetrahydronaphthalene-2-carboxylate was performed using a column Reprosil Chiral NR and a 15% isopropanol/heptane gradient. White solid, as hydrochloride salt. MS (ISP): 351.3 ([M+H]$^+$).

Example 80

(R)—N7-(5-(Trifluoromethyl)pyrimidin-2-yl)chroman-3,7-diamine

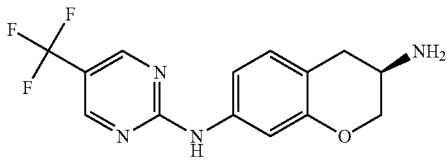 [SMILES: N[C@H]1COc2cc(Nc3ncc(C(F)(F)F)cn3)ccc2C1]

a) 7-Bromo-2H-chromene-3-carboxamide

7-Bromo-2H-chromene-3-carbonitrile (9 g, 38.1 mmol) was dissolved in acetic acid (72.0 ml, 1.26 mol) and to the stirred solution, concentrated sulfuric acid (33.7 g, 18.3 ml, 343 mmol) was added. The reaction mixture was stirred at 100° C. for one hour. At 30° C., 1.2 ml aqueous isopropanol (2:1, water:isopropanol) was added dropwise and the reaction mixture was cooled to 0° C. and stirred at this temperature for 2 hours. The solid was filtrated and washed with cold water and then dried at 40° C. under high vacuum to give 7-bromo-2H-chromene-3-carboxamide (9.48 g, 37.3 mmol, 98% yield) as yellow solid. MS (ISP): 254.0 ({$^{79}$Br}[M+H]$^+$), 256.0 ({$^{81}$Br}[M+H]$^+$).

b) Methyl 7-bromo-2H-chromen-3-ylcarbamate

7-Bromo-2H-chromene-3-carboxamide (8.3 g, 32.7 mmol) was dissolved in hot methanol (325 ml). The solution was cooled to room temperature and sodium hypochlorite solution (10%, 26.7 g, 22.2 ml, 35.9 mmol) was added. The mixture was heated at 70° C. for 30 min, then the mixture was poured into water and left to stir at room temperature for 10 min, after which the solid was filtrated and washed with water. The crude material was purified by flash chromatography (silica gel, 330 g, 0% to 40% ethyl acetate in heptane) and then recrystallised from ethanol/water to give methyl 7-bromo-2H-chromen-3-ylcarbamate (5.7 g, 20.1 mmol, 61% yield) as a light brown solid. MS (ISP): 284.0 ({$^{79}$Br}[M+H]$^+$), 286.0 ({$^{81}$Br}[M+H]$^+$).

c) (R)-Methyl 7-bromochroman-3-ylcarbamate

In a glove box an autoclave was filled with methyl 7-bromo-2H-chromen-3-ylcarbamate (2.29 g, 8 mmol) and methanol (25 ml). A solution of diacetato[(R)-(−)-2,2-bis(ditolyl-phosphino)-1,1'-binaphthyl]ruthenium(II) (Ru(OAc)$_2$((R)-p-Tol-BINAP), 72 mg, 80 µmol) in methanol (3 ml) and sulfuric acid (165 mg, 90 µl, 1.61 mmol) were added. The mixture was hydrogenated at 20 bar H$_2$ atmosphere at room temperature for 4 hours. For work-up the reaction mixture was transferred to a round bottom flask and the solvent was evaporated. The residue was partitioned between ethyl acetate and sodium bicarbonate solution. The organic layer was washed with brine and dried over magnesium sulfate. The crude material was purified by flash chromatography (silica gel, 50 g, 10% to 40% Ethyl acetate in heptane) to give (R)-methyl 7-bromochroman-3-ylcarbamate (2.26 g, 99% yield) as a green solid. MS (ISP): 286.1 ({$^{79}$Br}[M+H]$^+$), 288.1 ({$^{81}$Br}[M+H]$^+$).

d) (R)-tert-Butyl 7-bromochroman-3-ylcarbamate (R)-Methyl 7-bromochroman-3-ylcarbamate (3.19 g, 11.1 mmol) was dissolved in methanol (50 ml) and 40% KOH in water (15.6 g, 111 mmol) was added. The reaction mixture was heated at 70° C. for 92 h. The methanol was removed in vacuo and the residue was partitioned between water and dichloromethane. The organic extracts were combined, dried over magnesium sulfate, filtered and concentrated in vacuo to give crude (R)-7-bromochroman-3-amine (2.45 g) which was dissolved in dichloromethane (36.5 ml). Di-tert-butyl dicarbonate (2.39 g, 11.0 mmol) and diisopropylethylamine (2.12 g, 2.81 ml, 16.4 mmol) were added at room temperature. The mixture was stirred overnight and the solvent was evaporated under reduced pressure. The residue was extracted with ethyl acetate and washed with 1 N aqueous hydrochloric acid, saturated sodium bicarbonate solution and brine. It was dried with magnesium sulfate, filtered and concentrated under reduced pressure. The crude material was purified by flash chromatography (silica gel, 50 g, 10% to 30% ethyl acetate in heptane) to give (R)-tert-butyl 7-bromochroman-3-ylcarbamate (3.16 g, 88% yield) as a white solid. MS (ISP): 272.1 ({$^{79}$Br} [M−tBu+H]$^+$), 274.1 ({$^{81}$Br} [M−tBu+H]$^+$).

e) (R)-tert-Butyl 7-(diphenylmethyleneamino)chroman-3-ylcarbamate

The title compound was obtained in analogy to Example 10d using (R)-tert-butyl 7-bromochroman-3-ylcarbamate instead of tert-butyl 7-bromochroman-3-ylcarbamate. Yellow foam. MS (ISP): 429.4 ([M+H]$^+$).

f) (R)-tert-Butyl 7-aminochroman-3-ylcarbamate

The title compound was obtained in analogy to Example 10e using (R)-tert-butyl 7-(diphenylmethyleneamino)chroman-3-ylcarbamate instead of tert-butyl 7-(diphenylmethyleneamino)chroman-3-ylcarbamate. Off-white solid. MS (ISP): 209.1 ([M−tBu+H]$^+$).

g) (R)-tert-Butyl 7-(5-(trifluoromethyl)pyrimidin-2-ylamino)chroman-3-ylcarbamate In a sealed tube, (R)-tert-butyl 7-aminochroman-3-ylcarbamate (50 mg, 0.19 mmol), 2-chloro-5-(trifluoromethyl)

pyrimidine (38 mg, 0.21 mmol) and diisopropyl ethylamine (39 mg, 0.053 ml, 0.30 mmol) were dissolved in 2-propanol (1 ml). The reaction mixture was capped and stirred for 4 h at 90° C. The crude material was purified by flash chromatography (silica gel, 50 g, 10% to 30% ethyl acetate in hexanes) to yield a yellow solid (58 mg, 74%). MS (ISP): 355.1 ([M−tBu+H]$^+$).

h) (R)—N7-(5-(Trifluoromethyl)pyrimidin-2-yl) chroman-3,7-diamine

In a sealed tube, (R)-tert-butyl 7-(5-(trifluoromethyl)pyrimidin-2-ylamino)chroman-3-ylcarbamate (53 mg, 0.129 mmol) was combined with dioxane (0.5 ml) to give a yellow solution. A solution of hydrochloric acid in dioxane (4M, 0.48 ml, 1.9 mmol) was added and the solution was shaken at 60° C. for 2.5 hours. The reaction mixture was concentrated in vacuo and diethyl ether was added. The solid was separated by filtration through sintered glass and dried in vacuo to give (R)—N7-(5-(trifluoromethyl)pyrimidin-2-yl) chroman-3,7-diamine as hydrochloride salt, yellow solid (35 mg, 77%). MS (ISP): 311.1 ([M+H]$^+$).

Example 81

(R)—N-(3-Aminochroman-7-yl)-5-ethoxy-4-methyl-1H-pyrazole-3-carboxamide

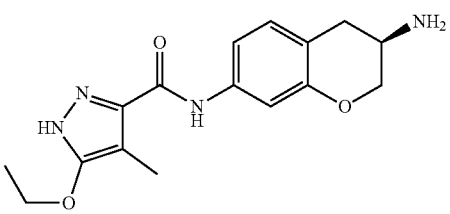 [SMILES: CCOc1[nH]nc(C(=O)Nc2ccc3c(c2)OC[C@H](N)C3)c1C]

The title compound was obtained in analogy to Example 39 using 5-ethoxy-4-methyl-1H-pyrazole-3-carboxylic acid instead of 2-fluoronicotinic acid and (R)-tert-butyl 7-aminochroman-3-ylcarbamate instead of (S)-tert-butyl 6-amino-1,2,3,4-tetrahydronaphthalen-2-ylcarbamate in step a). Light-yellow solid, as hydrochloride salt. MS (ISP): 317.2 ([M+H]$^+$).

Example 82

(R)—N-(3-Aminochroman-7-yl)-4-chloropyrimidine-2-carboxamide

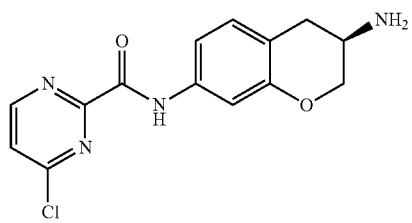 [SMILES: N[C@H]1COc2cc(NC(=O)c3nccc(Cl)n3)ccc2C1]

The title compound was obtained in analogy to Example 39 using 4-chloropyrimidine-2-carboxylic acid instead of 2-fluoronicotinic acid and (R)-tert-butyl 7-aminochroman-3-ylcarbamate instead of (S)-tert-butyl 6-amino-1,2,3,4-tetrahydronaphthalen-2-ylcarbamate in step a). Light-yellow solid, as hydrochloride salt. MS (ISP): 305.1 ({$^{35}$Cl}[M+H]$^+$), 307.1 ({$^{37}$Cl}[M+H]$^+$).

Example 83

(R)—N-(3-Aminochroman-7-yl)-4-(2-methylthiazol-4-yl)benzamide

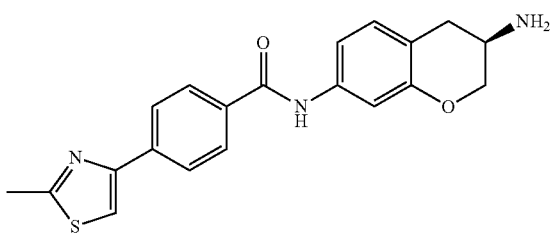 [SMILES: Cc1nc(-c2ccc(C(=O)Nc3ccc4c(c3)OC[C@H](N)C4)cc2)cs1]

The title compound was obtained in analogy to Example 39 using 4-(2-methylthiazol-4-yl)benzoic acid instead of 2-fluoronicotinic acid and (R)-tert-butyl 7-aminochroman-3-ylcarbamate instead of (S)-tert-butyl 6-amino-1,2,3,4-tetrahydronaphthalen-2-ylcarbamate in step a). Off-white solid, as hydrochloride salt. MS (ISP): 366.2 ([M+H]$^+$).

Example 84

(R)—N-(3-Aminochroman-7-yl)-5-(trifluoromethyl)pyrimidine-2-carboxamide

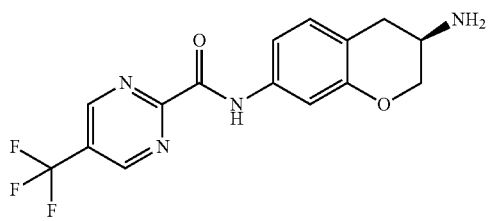 [SMILES: N[C@H]1COc2cc(NC(=O)c3ncc(C(F)(F)F)cn3)ccc2C1]

The title compound was obtained in analogy to Example 39 using 5-(trifluoromethyl)pyrimidine-2-carboxylic acid instead of 2-fluoronicotinic acid and (R)-tert-butyl 7-aminochroman-3-ylcarbamate instead of (S)-tert-butyl 6-amino-1,2,3,4-tetrahydronaphthalen-2-ylcarbamate in step a). Light yellow solid, as hydrochloride salt. MS (ISP): 339.1 ([M+H]$^+$).

Example 85

(R)—N-(3-Aminochroman-7-yl)-1-methyl-5-(thiophen-2-yl)-1H-pyrazole-3-carboxamide

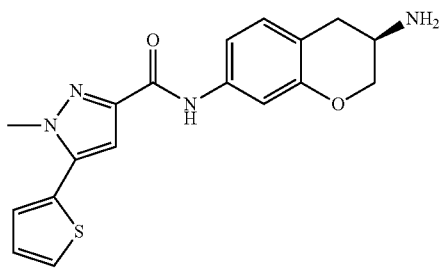 [SMILES: Cn1nc(C(=O)Nc2ccc3c(c2)OC[C@H](N)C3)cc1-c1cccs1]

The title compound was obtained in analogy to Example 39 using 1-methyl-5-(thiophen-2-yl)-1H-pyrazole-3-carboxylic acid instead of 2-fluoronicotinic acid and (R)-tert-butyl 7-aminochroman-3-ylcarbamate instead of (S)-tert-butyl 6-amino-1,2,3,4-tetrahydronaphthalen-2-ylcarbamate in step a). Light yellow solid, as hydrochloride salt. MS (ISP): 355.1 ([M+H]+).

Example 86

(R)—N-(3-Aminochroman-7-yl)-4-cyano-3-fluorobenzamide

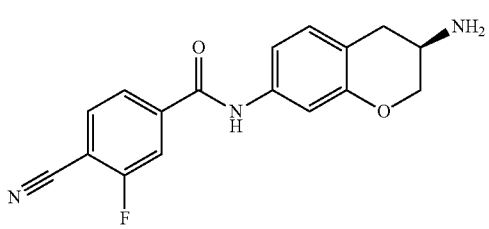 [SMILES: N#Cc1ccc(C(=O)Nc2ccc3c(c2)OC[C@H](N)C3)cc1F]

The title compound was obtained in analogy to Example 39 using 4-cyano-3-fluorobenzoic acid instead of 2-fluoronicotinic acid and (R)-tert-butyl 7-aminochroman-3-ylcarbamate instead of (S)-tert-butyl 6-amino-1,2,3,4-tetrahydronaphthalen-2-ylcarbamate in step a). Orange solid, as hydrochloride salt. MS (ISP): 312.1 ([M+H]+).

Example 87

(R)—N-(3-Aminochroman-7-yl)-3,4-difluorobenzamide

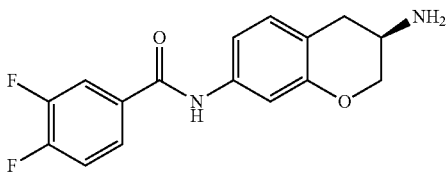 [SMILES: N[C@H]1COc2cc(NC(=O)c3ccc(F)c(F)c3)ccc2C1]

The title compound was obtained in analogy to Example 39 using 3,4-difluorobenzoic acid instead of 2-fluoronicotinic acid and (R)-tert-butyl 7-aminochroman-3-ylcarbamate instead of (S)-tert-butyl 6-amino-1,2,3,4-tetrahydronaphthalen-2-ylcarbamate in step a). Light brown solid, as hydrochloride salt. MS (ISP): 305.2 ([M+H]+).

Example 88

(R)—N-(3-Aminochroman-7-yl)-3-ethyl-4-methyl-1H-pyrazole-5-carboxamide

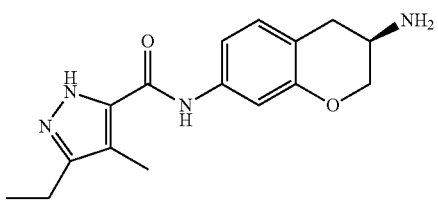 [SMILES: CCc1n[nH]c(C(=O)Nc2ccc3c(c2)OC[C@H](N)C3)c1C]

The title compound was obtained in analogy to Example 39 using 3-ethyl-4-methyl-1H-pyrazole-5-carboxylic acid instead of 2-fluoronicotinic acid and (R)-tert-butyl 7-aminochroman-3-ylcarbamate instead of (S)-tert-butyl 6-amino-1,2,3,4-tetrahydronaphthalen-2-ylcarbamate in step a). Off-white solid, as hydrochloride salt. MS (ISP): 301.2 ([M+H]+).

Example 89

(R)—N-(3-Aminochroman-7-yl)-2-chloro-6-methylisonicotinamide

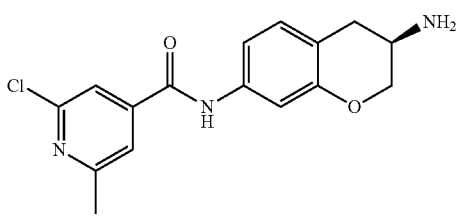

The title compound was obtained in analogy to Example 39 using 2-chloro-6-methylisonicotinic acid instead of 2-fluoronicotinic acid and (R)-tert-butyl 7-aminochroman-3-ylcarbamate instead of (S)-tert-butyl 6-amino-1,2,3,4-tetrahydronaphthalen-2-ylcarbamate in step a). Yellow solid, as hydrochloride salt. MS (ISP): 318.2 ({$^{35}$Cl} [M+H]+), 320.2 ({$^{37}$Cl} [M+H]+).

Example 90

(R)—N-(3-Aminochroman-7-yl)-2-(trifluoromethyl)isonicotinamide

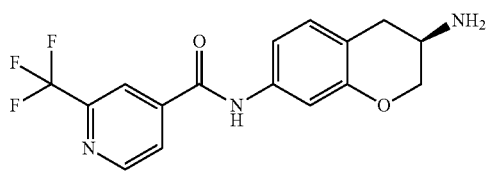 [SMILES: N[C@H]1COc2cc(NC(=O)c3ccnc(C(F)(F)F)c3)ccc2C1]

The title compound was obtained in analogy to Example 39 using 2-(trifluoromethyl)isonicotinic acid instead of 2-fluoronicotinic acid and (R)-tert-butyl 7-aminochroman-3-ylcarbamate instead of (S)-tert-butyl 6-amino-1,2,3,4-tetrahydronaphthalen-2-ylcarbamate in step a). Off-white solid, as hydrochloride salt. MS (ISP): 338.2 ([M+H]+).

Example 91

(R)—N-(3-Aminochroman-7-yl)-2,6-dichloroisonicotinamide

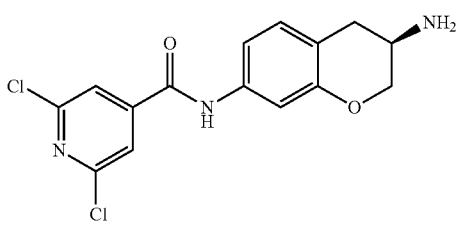

The title compound was obtained in analogy to Example 39 using 2,6-dichloroisonicotinic acid instead of 2-fluoronicotinic acid and (R)-tert-butyl 7-aminochroman-3-ylcarbamate instead of (S)-tert-butyl 6-amino-1,2,3,4-tetrahydronaphthalen-2-ylcarbamate in step a). Off-white solid, as hydrochloride salt. MS (ISP): 338.2 ($\{^{35}Cl\}$ [M+H]$^+$), 340.2 ($\{^{37}Cl\}$ [M+H]$^+$).

Example 92

(R)—N-(3-Aminochroman-7-yl)-4-bromo-5-(2,2-difluoroethoxy)-1-ethyl-1H-pyrazole-3-carboxamide

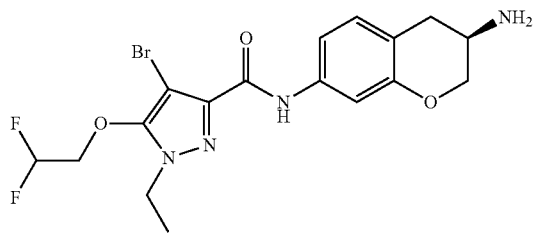 [SMILES: CCn1nc(C(=O)Nc2ccc3c(c2)OC[C@H](N)C3)c(Br)c1OCC(F)F]

The title compound was obtained in analogy to Example 39 using 4-bromo-5-(2,2-difluoroethoxy)-1-ethyl-1H-pyrazole-3-carboxylic acid instead of 2-fluoronicotinic acid and (R)-tert-butyl 7-aminochroman-3-ylcarbamate instead of (S)-tert-butyl 6-amino-1,2,3,4-tetrahydronaphthalen-2-ylcarbamate in step a). White solid, as hydrochloride salt. MS (ISP): 445.1 ($\{^{79}Br\}$ [M+H]$^+$), 447.1 ($\{^{81}Br\}$ [M+H]$^+$).

Example 93

(R)—N7-(5-Chloropyrimidin-2-yl)chroman-3,7-diamine

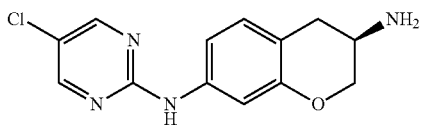 [SMILES: N[C@H]1COc2cc(Nc3ncc(Cl)cn3)ccc2C1]

The title compound was obtained in analogy to Example 80 using 2,5-dichloropyrimidine instead of 2-chloro-5-(trifluoromethyl)pyrimidine in step g). Yellow solid, as hydrochloride salt. MS (ISP): 277.1 ($\{^{35}Cl\}$ [M+H]$^+$), 279.1 ($\{^{37}Cl\}$ [M+H]$^+$).

Example 94

(S)—N6-(3-Methoxyphenyl)-1,2,3,4-tetrahydronaphthalene-2,6-diamine

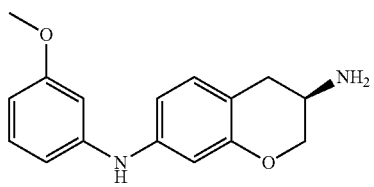 [SMILES: COc1cccc(Nc2ccc3c(c2)OC[C@H](N)C3)c1]

The title compound was obtained in analogy to Example 44 using 1-iodo-3-methoxy-benzene instead of 1-iodo-4-(trifluoromethyl)benzene in step a). Light brown solid, as hydrochloride salt. MS (ISP): 269.2 ([M+H]$^+$).

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable EC$_{50}$ for a culture period of 15 passages were used for all subsequent studies.

Radioligand Binding Assay on Rat TAAR1

Membrane Preparation and Radioligand Binding.

HEK-293 cells stably expressing rat TAAR1 were maintained at 37° C. and 5% CO$_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without Ca$^{2+}$ and Mg$^{2+}$), pelleted at 1'000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (K$_d$) was determined via a saturation curve. The TAAR1 radioligand $^3$[H]—(S)-4-[(ethyl-phenyl-amino)-methyl]-4,5-dihydro-oxazol-2-ylamine (described in WO 2008/098857) was used at a concentration equal to the calculated K$_d$ value, that was usually around 2.3 nM, resulting in the binding of approximately 0.2% of the radioligand and a specific binding representing approximately 85% of the total binding. Nonspecific binding was defined as the amount of [H]—(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TrefflLab), and 180 µl of HEPES-NaOH (20 mM, pH 7.4) containing MgCl$_2$ (10 mM) and CaCl$_2$ (2 mM) (binding buffer), 300 µl of the radioligand $^3$[H]—(S)-4-[(ethyl-phenyl-amino)-methyl]-4,5-dihydro-oxazol-2-ylamine at a concentration of 3.3×K$_d$ in nM and 500 µl of the membranes (resuspended at 50 g protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the radioactivity counted using a TopCount Microplate Scintillation Counter (Packard Instrument Company).

Radioligand Binding Assay on Mouse TAAR1

Membrane Preparation and Radioligand Binding.

HEK-293 cells stably expressing mouse TAAR1 were maintained at 37° C. and 5% CO$_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without Ca$^{2+}$ and Mg$^{2+}$), pelleted at 1'000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (K$_d$) was determined via a saturation curve. The TAAR1 radioligand $^3$[H]—(S)-4-[(ethyl-phenyl-amino)-methyl]-4,5-dihydro-oxazol-2-ylamine (described in WO 2008/098857) was used at a concentration equal to the calculated K$_d$ value, that was usually around 0.7 nM, resulting in the binding of approximately 0.5% of the radioligand and a specific binding representing approximately 70% of the total binding. Nonspecific binding was defined as the amount of $^3$[H]—(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TrefflLab), and 180 µl of HEPES-NaOH (20 mM, pH 7.4) containing MgCl$_2$ (10 mM) and CaCl$_2$ (2 mM) (binding buffer), 300 µl of the radioligand $^3$[H]—(S)-4-[(ethyl-phenyl-amino)-methyl]-4,5-dihydro-oxazol-2-ylamine at a concentration of 3.3×K$_d$ in nM and 500 µl of the membranes (resuspended at 60 g protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the radioactivity counted using a TopCount Microplate Scintillation Counter (Packard Instrument Company).

The compounds show a K$_i$ value in mouse or rat on TAAR1 (in µM) as shown in the table below.

| Example | Ki (µM) mouse/rat |
|---|---|
| 1 | 0.0159/0.0072 |
| 2 | 0.0077/0.0042 |
| 3 | 0.0132/0.0035 |
| 4 | 0.0914/0.0055 |
| 5 | 0.0067/0.0021 |
| 6 | 0.2319/0.0544 |
| 7 | 0.0318/0.0198 |
| 8 | 0.0198/0.01 |
| 9 | 0.0805 0.1138 |
| 10 | 0.0111/0.0034 |
| 11 | 0.1875/0.0096 |
| 12 | 0.0581/0.0436 |
| 13 | 1.4481/0.2413 |
| 14 | 0.0092/0.0069 |
| 15 | 1.9743/0.5998 |
| 16 | 0.0045/0.0023 |
| 17 | 0.1107/0.1475 |
| 18 | 0.7102/0.2324 |
| 19 | 0.0187/0.0216 |
| 20 | 0.0265/0.0237 |
| 21 | 0.0344/0.0513 |
| 22 | 0.0033/0.0016 |
| 23 | 0.0213/0.0068 |
| 24 | 0.0011/0.0003 |
| 25 | 0.0007/0.0003 |
| 26 | 0.0049/0.0199 |
| 27 | 0.0028/0.0037 |
| 28 | 0.0007/0.0003 |
| 29 | 0.0012 0.0005 |
| 30 | 0.0709/0.0191 |
| 31 | 0.0247/0.0434 |
| 32 | 0.1054/0.3094 |
| 33 | 0.021/0.0865 |
| 34 | 0.0054/0.0039 |
| 35 | 0.0055/0.035 |
| 36 | 0.0318/0.0898 |
| 37 | 0.0356/0.0904 |
| 38 | 0.0032/0.0021 |
| 39 | 0.4758/0.1401 |
| 40 | 0.0172/0.0165 |
| 41 | 0.0031/0.0031 |
| 42 | 0.0035/0.0019 |
| 43 | 0.0006/0.001 |
| 44 | 0.0113/0.0048 |
| 45 | 0.0117/0.0063 |
| 46 | 0.0042/0.0022 |
| 47 | 0.1157/0.0505 |
| 48 | 0.0232/0.0139 |
| 49 | 0.0144/0.0235 |
| 50 | 0.0147/0.0108 |
| 51 | 0.0062/0.0046 |
| 52 | 0.0128/0.0016 |
| 53 | 0.006/0.0083 |
| 54 | 0.0107/0.091 |
| 55 | 0.003/0.0017 |
| 56 | 0.0155 0.0456 |
| 57 | 0.0116/0.0142 |
| 58 | 0.0569/0.0964 |
| 59 | 0.0018/0.0109 |
| 60 | 0.0096/0.0213 |
| 61 | 0.0071/0.0049 |
| 62 | 0.0355 0.095 |
| 63 | 0.002 0.0039 |
| 64 | 0.003/0.0026 |
| 65 | 0.0012/0.0003 |
| 66 | 0.1711/0.024 |
| 67 | 0.0075/0.0044 |
| 68 | 0.019/0.0099 |
| 69 | 0.0029 |

-continued

| Example | Ki (μM) mouse/rat |
|---|---|
|  | 0.0085 |
| 70 | 0.0044/0.0032 |
| 71 | 0.0258/0.0206 |
| 72 | 0.001/0.0009 |
| 73 | 0.01/0.0081 |
| 74 | 0.001/0.0005 |
| 75 | 0.0048/0.0153 |
| 76 | >1.51/0.302 |
| 77 | 0.0755/0.264 |
| 78 | 0.0073/0.0044 |
| 79 | 0.0008/0.0009 |
| 80 | 0.0163/0.0196 |
| 81 | 0.0082/0.0277 |
| 82 | 0.1729/0.5111 |
| 83 | 0.0018/0.0034 |
| 84 | 0.0371/0.0758 |
| 85 | 0.0009/0.0061 |
| 86 | 0.0026/0.0044 |
| 87 | 0.0009/0.0189 |
| 88 | 0.0083/0.0119 |
| 89 | 0.0088/0.0243 |
| 90 | 0.0091/0.0096 |
| 91 | 0.0035/0.0077 |
| 92 | 0.0151/0.0023 |
| 93 | 0.042/0.0374 |
| 94 | 0.0541/0.0462 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety, attention deficit hyperactivity disorder (ADHD) and diabetes.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

|  |  | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
|  | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

|  |  | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
|  | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

We claim:
1. A compound of formula (I) wherein:

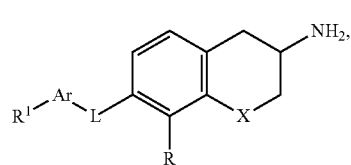

L is —C(O)NH—, —NHC(O)—, —NH— or —NHC(O)NH—;

Ar is phenyl, benzyl, naphthyl or first heteroaryl, said first heteroaryl selected from the group consisting of pyridinyl, pyrazolyl, pyrimidinyl, isoxazolyl and pyrazinyl, wherein Ar may be optionally substituted by one, two or three $R^1$;

$R^1$ is, in each occurrence, independently selected from the group consisting of (a) hydrogen, (b) lower alkyl, (c) lower alkoxy, (d) halogen, (e) cyano, (f) cycloalkyl, (g) NHC(O)-lower alkyl, (h) lower alkoxy substituted by halogen, (i) lower alkyl substituted by halogen, (j) phenyl optionally substituted by one or two halogen atoms, $CF_3O$ or lower alkyl, and (k) a second heteroaryl selected from furanyl, thiazolyl or thiophenyl each optionally substituted by halogen or lower alkyl;

X is $CH_2$;

R is hydrogen or halogen;

or a pharmaceutically acceptable acid addition salt thereof, and a racemic mixture, enantiomer or mixture of enantiomers.

2. The compound according to claim 1 wherein L is —C(O)NH—.

3. The compound according to claim 2, said compound selected from the group consisting of:
N-(6-amino-5,6,7,8-tetrahydronaphthalen-2-yl)-2-(trifluoromethyl)isonicotinamide;
N-(6-amino-5,6,7,8-tetrahydronaphthalen-2-yl)-4-bromo-5-cyclopropyl-1H-pyrazole-3-carboxamide;
N-(6-amino-5,6,7,8-tetrahydronaphthalen-2-yl)-1-(2,2-difluoroethyl)-5-propyl-1H-pyrazole-3-carboxamide;
(R)—N-(6-amino-5,6,7,8-tetrahydronaphthalen-2-yl)-1-(2,2-difluoroethyl)-5-propyl-1H-pyrazole-3-carboxamide;
(S)—N-(6-amino-5,6,7,8-tetrahydronaphthalen-2-yl)-1-(2,2-difluoroethyl)-5-propyl-1H-pyrazole-3-carboxamide;
(R)—N-(6-amino-5,6,7,8-tetrahydronaphthalen-2-yl)-6-methyl-2-(trifluoromethyl)-pyrimidine-4-carboxamide;
(S)—N-(6-amino-5,6,7,8-tetrahydronaphthalen-2-yl)-6-methyl-2-(trifluoromethyl)-pyrimidine-4-carboxamide;
(R)—N-(6-amino-5,6,7,8-tetrahydronaphthalen-2-yl)-4-chlorobenzamide;
(R)—N-(6-amino-5,6,7,8-tetrahydronaphthalen-2-yl)-2-chlorobenzamide;
(S)—N-(6-amino-5,6,7,8-tetrahydronaphthalen-2-yl)-2-methylisonicotinamide;
(S)-2-acetamido-N-(6-amino-5,6,7,8-tetrahydronaphthalen-2-yl)isonicotinamide;
(S)—N-(6-amino-5,6,7,8-tetrahydronaphthalen-2-yl)-2-ethoxyisonicotinamide;
(S)—N-(6-amino-5,6,7,8-tetrahydronaphthalen-2-yl)-6-(trifluoromethyl)nicotinamide;
(S)—N-(6-amino-5,6,7,8-tetrahydronaphthalen-2-yl)-6-methoxynicotinamide;
(S)—N-(6-amino-5,6,7,8-tetrahydronaphthalen-2-yl)-6-(2,2,2-trifluoroethoxy)nicotinamide;
(S)—N-(6-amino-5,6,7,8-tetrahydronaphthalen-2-yl)-4-chloro-3-(5-chlorofuran-2-yl)-1H-pyrazole-5-carboxamide;
(S)—N-(6-amino-5,6,7,8-tetrahydronaphthalen-2-yl)-4-chloro-5-methylisoxazole-3-carboxamide;
(S)—N-(6-amino-5,6,7,8-tetrahydronaphthalen-2-yl)-1-p-tolyl-1H-pyrazole-4-carboxamide;
(S)—N-(6-amino-5,6,7,8-tetrahydronaphthalen-2-yl)-1-(3,4-dichlorophenyl)-1H-pyrazole-4-carboxamide;
(S)—N-(6-amino-5,6,7,8-tetrahydronaphthalen-2-yl)-1-(4-(trifluoromethoxy)phenyl)-1H-pyrazole-4-carboxamide;
(S)—N-(6-amino-5,6,7,8-tetrahydronaphthalen-2-yl)-2-fluoronicotinamide;
(S)—N-(6-amino-5,6,7,8-tetrahydronaphthalen-2-yl)-6-chloronicotinamide;
(S)—N-(6-amino-5,6,7,8-tetrahydronaphthalen-2-yl)-5,6-dichloronicotinamide;
(S)—N-(6-amino-5,6,7,8-tetrahydronaphthalen-2-yl)-3,4-difluorobenzamide;
(S)—N-(6-amino-5,6,7,8-tetrahydronaphthalen-2-yl)-2-naphthamide;
(S)—N-(6-amino-5,6,7,8-tetrahydronaphthalen-2-yl)-2-(trifluoromethyl)isonicotinamide;
(S)—N-(6-amino-5,6,7,8-tetrahydronaphthalen-2-yl)-2,6-dichloroisonicotinamide;
(S)—N-(6-amino-5,6,7,8-tetrahydronaphthalen-2-yl)-5-chloronicotinamide;
(S)—N-(6-amino-5,6,7,8-tetrahydronaphthalen-2-yl)-2-chloro-6-methylisonicotinamide;
(S)—N-(6-amino-5,6,7,8-tetrahydronaphthalen-2-yl)-3-ethyl-4-methyl-1H-pyrazole-5-carboxamide;
(S)—N-(6-amino-5,6,7,8-tetrahydronaphthalen-2-yl)-4-bromo-5-(2,2-difluoroethoxy)-1-ethyl-1H-pyrazole-3-carboxamide;
(S)—N-(6-amino-1-chloro-5,6,7,8-tetrahydronaphthalen-2-yl)-6-chloronicotinamide;

or, a pharmaceutically acceptable acid addition salt thereof, and a racemic mixture, enantiomer or mixture of enantiomers.

4. The compound according to claim 1, wherein L is —NHC(O)—.

5. The compound according to claim 4, which compound is selected from the group consisting of:
6-amino-N-(6-ethoxypyridin-3-yl)-5,6,7,8-tetrahydronaphthalene-2-carboxamide;
6-amino-N-(2-cyclopropylpyrimidin-5-yl)-5,6,7,8-tetrahydronaphthalene-2-carboxamide;
6-amino-N-(5-(trifluoromethyl)pyrazin-2-yl)-5,6,7,8-tetrahydronaphthalene-2-carboxamide;
6-amino-N-(4-(trifluoromethyl)phenyl)-5,6,7,8-tetrahydronaphthalene-2-carboxamide;
6-amino-N-(4-(trifluoromethyl)benzyl)-5,6,7,8-tetrahydronaphthalene-2-carboxamide;
6-amino-N-((6-chloropyridin-3-yl)methyl)-5,6,7,8-tetrahydronaphthalene-2-carboxamide;
6-amino-N-(6-chloropyridin-3-yl)-5,6,7,8-tetrahydronaphthalene-2-carboxamide;
6-amino-N-(3-methoxyphenyl)-5,6,7,8-tetrahydronaphthalene-2-carboxamide;
6-amino-N-(3-(trifluoromethoxy)phenyl)-5,6,7,8-tetrahydronaphthalene-2-carboxamide;
6-amino-N-(4-ethylphenyl)-5,6,7,8-tetrahydronaphthalene-2-carboxamide;
6-amino-N-(4-chlorophenyl)-5,6,7,8-tetrahydronaphthalene-2-carboxamide;
6-amino-N-(4-fluorophenyl)-5,6,7,8-tetrahydronaphthalene-2-carboxamide;
6-amino-N-(3-chlorophenyl)-5,6,7,8-tetrahydronaphthalene-2-carboxamide;
6-amino-N-(4-cyclopropylphenyl)-5,6,7,8-tetrahydronaphthalene-2-carboxamide;
6-amino-N-(4-cyanophenyl)-5,6,7,8-tetrahydronaphthalene-2-carboxamide;

(R)-6-amino-N-(3-(trifluoromethoxy)phenyl)-5,6,7,8-tetrahydronaphthalene-2-carboxamide; and, (S)-6-amino-N-(3-(trifluoromethoxy)phenyl)-5,6,7,8-tetrahydronaphthalene-2-carboxamide; or, a pharmaceutically acceptable acid addition salt thereof, and a racemic mixture, enantiomer or mixture of enantiomers.

6. The compound according to claim 1, wherein L is NH—.

7. The compound according to claim 6, which compound is selected from the group consisting of:
- (S)—N6-(5-(trifluoromethyl)pyrimidin-2-yl)-1,2,3,4-tetrahydronaphthalene-2,6-diamine;
- (S)—N6-(5-chloropyrimidin-2-yl)-1,2,3,4-tetrahydronaphthalene-2,6-diamine;
- (S)—N6-(5-(trifluoromethyl)pyridin-2-yl)-1,2,3,4-tetrahydronaphthalene-2,6-diamine;
- (S)—N6-(4-(trifluoromethyl)phenyl)-1,2,3,4-tetrahydronaphthalene-2,6-diamine;
- (S)-4-(6-amino-5,6,7,8-tetrahydronaphthalen-2-ylamino)benzonitrile;
- (S)—N6-(4-chlorophenyl)-1,2,3,4-tetrahydronaphthalene-2,6-diamine;
- (S)—N6-(4-ethylphenyl)-1,2,3,4-tetrahydronaphthalene-2,6-diamine;
- (S)—N6-(3-(trifluoromethoxy)phenyl)-1,2,3,4-tetrahydronaphthalene-2,6-diamine;
- (S)—N6-(4-fluorophenyl)-1,2,3,4-tetrahydronaphthalene-2,6-diamine;
- (S)—N6-(3-chlorophenyl)-1,2,3,4-tetrahydronaphthalene-2,6-diamine;
- (S)—N6-(4-cyclopropylphenyl)-1,2,3,4-tetrahydronaphthalene-2,6-diamine;
- (S)—N6-(4-chlorobenzyl)-1,2,3,4-tetrahydronaphthalene-2,6-diamine;
- (S)—N6-(3-Methoxyphenyl)-1,2,3,4-tetrahydronaphthalene-2,6-diamine; or, a pharmaceutically acceptable acid addition salt thereof, and a racemic mixture, enantiomer or mixture of enantiomers.

8. The compound according to claim 1, wherein L is —NHC(O)NH—.

9. The compound according to claim 8, which compound is selected from the group consisting of:
- (S)-1-(6-amino-5,6,7,8-tetrahydronaphthalen-2-yl)-3-(6-(trifluoromethyl)pyridin-3-yl)urea;
- (S)-1-(6-amino-5,6,7,8-tetrahydronaphthalen-2-yl)-3-(4-(trifluoromethyl)phenyl)urea;
- (S)-1-(6-amino-5,6,7,8-tetrahydronaphthalen-2-yl)-3-((5-chloropyridin-2-yl)methyl)urea;
- (S)-1-(6-amino-5,6,7,8-tetrahydronaphthalen-2-yl)-3-(3-(trifluoromethoxy)benzyl)urea;
- (S)-1-(6-amino-5,6,7,8-tetrahydronaphthalen-2-yl)-3-(4-ethylphenyl)urea;
- (S)-1-(6-amino-5,6,7,8-tetrahydronaphthalen-2-yl)-3-(4-(trifluoromethoxy)phenyl)urea;
- (S)-1-(6-amino-5,6,7,8-tetrahydronaphthalen-2-yl)-3-(3-methoxyphenyl)urea;
- (S)-1-(6-amino-5,6,7,8-tetrahydronaphthalen-2-yl)-3-(4-chlorobenzyl)urea;
- (S)-1-(6-amino-5,6,7,8-tetrahydronaphthalen-2-yl)-3-(4-cyanophenyl)urea;
- (S)-1-(6-amino-5,6,7,8-tetrahydronaphthalen-2-yl)-3-(4-cyclopropylphenyl)urea; and,
- (S)-1-(6-amino-5,6,7,8-tetrahydronaphthalen-2-yl)-3-(4-chlorophenyl)urea; or, a pharmaceutically acceptable acid addition salt thereof, and a racemic mixture, enantiomer or mixture of enantiomers.

10. A pharmaceutical composition comprising a compound according to claim 1 and at least one pharmaceutically acceptable carrier, adjuvant or excipient.

* * * * *